United States Patent
Martin et al.

(10) Patent No.: US 12,383,628 B2
(45) Date of Patent: Aug. 12, 2025

(54) HYDROGEL-FORMING COMPOSITION FOR CONTROLLED RELEASE

(71) Applicants: Universiteit Gent, Ghent (BE); Vrije Universiteit Brussel, Brussels (BE)

(72) Inventors: Charlotte Martin, Brussels (BE); Annemieke Madder, Massemen (BE); Steven Ballet, Itegem (BE); Richard Hoogenboom, Terneuzen (NL)

(73) Assignees: Vrije Universiteit Brussel, Brussels (BE); Universiteit Gent, Ghent (BE)

( * ) Notice: Subject to any disclaimer, the term of this patent is extended or adjusted under 35 U.S.C. 154(b) by 614 days.

(21) Appl. No.: 15/998,916

(22) PCT Filed: Feb. 16, 2017

(86) PCT No.: PCT/EP2017/053518
§ 371 (c)(1),
(2) Date: Oct. 29, 2018

(87) PCT Pub. No.: WO2017/140792
PCT Pub. Date: Aug. 24, 2017

(65) Prior Publication Data
US 2020/0246472 A1      Aug. 6, 2020

(30) Foreign Application Priority Data

Feb. 16, 2016   (EP) ..................................... 16155987
Sep. 5, 2016    (WO) .................. PCT/EP2016/070875

(51) Int. Cl.
| | |
|---|---|
| A61K 9/00 | (2006.01) |
| A61K 9/06 | (2006.01) |
| A61K 31/485 | (2006.01) |
| A61K 47/64 | (2017.01) |
| A61K 49/00 | (2006.01) |
| A61K 51/08 | (2006.01) |
| A61K 51/12 | (2006.01) |
| A61P 25/04 | (2006.01) |

(52) U.S. Cl.
CPC ............ *A61K 47/64* (2017.08); *A61K 9/0019* (2013.01); *A61K 9/06* (2013.01); *A61K 31/485* (2013.01); *A61K 49/0056* (2013.01); *A61K 49/0073* (2013.01); *A61K 51/088* (2013.01); *A61K 51/1213* (2013.01); *A61P 25/04* (2018.01)

(58) Field of Classification Search
CPC ........ A61K 47/64; A61K 9/0019; A61K 9/06; A61K 31/485; A61K 49/0056; A61K 49/0073; A61K 51/088; A61K 51/1213; A61K 47/42; A61K 47/6903; A61K 49/0032; A61K 38/00; A61P 25/04
See application file for complete search history.

(56) References Cited

U.S. PATENT DOCUMENTS

| | | | |
|---|---|---|---|
| 3,891,616 | A | 6/1975 | Ondetti |
| 2005/0181973 | A1 | 8/2005 | Genove et al. |
| 2014/0302144 | A1 | 10/2014 | Koutsopoulos et al. |

FOREIGN PATENT DOCUMENTS

| | | | | |
|---|---|---|---|---|
| EP | 0498508 | A1 | 8/1992 | |
| EP | 2180027 | | 4/2010 | |
| EP | 15176415 | * | 7/2013 | |
| GB | 2496654 | | 5/2013 | |
| JP | 2012082180 | | 4/2012 | |
| WO | 2013072686 | | 5/2013 | |
| WO | WO-2014104974 | A2 * | 7/2014 | ............ A61K 38/08 |
| WO | 2014152751 | A1 | 9/2014 | |
| WO | 2015116242 | | 8/2015 | |
| WO | 2017009358 | A1 | 1/2017 | |
| WO | 2017140792 | A1 | 8/2017 | |

OTHER PUBLICATIONS

Bibian et al. (J. Mater. Chem. B 2015, 3, 759-765).*
PCT International Preliminary Report on Patentability PCT/EP2017/053518, dated Mar. 21, 2018.
PCT International Search Report and Written Opinion PCT/EP2017053518, dated Mar. 8, 2017.
Bibian et al., Rational design of hexapeptide hydrogelator for controlled-release drug delivery, Journal of Materials Chemistyr B, Jan. 1, 2015, pp. 759-765, col. 3, No. 5.
Hariton et al. Bioavailability of beta-amino acid and C-terminally derived PK/PBAN analogs. Peptides. May 22, 2009, vol. 30, pp. 2174-2181. (Year: 2009).
Mangelschots et al. Mixes alpha/beta-Peptides as a Class of Short Amphipathic Peptide Hydrogelators with Enhanced Proteolytic Stability. BioMacromolecules. Jan. 7, 2016, vol. 17, pp. 437-445. (Year: 2016).
PCT International Search Report and Written Opinion, PCT/EP2016/066583, mailing date Sep. 23, 2016.
Sobolewski et al., Analogues of arginine vasopressin and its agonist and antagonist modified in the N-terminal part of the molecular with I-beta-homophenylalanine, Journal of Peptide Research, Apr. 1, 2005, pp. 465-471, col. 65, No. 4.

* cited by examiner

*Primary Examiner* — Michael G. Hartley
*Assistant Examiner* — Melissa J Perreira
(74) *Attorney, Agent, or Firm* — Patent Law Works LLP

(57) ABSTRACT

The present invention provides peptide hydrogelators capable of forming hydrogels as carriers of active ingredients and acting as sustained or controlled release drug delivery systems.

23 Claims, 23 Drawing Sheets

Specification includes a Sequence Listing.

FIGURE 8
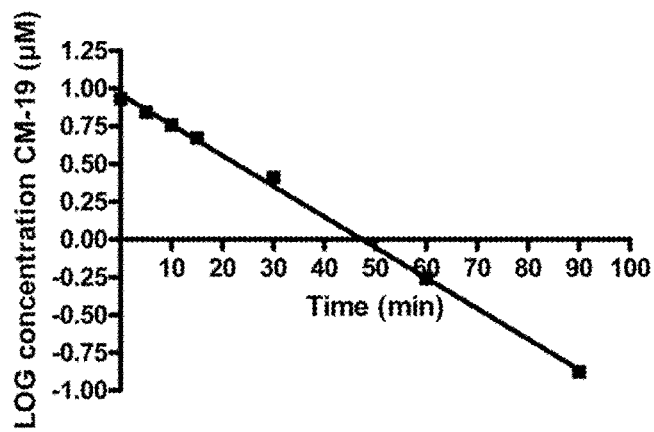
A: ULA  FIGURE 9A
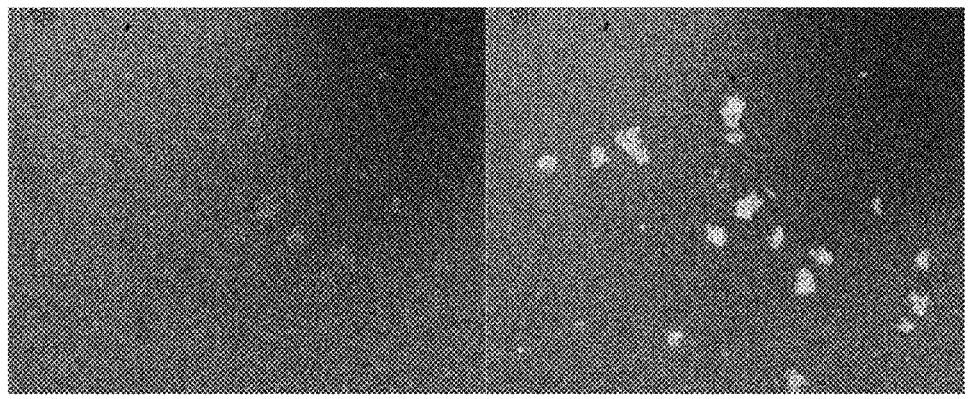
B: Control TCPS  FIGURE 9B
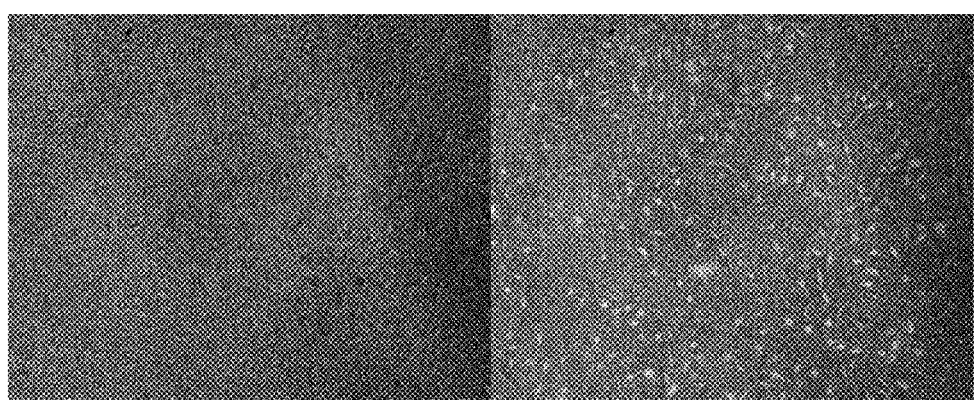

C: hydrogelator 2  FIGURE 9C
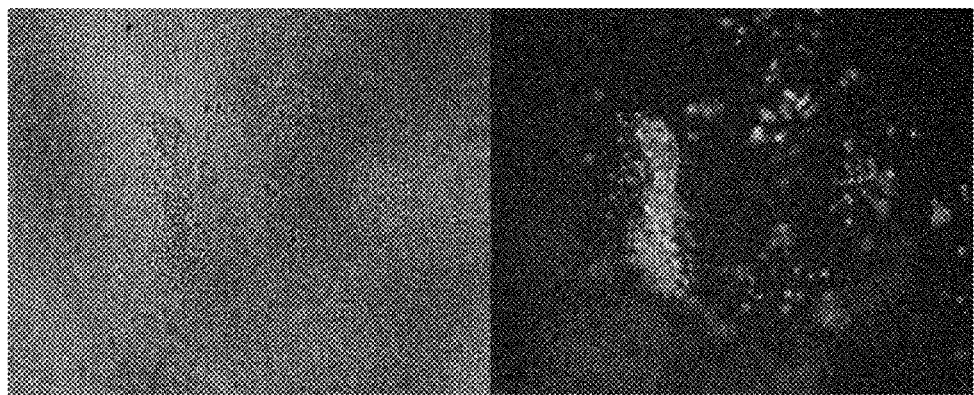
D: hydrogelator 4  FIGURE 9D
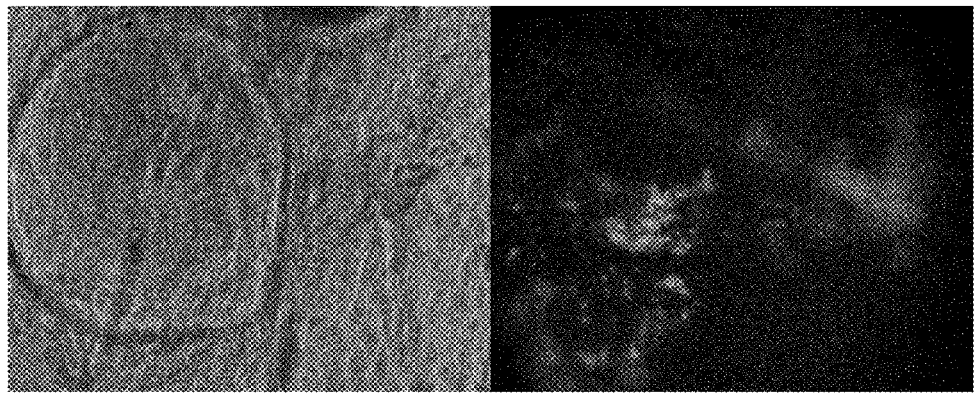

FIGURE 11
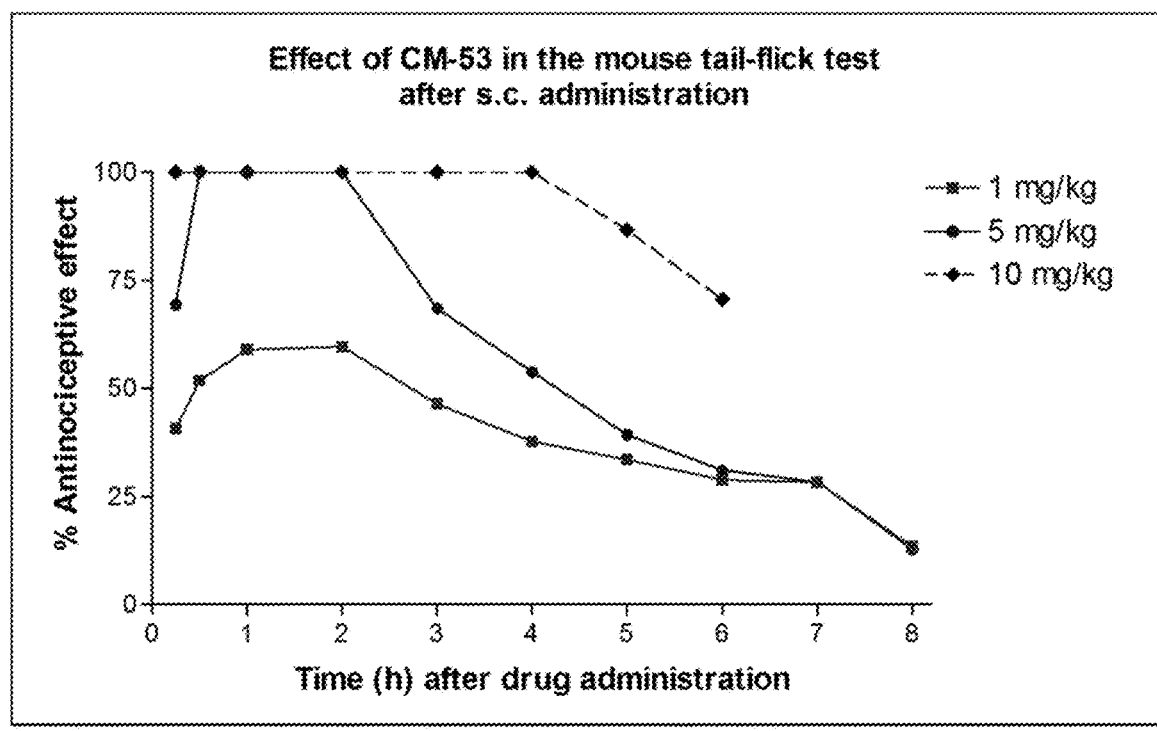
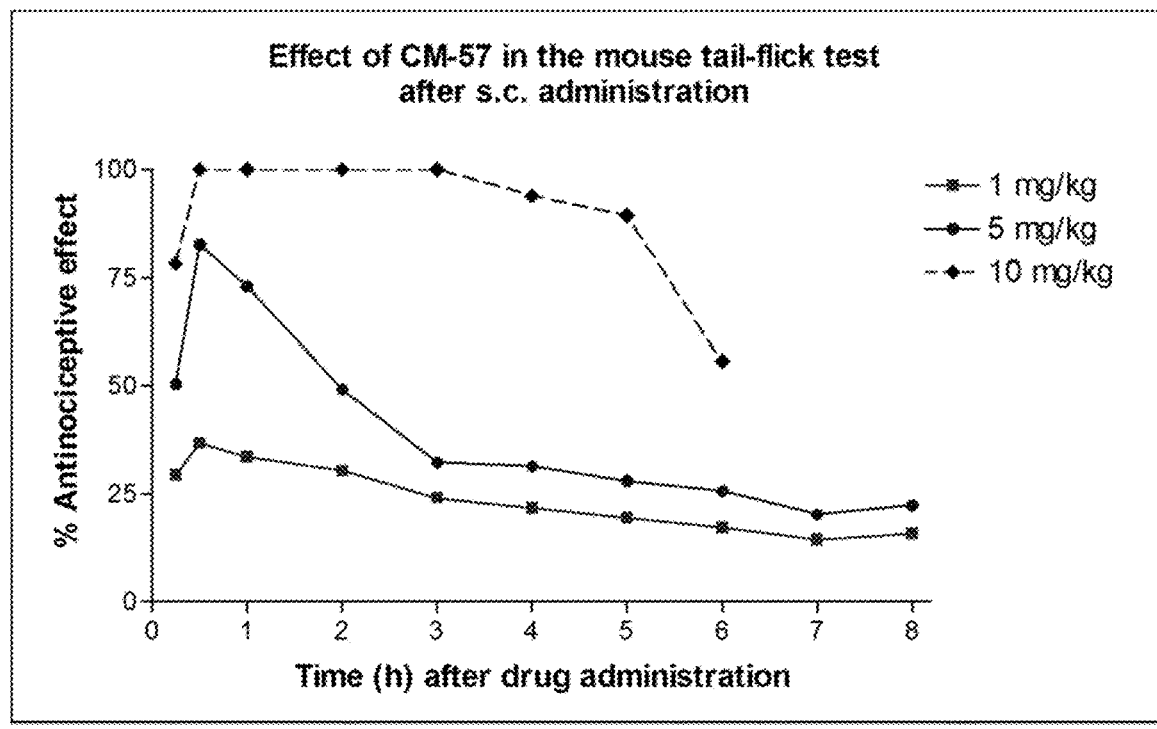

FIGURE 22
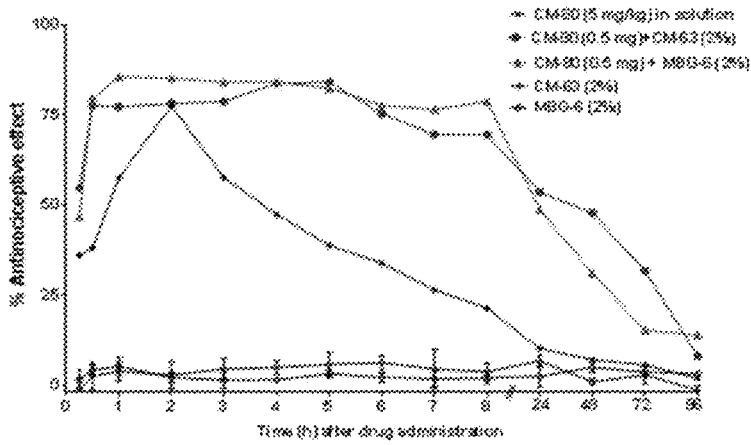
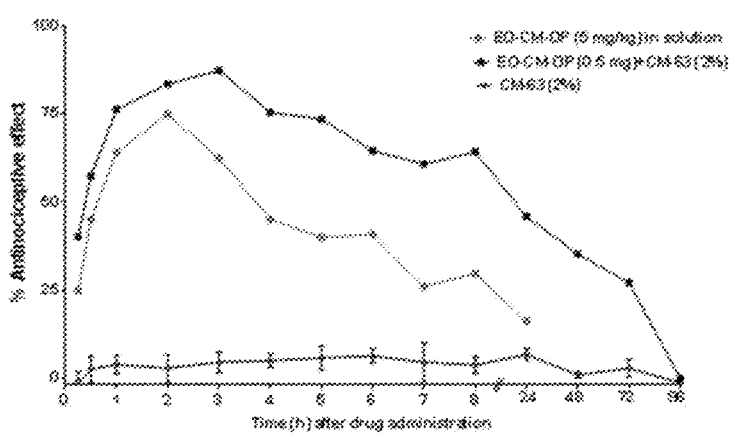
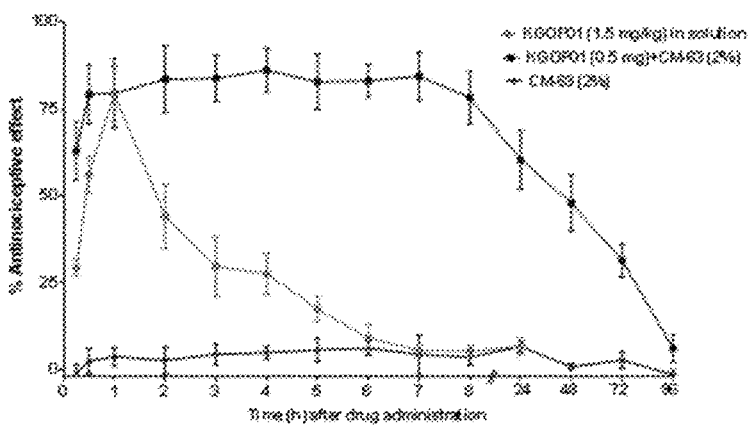

FIGURE 23
CM-58
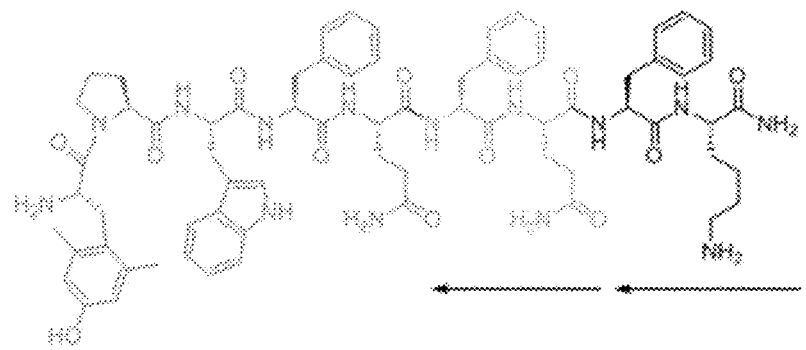
CM-136
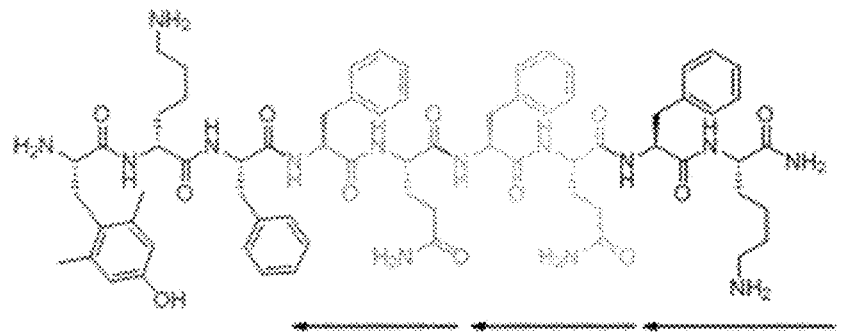
CM-137
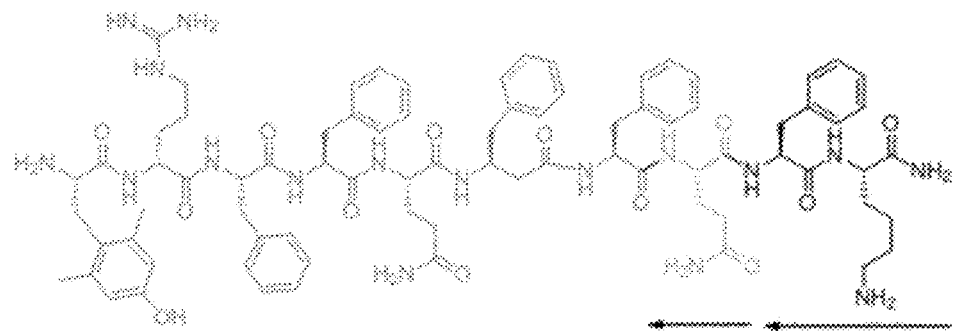

FIGURE 26
A
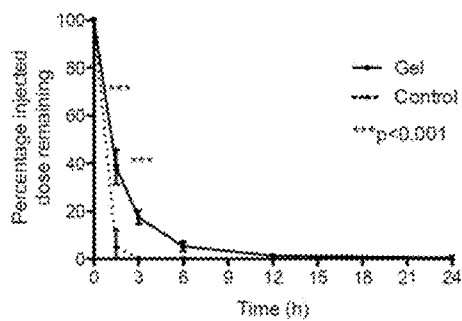
B
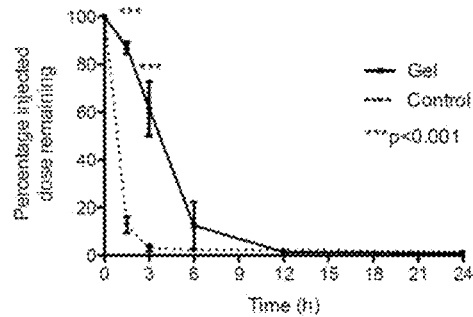
C
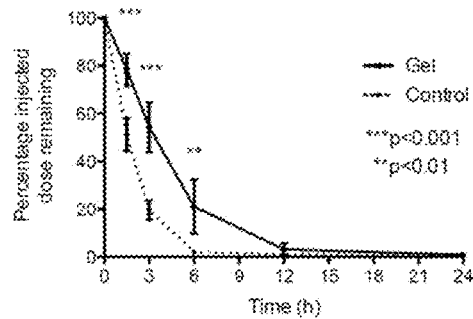

H-Tyr-DArg-Phe-Phe-Spacer-Gln-β³hPhe-Phe-Gln-Phe-Lys-NH₂

| Sequence | Minimum gelation concentration (w/v% in PBS) | Classification |
|---|---|---|
| H-Phe-Glu-Phe-Gln-Phe-Lys-OH | 1 (in mQ:PBS 50:50) | ●②●④●⑥ |
| H-Phe-Glu-Phe-Gln-Phe-Lys-NH₂ | 2 | ●②●④●⑥ |
| H-Phe-Glu-Phe-Asn-Phe-Lys-OH | 1 | ●②●④●⑥ |
| H-Phe-Glu-Phe-Asn-Phe-Lys-NH₂ | 1 | ●②●④●⑥ |
| H-Trp-Glu-Trp-Gln-Trp-Lys-NH₂ | 1 | ●②●④●⑥ |
| H-(2-Nal)-Glu-(2-Nal)-Gln-(2-Nal)-Lys-NH₂ | 2 | ●②●④●⑥ |
| H-Ile-Glu-Ile-Gln-Ile-NH₂ | 2 | ●②●④●⑥ |
| H-Cha-Glu-Cha-Gln-Cha-Lys-NH₂ | 2 | ●②●④●⑥ |
| H-Trp-Glu-Phe-Gln-Phe-Lys-NH₂ | 2 | ●②●④●⑥ |
| H-Phe-Glu-Phe-Gln-Trp-Lys-NH₂ | 2 | ●②●④●⑥ |
| H-Phe-Glu-Trp-Gln-Phe-Lys-NH₂ | 3 | ●②●④●⑥ |
| H-Phe-Gln-Phe-Gln-Phe-Lys-NH₂ | 2 | ●②●④●⑥ |
| H-DPhe-DGlu-DPhe-DGln-DPhe-DLys-NH2 | 2 | ●②●④●⑥ |
| H-Lys-Phe-Gln-Phe-Glu-Phe-NH₂ | 2 | ①●③●⑤● |
| H-DLys-DPhe-DGln-DPhe-DGlu-DPhe-NH2 | 2 | ①●③●⑤● |
| H-Phe-Glu-Phe-Lys-Phe-Ser-NH₂ | 1 | ●②●④●⑥ |

FIGURE 29

SEQUENCE LISTING

```
<160> NUMBER OF SEQ ID NOS: 58

<210> SEQ ID NO 1
<211> LENGTH: 6
<212> TYPE: PRT
<213> ORGANISM: Artificial Sequence
<220> FEATURE:
<223> OTHER INFORMATION: hydrogelator peptides

<400> SEQUENCE: 1

Phe Glu Phe Gln Phe Lys
1               5

<210> SEQ ID NO 2
<211> LENGTH: 6
<212> TYPE: PRT
<213> ORGANISM: Artificial Sequence
<220> FEATURE:
<223> OTHER INFORMATION: hydrogelator peptides
<220> FEATURE:
<221> NAME/KEY: Amide-group
<222> LOCATION: (6)..(6)

<400> SEQUENCE: 2

Phe Glu Phe Gln Phe Lys
1               5

<210> SEQ ID NO 3
<211> LENGTH: 6
<212> TYPE: PRT
<213> ORGANISM: Artificial Sequence
<220> FEATURE:
<223> OTHER INFORMATION: hydrogelator peptides
<220> FEATURE:
<221> NAME/KEY: acetylated
<222> LOCATION: (1)..(1)
<220> FEATURE:
<221> NAME/KEY: Amide-group
<222> LOCATION: (6)..(6)

<400> SEQUENCE: 3

Phe Glu Phe Gln Phe Lys
1               5

<210> SEQ ID NO 4
<211> LENGTH: 6
<212> TYPE: PRT
<213> ORGANISM: Artificial Sequence
<220> FEATURE:
<223> OTHER INFORMATION: hydrogelator peptides
<220> FEATURE:
<221> NAME/KEY: D-isomer
<222> LOCATION: (1)..(6)
<220> FEATURE:
<221> NAME/KEY: Amide-group
<222> LOCATION: (6)..(6)

<400> SEQUENCE: 4

Phe Glu Phe Gln Phe Lys
1               5

<210> SEQ ID NO 5
<211> LENGTH: 6
<212> TYPE: PRT
<213> ORGANISM: Artificial Sequence
<220> FEATURE:
<223> OTHER INFORMATION: hydrogelator peptides
<220> FEATURE:
<221> NAME/KEY: Amide-group
<222> LOCATION: (6)..(6)
```

```
<400> SEQUENCE: 5

Ile Glu Ile Gln Ile Lys
1               5

<210> SEQ ID NO 6
<211> LENGTH: 6
<212> TYPE: PRT
<213> ORGANISM: Artificial Sequence
<220> FEATURE:
<223> OTHER INFORMATION: hydrogelator peptides
<220> FEATURE:
<221> NAME/KEY: Amide-group
<222> LOCATION: (6)..(6)

<400> SEQUENCE: 6

Leu Glu Leu Gln Leu Lys
1               5

<210> SEQ ID NO 7
<211> LENGTH: 6
<212> TYPE: PRT
<213> ORGANISM: Artificial Sequence
<220> FEATURE:
<223> OTHER INFORMATION: hydrogelator peptides
<220> FEATURE:
<221> NAME/KEY: Amide-group
<222> LOCATION: (6)..(6)

<400> SEQUENCE: 7

Val Glu Val Gln Val Lys
1               5

<210> SEQ ID NO 8
<211> LENGTH: 6
<212> TYPE: PRT
<213> ORGANISM: Artificial Sequence
<220> FEATURE:
<223> OTHER INFORMATION: hydrogelator peptides
<220> FEATURE:
<221> NAME/KEY: Amide-group
<222> LOCATION: (6)..(6)

<400> SEQUENCE: 8

Ala Glu Ala Gln Ala Lys
1               5

<210> SEQ ID NO 9
<211> LENGTH: 6
<212> TYPE: PRT
<213> ORGANISM: Artificial Sequence
<220> FEATURE:
<223> OTHER INFORMATION: hydrogelator peptides
<220> FEATURE:
<221> NAME/KEY: misc_feature
<222> LOCATION: (1)..(1)
<223> OTHER INFORMATION: X=beta-cyclohexylalanine
<220> FEATURE:
<221> NAME/KEY: misc_feature
<222> LOCATION: (3)..(3)
<223> OTHER INFORMATION: X=beta-cyclohexylalanine
<220> FEATURE:
<221> NAME/KEY: misc_feature
<222> LOCATION: (5)..(5)
<223> OTHER INFORMATION: X=beta-cyclohexylalanine
<220> FEATURE:
<221> NAME/KEY: Amide-group
<222> LOCATION: (6)..(6)

<400> SEQUENCE: 9
```

```
Xaa Glu Xaa Gln Xaa Lys
1               5

<210> SEQ ID NO 10
<211> LENGTH: 6
<212> TYPE: PRT
<213> ORGANISM: Artificial Sequence
<220> FEATURE:
<223> OTHER INFORMATION: hydrogelator peptides

<400> SEQUENCE: 10

Phe Glu Phe Asn Phe Lys
1               5

<210> SEQ ID NO 11
<211> LENGTH: 6
<212> TYPE: PRT
<213> ORGANISM: Artificial Sequence
<220> FEATURE:
<223> OTHER INFORMATION: hydrogelator peptides
<220> FEATURE:
<221> NAME/KEY: Amide-group
<222> LOCATION: (6)..(6)

<400> SEQUENCE: 11

Phe Glu Phe Asn Phe Lys
1               5

<210> SEQ ID NO 12
<211> LENGTH: 6
<212> TYPE: PRT
<213> ORGANISM: Artificial Sequence
<220> FEATURE:
<223> OTHER INFORMATION: hydrogelator peptides
<220> FEATURE:
<221> NAME/KEY: Amide-group
<222> LOCATION: (6)..(6)

<400> SEQUENCE: 12

Trp Glu Trp Gln Trp Lys
1               5

<210> SEQ ID NO 13
<211> LENGTH: 6
<212> TYPE: PRT
<213> ORGANISM: Artificial Sequence
<220> FEATURE:
<223> OTHER INFORMATION: hydrogelator peptides
<220> FEATURE:
<221> NAME/KEY: misc_feature
<222> LOCATION: (1)..(1)
<223> OTHER INFORMATION: X=2-Naphthylalanine
<220> FEATURE:
<221> NAME/KEY: misc_feature
<222> LOCATION: (3)..(3)
<223> OTHER INFORMATION: X=2-Naphthylalanine
<220> FEATURE:
<221> NAME/KEY: misc_feature
<222> LOCATION: (5)..(5)
<223> OTHER INFORMATION: X=2-Naphthylalanine
<220> FEATURE:
<221> NAME/KEY: Amide-group
<222> LOCATION: (6)..(6)

<400> SEQUENCE: 13

Xaa Glu Xaa Gln Xaa Lys
1               5

<210> SEQ ID NO 14
<211> LENGTH: 6
```

```
<212> TYPE: PRT
<213> ORGANISM: Artificial Sequence
<220> FEATURE:
<223> OTHER INFORMATION: hydrogelator peptides
<220> FEATURE:
<221> NAME/KEY: Amide-group
<222> LOCATION: (6)..(6)

<400> SEQUENCE: 14

Trp Glu Phe Gln Phe Lys
1               5

<210> SEQ ID NO 15
<211> LENGTH: 6
<212> TYPE: PRT
<213> ORGANISM: Artificial Sequence
<220> FEATURE:
<223> OTHER INFORMATION: hydrogelator peptides
<220> FEATURE:
<221> NAME/KEY: Amide-group
<222> LOCATION: (6)..(6)

<400> SEQUENCE: 15

Phe Glu Phe Gln Trp Lys
1               5

<210> SEQ ID NO 16
<211> LENGTH: 6
<212> TYPE: PRT
<213> ORGANISM: Artificial Sequence
<220> FEATURE:
<223> OTHER INFORMATION: hydrogelator peptides
<220> FEATURE:
<221> NAME/KEY: Amide-group
<222> LOCATION: (6)..(6)

<400> SEQUENCE: 16

Phe Gln Phe Gln Phe Lys
1               5

<210> SEQ ID NO 17
<211> LENGTH: 6
<212> TYPE: PRT
<213> ORGANISM: Artificial Sequence
<220> FEATURE:
<223> OTHER INFORMATION: hydrogelator peptides
<220> FEATURE:
<221> NAME/KEY: D-isomer
<222> LOCATION: (1)..(6)
<220> FEATURE:
<221> NAME/KEY: Amide-group
<222> LOCATION: (6)..(6)

<400> SEQUENCE: 17

Phe Glu Phe Gln Phe Lys
1               5

<210> SEQ ID NO 18
<211> LENGTH: 6
<212> TYPE: PRT
<213> ORGANISM: Artificial Sequence
<220> FEATURE:
<223> OTHER INFORMATION: hydrogelator peptides
<220> FEATURE:
<221> NAME/KEY: Amide-group
<222> LOCATION: (6)..(6)

<400> SEQUENCE: 18

Lys Phe Gln Phe Glu Phe
1               5
```

```
<210> SEQ ID NO 19
<211> LENGTH: 6
<212> TYPE: PRT
<213> ORGANISM: Artificial Sequence
<220> FEATURE:
<223> OTHER INFORMATION: hydrogelator peptides
<220> FEATURE:
<221> NAME/KEY: D-isomer
<222> LOCATION: (1)..(6)
<220> FEATURE:
<221> NAME/KEY: Amide-group
<222> LOCATION: (6)..(6)

<400> SEQUENCE: 19

Lys Phe Gln Phe Glu Phe
1               5

<210> SEQ ID NO 20
<211> LENGTH: 6
<212> TYPE: PRT
<213> ORGANISM: Artificial Sequence
<220> FEATURE:
<223> OTHER INFORMATION: hydrogelator peptides
<220> FEATURE:
<221> NAME/KEY: Amide-group
<222> LOCATION: (6)..(6)

<400> SEQUENCE: 20

Phe Glu Phe Lys Phe Ser
1               5

<210> SEQ ID NO 21
<211> LENGTH: 6
<212> TYPE: PRT
<213> ORGANISM: Artificial Sequence
<220> FEATURE:
<223> OTHER INFORMATION: hydrogelator peptides
<220> FEATURE:
<221> NAME/KEY: Amide-group
<222> LOCATION: (6)..(6)

<400> SEQUENCE: 21

Phe Glu Trp Gln Phe Lys
1               5

<210> SEQ ID NO 22
<211> LENGTH: 6
<212> TYPE: PRT
<213> ORGANISM: Artificial Sequence
<220> FEATURE:
<223> OTHER INFORMATION: hydrogelator peptides
<220> FEATURE:
<221> NAME/KEY: D-isomer
<222> LOCATION: (1)..(6)
<220> FEATURE:
<221> NAME/KEY: Amide-group
<222> LOCATION: (6)..(6)

<400> SEQUENCE: 22

Lys Phe Asn Phe Glu Phe
1               5

<210> SEQ ID NO 23
<211> LENGTH: 6
<212> TYPE: PRT
<213> ORGANISM: Artificial Sequence
<220> FEATURE:
<223> OTHER INFORMATION: hydrogelator peptides
<220> FEATURE:
```

```
<221> NAME/KEY: D-isomer
<222> LOCATION: (1)..(6)
<220> FEATURE:
<221> NAME/KEY: Amide-group
<222> LOCATION: (6)..(6)

<400> SEQUENCE: 23

Lys Phe Glu Phe Glu Phe
1               5

<210> SEQ ID NO 24
<211> LENGTH: 6
<212> TYPE: PRT
<213> ORGANISM: Artificial Sequence
<220> FEATURE:
<223> OTHER INFORMATION: hydrogelator peptides
<220> FEATURE:
<221> NAME/KEY: D-isomer
<222> LOCATION: (1)..(6)
<220> FEATURE:
<221> NAME/KEY: Amide-group
<222> LOCATION: (6)..(6)

<400> SEQUENCE: 24

Lys Phe Gln Phe Glu Phe
1               5

<210> SEQ ID NO 25
<211> LENGTH: 6
<212> TYPE: PRT
<213> ORGANISM: Artificial Sequence
<220> FEATURE:
<223> OTHER INFORMATION: hydrogelator peptides
<220> FEATURE:
<221> NAME/KEY: D-isomer
<222> LOCATION: (1)..(6)

<400> SEQUENCE: 25

Phe Glu Phe Gln Phe Lys
1               5

<210> SEQ ID NO 26
<211> LENGTH: 6
<212> TYPE: PRT
<213> ORGANISM: Artificial Sequence
<220> FEATURE:
<223> OTHER INFORMATION: hydrogelator peptides

<400> SEQUENCE: 26

Lys Phe Gln Phe Glu Phe
1               5

<210> SEQ ID NO 27
<211> LENGTH: 9
<212> TYPE: PRT
<213> ORGANISM: Artificial Sequence
<220> FEATURE:
<223> OTHER INFORMATION: hydrogelator peptides
<220> FEATURE:
<221> NAME/KEY: misc_feature
<222> LOCATION: (1)..(1)
<223> OTHER INFORMATION: X=2',6'-dimethyl-L-tyrosine
<220> FEATURE:
<221> NAME/KEY: D-isomer
<222> LOCATION: (2)..(2)
<220> FEATURE:
<221> NAME/KEY: Amide-group
<222> LOCATION: (9)..(9)

<400> SEQUENCE: 27
```

```
Xaa Lys Phe Phe Glu Phe Gln Phe Lys
1               5

<210> SEQ ID NO 28
<211> LENGTH: 9
<212> TYPE: PRT
<213> ORGANISM: Artificial Sequence
<220> FEATURE:
<223> OTHER INFORMATION: hydrogelator peptides
<220> FEATURE:
<221> NAME/KEY: misc_feature
<222> LOCATION: (1)..(1)
<223> OTHER INFORMATION: X=2',6'-dimethyl-L-tyrosine
<220> FEATURE:
<221> NAME/KEY: Amide-group
<222> LOCATION: (9)..(9)

<400> SEQUENCE: 28

Xaa Pro Phe Phe Glu Phe Gln Phe Lys
1               5

<210> SEQ ID NO 29
<211> LENGTH: 9
<212> TYPE: PRT
<213> ORGANISM: Artificial Sequence
<220> FEATURE:
<223> OTHER INFORMATION: hydrogelator peptides
<220> FEATURE:
<221> NAME/KEY: misc_feature
<222> LOCATION: (1)..(1)
<223> OTHER INFORMATION: X=2',6'-dimethyl-L-tyrosine
<220> FEATURE:
<221> NAME/KEY: Amide-group
<222> LOCATION: (9)..(9)

<400> SEQUENCE: 29

Xaa Pro Phe Phe Gln Phe Gln Phe Lys
1               5

<210> SEQ ID NO 30
<211> LENGTH: 9
<212> TYPE: PRT
<213> ORGANISM: Artificial Sequence
<220> FEATURE:
<223> OTHER INFORMATION: hydrogelator peptides
<220> FEATURE:
<221> NAME/KEY: misc_feature
<222> LOCATION: (1)..(1)
<223> OTHER INFORMATION: X=2',6'-dimethyl-L-tyrosine
<220> FEATURE:
<221> NAME/KEY: D-isomer
<222> LOCATION: (2)..(2)
<220> FEATURE:
<221> NAME/KEY: Amide-group
<222> LOCATION: (9)..(9)

<400> SEQUENCE: 30

Xaa Arg Phe Phe Gln Phe Gln Phe Lys
1               5

<210> SEQ ID NO 31
<211> LENGTH: 9
<212> TYPE: PRT
<213> ORGANISM: Artificial Sequence
<220> FEATURE:
<223> OTHER INFORMATION: hydrogelator peptides
<220> FEATURE:
<221> NAME/KEY: misc_feature
<222> LOCATION: (1)..(1)
<223> OTHER INFORMATION: X=2',6'-dimethyl-L-tyrosine
<220> FEATURE:
<221> NAME/KEY: Amide-group
```

```
<222> LOCATION: (9)..(9)

<400> SEQUENCE: 31

Xaa Pro Trp Phe Gln Phe Gln Phe Lys
1               5

<210> SEQ ID NO 32
<211> LENGTH: 9
<212> TYPE: PRT
<213> ORGANISM: Artificial Sequence
<220> FEATURE:
<223> OTHER INFORMATION: hydrogelator peptides
<220> FEATURE:
<221> NAME/KEY: misc_feature
<222> LOCATION: (1)..(1)
<223> OTHER INFORMATION: X=2',6'-dimethyl-L-tyrosine
<220> FEATURE:
<221> NAME/KEY: D-isomer
<222> LOCATION: (2)..(2)
<220> FEATURE:
<221> NAME/KEY: misc_feature
<222> LOCATION: (3)..(3)
<223> OTHER INFORMATION: Z=4-amino-1,2,4,5-tetrahydro-2-benzazepinone -
      beta-Alanine
<220> FEATURE:
<221> NAME/KEY: Amide-group
<222> LOCATION: (9)..(9)

<400> SEQUENCE: 32

Xaa Arg Xaa Phe Gln Phe Gln Phe Lys
1               5

<210> SEQ ID NO 33
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: beta-3-homoPhe
<220> FEATURE:
<221> NAME/KEY: MISC_FEATURE
<222> LOCATION: (7)..(7)
<223> OTHER INFORMATION: NH2 substituted

<400> SEQUENCE: 33

Phe Glu Phe Phe Gln Phe Lys
1               5

<210> SEQ ID NO 34
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: beta-3-homoPhe
<220> FEATURE:
<221> NAME/KEY: MISC_FEATURE
<222> LOCATION: (7)..(7)
<223> OTHER INFORMATION: NH2 substituted

<400> SEQUENCE: 34

Phe Gln Phe Phe Gln Phe Lys
1               5

<210> SEQ ID NO 35
```

```
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (4)..(4)
<223> OTHER INFORMATION: beta-3- homoPhe
<220> FEATURE:
<221> NAME/KEY: MISC_FEATURE
<222> LOCATION: (7)..(7)
<223> OTHER INFORMATION: NH2 substituted

<400> SEQUENCE: 35

Lys Phe Gln Phe Phe Glu Phe
1               5

<210> SEQ ID NO 36
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: D-isomer
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (3)..(3)
<223> OTHER INFORMATION: D-isomer
<220> FEATURE:
<221> NAME/KEY: MISC_FEATURE
<222> LOCATION: (4)..(4)
<223> OTHER INFORMATION: beta-3-homoPhe
<220> FEATURE:
<221> NAME/KEY: MISC_FEATURE
<222> LOCATION: (5)..(5)
<223> OTHER INFORMATION: D-isomer
<220> FEATURE:
<221> NAME/KEY: MISC_FEATURE
<222> LOCATION: (6)..(6)
<223> OTHER INFORMATION: D-isomer
<220> FEATURE:
<221> NAME/KEY: MISC_FEATURE
<222> LOCATION: (7)..(7)
<223> OTHER INFORMATION: D-isomer
<220> FEATURE:
<221> NAME/KEY: MISC_FEATURE
<222> LOCATION: (7)..(7)
<223> OTHER INFORMATION: NH2 substituted

<400> SEQUENCE: 36

Lys Phe Gln Phe Phe Glu Phe
1               5

<210> SEQ ID NO 37
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: bromine substituted at position 3 of the ring
<220> FEATURE:
<221> NAME/KEY: MISC_FEATURE
<222> LOCATION: (6)..(6)
<223> OTHER INFORMATION: NH2 substituted
```

```
<400> SEQUENCE: 37

Phe Gln Phe Gln Phe Lys
1               5

<210> SEQ ID NO 38
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: bromine substituted at position 3 of the ring
<220> FEATURE:
<221> NAME/KEY: MISC_FEATURE
<222> LOCATION: (5)..(5)
<223> OTHER INFORMATION: bromine substituted at position 3 of the ring
<220> FEATURE:
<221> NAME/KEY: MISC_FEATURE
<222> LOCATION: (6)..(6)
<223> OTHER INFORMATION: NH2 substituted

<400> SEQUENCE: 38

Phe Gln Phe Gln Phe Lys
1               5

<210> SEQ ID NO 39
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: bromine substituted at position 3 of the ring
<220> FEATURE:
<221> NAME/KEY: MISC_FEATURE
<222> LOCATION: (3)..(3)
<223> OTHER INFORMATION: bromine substituted at position 3 of the ring
<220> FEATURE:
<221> NAME/KEY: MISC_FEATURE
<222> LOCATION: (5)..(5)
<223> OTHER INFORMATION: bromine substituted at position 3 of the ring
<220> FEATURE:
<221> NAME/KEY: MISC_FEATURE
<222> LOCATION: (6)..(6)
<223> OTHER INFORMATION: NH2 substituted

<400> SEQUENCE: 39

Phe Gln Phe Gln Phe Lys
1               5

<210> SEQ ID NO 40
<211> LENGTH: 6
<212> TYPE: PRT
<213> ORGANISM: Artificial Sequence
<220> FEATURE:
<223> OTHER INFORMATION: synthetit peptide
<220> FEATURE:
<221> NAME/KEY: MISC_FEATURE
<222> LOCATION: (3)..(3)
<223> OTHER INFORMATION: bromine substituted at position 3 of the ring
<220> FEATURE:
<221> NAME/KEY: MISC_FEATURE
<222> LOCATION: (6)..(6)
<223> OTHER INFORMATION: NH2 substituted

<400> SEQUENCE: 40

Phe Gln Phe Gln Phe Lys
```

```
<210> SEQ ID NO 41
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: bromine substituted at position 4 of the ring
<220> FEATURE:
<221> NAME/KEY: MISC_FEATURE
<222> LOCATION: (3)..(3)
<223> OTHER INFORMATION: bromine substituted at position 4 of the ring
<220> FEATURE:
<221> NAME/KEY: MISC_FEATURE
<222> LOCATION: (5)..(5)
<223> OTHER INFORMATION: bromine substituted at position 4 of the ring
<220> FEATURE:
<221> NAME/KEY: MISC_FEATURE
<222> LOCATION: (6)..(6)
<223> OTHER INFORMATION: NH2 substituted

<400> SEQUENCE: 41

Phe Gln Phe Gln Phe Lys
1               5

<210> SEQ ID NO 42
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: Iodine substituted at position 3 of the ring
<220> FEATURE:
<221> NAME/KEY: MISC_FEATURE
<222> LOCATION: (6)..(6)
<223> OTHER INFORMATION: NH2 substituted

<400> SEQUENCE: 42

Phe Gln Phe Gln Phe Lys
1               5

<210> SEQ ID NO 43
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: Iodine substituted at position 3 of the ring
<220> FEATURE:
<221> NAME/KEY: MISC_FEATURE
<222> LOCATION: (5)..(5)
<223> OTHER INFORMATION: Iodine substituted at position 3 of the ring
<220> FEATURE:
<221> NAME/KEY: MISC_FEATURE
<222> LOCATION: (6)..(6)
<223> OTHER INFORMATION: NH2 substituted

<400> SEQUENCE: 43

Phe Gln Phe Gln Phe Lys
1               5

<210> SEQ ID NO 44
```

```
<211> LENGTH: 9
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X=2',6'-dimethyl-L-tyrosine
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (9)..(9)
<223> OTHER INFORMATION: NH2 substituted

<400> SEQUENCE: 44

Xaa Arg Phe Phe Glu Phe Gln Phe Lys
1               5

<210> SEQ ID NO 45
<211> LENGTH: 10
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X=2',6'-dimethyl-L-tyrosine
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (10)..(10)
<223> OTHER INFORMATION: NH2 substituted

<400> SEQUENCE: 45

Xaa Arg Phe Phe Lys Phe Gln Phe Glu Phe
1               5                   10

<210> SEQ ID NO 46
<211> LENGTH: 10
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X=2',6'-dimethyl-L-tyrosine
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (5)..(5)
<223> OTHER INFORMATION: D-isomer
<220> FEATURE:
<221> NAME/KEY: MISC_FEATURE
<222> LOCATION: (6)..(6)
<223> OTHER INFORMATION: D-isomer
<220> FEATURE:
<221> NAME/KEY: MISC_FEATURE
<222> LOCATION: (7)..(7)
<223> OTHER INFORMATION: D-isomer
<220> FEATURE:
<221> NAME/KEY: MISC_FEATURE
<222> LOCATION: (8)..(8)
<223> OTHER INFORMATION: D-isomer
```

```
<220> FEATURE:
<221> NAME/KEY: MISC_FEATURE
<222> LOCATION: (9)..(9)
<223> OTHER INFORMATION: D-isomer
<220> FEATURE:
<221> NAME/KEY: MISC_FEATURE
<222> LOCATION: (10)..(10)
<223> OTHER INFORMATION: D-isomer
<220> FEATURE:
<221> NAME/KEY: MISC_FEATURE
<222> LOCATION: (10)..(10)
<223> OTHER INFORMATION: NH2 substituted

<400> SEQUENCE: 46

Xaa Arg Phe Phe Lys Phe Gln Phe Glu Phe
1               5                   10

<210> SEQ ID NO 47
<211> LENGTH: 9
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X=2',6'-dimethyl-L-tyrosine
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (9)..(9)
<223> OTHER INFORMATION: NH2 substituted

<400> SEQUENCE: 47

Xaa Arg Phe Phe Glu Trp Gln Trp Lys
1               5

<210> SEQ ID NO 48
<211> LENGTH: 9
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X=2',6'-dimethyl-L-tyrosine
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (9)..(9)
<223> OTHER INFORMATION: NH2 substituted

<400> SEQUENCE: 48

Xaa Lys Phe Phe Gln Phe Gln Phe Lys
1               5

<210> SEQ ID NO 49
<211> LENGTH: 10
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X=2',6'-dimethyl-L-tyrosine
```

<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (6)..(6)
<223> OTHER INFORMATION: beta-3-homoPhe
<220> FEATURE:
<221> NAME/KEY: MISC_FEATURE
<222> LOCATION: (10)..(10)
<223> OTHER INFORMATION: NH2 substituted

<400> SEQUENCE: 49

Xaa Arg Phe Phe Gln Phe Phe Gln Phe Lys
1               5                   10

<210> SEQ ID NO 50
<211> LENGTH: 12
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X=2',6'-dimethyl-L-tyrosine
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (8)..(8)
<223> OTHER INFORMATION: beta-3-homoPhe
<220> FEATURE:
<221> NAME/KEY: MISC_FEATURE
<222> LOCATION: (12)..(12)
<223> OTHER INFORMATION: NH2 substituted

<400> SEQUENCE: 50

Xaa Arg Phe Phe Gly Gly Gln Phe Phe Gln Phe Lys
1               5                   10

<210> SEQ ID NO 51
<211> LENGTH: 9
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (9)..(9)
<223> OTHER INFORMATION: NH2 substituted

<400> SEQUENCE: 51

Tyr Arg Phe Phe Gln Phe Gln Phe Lys
1               5

<210> SEQ ID NO 52
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: D-isomer

```
<220> FEATURE:
<221> NAME/KEY: MISC_FEATURE
<222> LOCATION: (15)..(15)
<223> OTHER INFORMATION: NH2 substituted

<400> SEQUENCE: 52

Tyr Arg Phe Phe Gln Phe Gln Phe Lys Phe Gln Phe Gln Phe Lys
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X=2',6'-dimethyl-L-tyrosine
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (15)..(15)
<223> OTHER INFORMATION: NH2 substituted

<400> SEQUENCE: 53

Xaa Arg Phe Phe Gln Phe Gln Phe Lys Phe Gln Phe Gln Phe Lys
1               5                   10                  15

<210> SEQ ID NO 54
<211> LENGTH: 10
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X=2',6'-dimethyl-L-tyrosine
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (10)..(10)
<223> OTHER INFORMATION: NH2 substituted

<400> SEQUENCE: 54

Xaa Arg Phe Phe Trp Gln Trp Gln Trp Lys
1               5                   10

<210> SEQ ID NO 55
<211> LENGTH: 9
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X=2',6'-dimethyl-L-tyrosine
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (9)..(9)
<223> OTHER INFORMATION: NH2 substituted
```

```
<400> SEQUENCE: 55

Xaa Arg Trp Trp Gln Trp Gln Trp Lys
1               5

<210> SEQ ID NO 56
<211> LENGTH: 10
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (6)..(6)
<223> OTHER INFORMATION: beta-3-homoPhe
<220> FEATURE:
<221> NAME/KEY: MISC_FEATURE
<222> LOCATION: (10)..(10)
<223> OTHER INFORMATION: NH2 substituted

<400> SEQUENCE: 56

Tyr Arg Phe Phe Gln Phe Phe Gln Phe Lys
1               5                   10

<210> SEQ ID NO 57
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X=2',6'-dimethyl-L-tyrosine
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (4)..(4)
<223> OTHER INFORMATION: NH2 substituted

<400> SEQUENCE: 57

Xaa Lys Phe Phe
1

<210> SEQ ID NO 58
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X=2',6'-dimethyl-L-tyrosine
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (4)..(4)
<223> OTHER INFORMATION: NH2 substituted
```

```
<400> SEQUENCE: 58

Xaa Arg Phe Phe
1
```

HYDROGEL-FORMING COMPOSITION FOR CONTROLLED RELEASE

TECHNICAL FIELD

The present invention is situated in the field of hydrogels formed by defined peptides. More particularly, the invention provides hydrogel-forming compositions which comprise or can be loaded with active ingredients or biological materials and release said active ingredients or biological materials under physiological conditions in a controlled manner.

BACKGROUND OF THE INVENTION

When administered orally or via another non-parenteral route many bioactive ingredients suffer from a poor pharmacokinetic profile due to fast elimination and metabolisation. Parenteral administration methods therefore are often the only option available. However multiple daily injections are often required in order to maintain steady-state supply of bioactive ingredients. This not only is cumbersome but also negatively impacts patient compliance. A solution to increase patient compliance is by reducing the number of injections to one per day, week or month by the use of controlled-drug delivery vehicles.

One option to achieve this goal is the incorporation of the bioactive ingredients into a hydrogel. Hydrogels are defined as three-dimensional physical or covalently cross-linked networks that are able to absorb a large amount of water while maintaining a semisolid morphology. The networks in hydrogels are able to retain up to 99.99% water making them very interesting candidates for carrying active ingredients and biomaterials. The hydrogel network can encapsulate and release therapeutics via various mechanisms, such as (de) swelling, external triggers such as pH or temperature, erosion, or diffusion. Hydrogel matrices moreover possess the capability to encapsulate and release therapeutics in a sustained manner over prolonged periods of time.

For biomedical applications, like tissue engineering, medical imaging or controlled drug delivery, the predominant class under investigation still remains the family of chemical hydrogels in which the polymeric network is held together by cross-links formed by chemical bonds. However, for in vivo applications these polymeric cross-linked structures often lack important requirements like stability in biological fluids, low toxicity and poor immunogenicity, especially when crosslinking is done in vivo.

Hydrogels prepared from cross-linked synthetic polymers possess various disadvantages such as (i) monomer and degradation product toxicity (e.g. toxic cross-linkers, like gluteraldehyde or local acidification due to degradation products of PLGA and analogues), (ii) in vivo uncontrollable polymer swelling can cause pain in the host, (iii) non-uniform polymers possess different pore sizes and concomitant different release properties, and (iv) unwanted burst effects and release of active ingredient over brief periods of time due to large pores in the polymer network. In addition most synthetic (chemically cross-linked) polymers can only be administered via minor surgery. Biopolymers such as collagen, gelatin and fibrin on the other hand do not possess clinical human applications due to their origin and the risk of inflammatory host response from viruses or bacteria.

To cope with the problems associated with hydrogels based on synthetic polymers, self-assembling peptide hydrogels have been developed as suitable alternatives to synthetic polymer hydrogels. Peptide based hydrogels are formed by molecular self-assembly of the native peptides to nanoscale fibers. Self-assembling peptide hydrogels offer interesting properties, such as shear-thinning, lack of in vivo toxicity and immunogenicity, good biocompatibility and biodegradability, making them fit for in vivo use with applications in the field of drug delivery and tissue engineering. The peptides can be readily prepared using standard peptide synthesis methods and by selection of the amino acid building blocks the amino acid sequence can be conveniently customized to tunable mechanical and release properties.

Various a-peptide sequences have been described as having hydrogel-forming properties under physiological conditions. Most of these possess an amphipathic structure wherein the peptide sequence either consists of alternating hydrophobic and hydrophilic amino acids or contains a large hydrophobic end-group such as Fmoc.

Challenges in developing hydrogel-forming peptides are the selection of appropriate amino acids from the great diversity of available residues, their proneness to degradation by proteolytic enzymes, as well as the need to provide biocompatible, biodegradable and functional soft materials. A balance between hydrophobicity and hydrophilicity needs to be maintained when designing oligopeptide hydrogels in order to obtain a self-assembled system under suitable conditions. However, upon use of oligopeptide hydrogels as injectable controlled-delivery systems, challenges with regard to manufacturability, pH, drug release rate, mechanism of release, determination of toxicity, fine-tuning of viscoelastic and release properties and assessing its biological stability still need to be addressed.

A growing area of interest for peptide hydrogels is that of tissue engineering, which involves the use of living cells as building blocks to repair or replace portions of or whole tissues, e.g. bone, cartilage, blood vessels, bladder, skin, muscle, etc. Cells are typically implanted or 'seeded' into an artificial structure capable of supporting three-dimensional tissue formation. These structures, called scaffolds, serve as support while mimicking the in vivo environment of the cells. Scaffolds can be made of different materials, which can be of natural or synthetic sources and can be biodegradable or not. Examples of natural materials include collagen and fibrin, and polysaccharidic materials, like chitosan or glycosaminoglycans (GAGs), while synthetic materials include biodegradable polyesters such as PLGA and its analogues. Hydrogel based scaffolds have been developed of which peptide based hydrogels have gained particular interest because of the properties mentioned above and in particular their good cell compatibility.

Journal of Materials Chemistry B, 2015, 3, 759-765 describes an a-amino acid hexapeptide hydrogelator for controlled-release drug delivery. Angew. Chem. Int. Ed. 2013, 32, 8266-8270 reports 14-helical N-Acetyl-capped 13-peptides, which lead to supramolecular self-assembly resulting in nano- to macroscale fiber formation. Int. J. of Biological Macro. 2005, 36, 232-240 describes peptides with alternating hydrophobic and hydrophilic amino acids that form stable 13-sheet secondary structures and self-assemble into hydrogel-like matrices in the presence of physiological salt concentrations.

WO 2013/072686 describes self-assembling peptides a-amino acids that coalesce such that they self-assemble to form a hydrogel. US 2005/0181973 discloses self-assembling peptides of two-amino acid domains for use as scaffolds in cell culture, tissue engineering and tissue repair.

US2014/0302144 discloses pharmaceutical formulations comprising self-assembling peptides for sustained delivery of therapeutic agents.

Although the current hydrogels for controlled release offer attractive properties there still is room for improvement in particular as regards to their mechanical, biological and chemical properties such as pH, biocompatibility, improved immunogenicity and toxicity profile, as well as drug delivery characteristics. Furthermore, when aiming at a competitive technology, which is accessible for most patients, the manufacturing of the hydrogel requires optimization.

SUMMARY

The invention provides amphipathic hydrogelator peptides and corresponding hydrogels produced therefrom, that can be used as a drug repository or controlled release composition or as a scaffold for biological molecules or macromolecular complexes such as cells.

More specifically, the hydrogels (e.g. co-formulations and biogels) as described herein can be used for controlled release of pain medication (e.g. opioids). To achieve sustained pain relief, it is necessary to develop proper drug delivery systems which can maintain a constant therapeutic effect without fluctuations in the physiological response. Although classic oral medication prescriptions appear to be the first choice (i.e. earliest and least invasive administration mode), the limited duration of action due to first-pass metabolism of the drug represents a drawback for long treatments. The hydrogels according to present invention provide a controlled and slow drug release. Hence, said hydrogels offer a large advantage over pain medication delivered via the oral route.

Furthermore, if the hydrogels according to present invention comprising the described opioid peptides as a biologically active ingredient would be administered orally, the opioid peptide would not be absorbed systemically. Hence, the opioid peptide would not be able exert its antinociceptive effect. Therefore, it is very likely that the hydrogels according to present invention will decrease the abuse and tampering of opioids.

Earlier publications have experimented with specific examples of peptide hydrogels in vitro (Bibian et al., J. Mater. Chem. B., 2015). The effective release of the biologically active ingredient from a hydrogel or biogel in vitro is however not a predictive factor for the success of the release of the biologically active ingredient in vivo. Moreover, non-cytotoxicity and the ability to re-gelate after subcutaneous injection are crucial for in vivo use of a hydrogel or biogel and should be evaluated on an individual basis. Since Bibian et al. did not disclose any results on re-gelation or cytotoxicity, one cannot not simply assume that the hydrogels described with promising release properties in vitro would also be suitable for in vivo applications.

The invention generally provides the following aspects:
Aspect 1: A hydrogel-forming composition for controlled release of a biologically active ingredient and/or biological material, comprising:
(a) an amphipathic peptide hydrogelator comprising at least 4 and at most 16 amino acid residues; and
(b) one or more biologically active ingredients and/or biological materials.
Aspect 2: The hydrogel-forming composition according to aspect 1, wherein the biologically active ingredient is selected from the group comprising: small molecules, synthetic or natural active ingredients such as monosaccharides, disaccharides, trisaccharides, oligosaccharides, peptides, nucleic acids, nucleic acid analogues and derivatives, plasmids, vectors, polysaccharides, polypeptides, proteins, peptide analogues, peptidomimetics, antibodies, nanobodies, antibody fragments, nucleic acid based molecules (e.g. DNA, RNA, mRNA, tRNA, RNAi, siRNA, microRNA, or any other DNA or RNA-like molecules), polynucleotides, oligonucleotides, enzymes, antibiotics, antifungal agents, antiviral agents, anti-inflammatory agents, growth stimulating or inhibiting agents, blood clotting or coagulation factors, immunomodulators, natural ligands, immunoglobulins, extracts made from biological materials such as bacteria, plants, fungi, or animal cells or tissues, therapeutic agents, preventatives, diagnostic agents, imaging agents, aptamers and derivatives thereof.
Aspect 3: The hydrogel-forming composition according to aspect 1 or 2, wherein the hydrogel-forming composition is a co-formulation, i.e. a mixture of hydrogelator peptides and active ingredients and/or biological materials.
Aspect 4: The hydrogel-forming composition according to aspect 3, wherein the amphipathic peptide hydrogelator is a peptide comprising between 4 and 16 amino acids, comprising the following sequence:

$(X—Y)n$, $(X—Y)n$-X, $(Y—X)n$ or $(Y—X)n$-Y,
wherein
(i) n is an integer from 2-8,
(ii) wherein X is a hydrophobic amino acid and Y is a hydrophilic amino acid,
(iii) wherein the N-terminus and C-terminus can be independently substituted with respectively Ra and Rb, and preferably
(iv) wherein the amphipathic peptide hydrogelator comprises a C-terminal amide.
Aspect 5: The hydrogel-forming composition according to aspect 4, wherein the amphipathic peptide hydrogelator is a peptide wherein the N-terminus of the hydrogel-forming peptide bears one or two Ra groups each independently selected from $R^1$, or bears one $R^1$ group and one group selected from $C(=Z)R1$, $C(=Z)ZR1$, $C(=Z)NHR^1$ and $C(=Z)N(R^1)2$;
wherein each Z independently is O or S;
wherein each $R^1$ is independently selected from H, an optionally substituted linear or branched $C_{1-10}$alkyl, an optionally substituted $C_{3-10}$cycloalkyl, an optionally substituted aryl$C_{1-6}$alkyl and an optionally substituted aryl; and/or
wherein the C-terminus of the hydrogel-forming peptide bears a Rb group selected from $OR^2$ or $N(R^2)2$: wherein each $R^2$ independently is selected from H, an optionally substituted linear or branched $C_{1-10}$alkyl, an optionally substituted $C_{3-10}$cycloalkyl, an optionally substituted aryl$C_{1-6}$alkyl, and an optionally substituted aryl; or a salt form thereof.
Aspect 6: The hydrogel-forming composition according to any one of aspects 3 to 5, wherein the amphipathic peptide hydrogelator is a hexapeptide.
Aspect 7: The hydrogel-forming composition according to any one of aspects 3 to 6, wherein the hydrophobic amino acid(s) are selected from the group consisting of: Phe, Trp, Tyr, Ala, Val, Leu, Iie, Met, Pro and Gly and wherein the hydrophilic amino acid(s) are selected from the group consisting of: Gin, Glu, Asn, Ser, Thr, Cys, Arg, His, Lys, Asp and Gly.

Aspect 8: The hydrogel-forming composition according to any one of aspects 3 to 7, wherein the amphipathic peptide hydrogelator has an amino acid sequence according to any one of SEQ ID NOs: 1 to 26 and 37 to 43, preferably any one of SEQ ID NOs: 1, 2, 4, 5, 9, 10, 11, 12, 13, 14, 15, 16, 17, 18, 19, 20, 21, 22, 23, 24, 25 or 26 (cf. table 1 below), or the salt-forms thereof, preferably the trifluoroacetic salts, sodium chloride salts or acetic acid salts. In some embodiments, the peptide sequences as shown in Table 1 below can additionally include a 13-(homo)-amino acid such as e.g. a $13^3$-homo-Phe, $13^3$-homo-Trp or $13^3$-homo-Tyr which is coupled in front of the original Phe, Trp or Tyr residue respectively present in said sequence, as exemplified in Table 3 below.

Aspect 9: The hydrogel-forming composition according to any one of aspects 3 to 8, wherein the amphipathic peptide hydrogelator has the amino acid sequence according to SEQ ID NO: 18 or the salt-forms thereof, preferably the trifluoroacetic salts, sodium chloride salts or acetic acid salts.

Aspect 10: The hydrogel-forming composition according to any one of aspects 3 to 9, wherein the resulting hydrogel has a pH of at least 4, preferably ranging from 4 to about 8, preferably ranging from 6 to about 8, most preferably of 7.4.

Aspect 11: The hydrogel-forming composition according to aspect 1 or 2, wherein the hydrogel-forming composition is a biogel composition, wherein the amphipathic peptide hydrogelator is bound to the active ingredient, optionally through a linker.

Aspect 12: The hydrogel-forming composition according to aspect 11, wherein the biologically active ingredient is a peptide or a protein, preferably selected from the group comprising: synthetic or natural peptides, biological macromolecules, polypeptides, proteins, peptide analogues, peptidomimetics and antibodies, nanobodies, antibody fragments and derivatives thereof.

Aspect 13: The hydrogel-forming composition according to aspect 11 or 12, wherein the biologically active ingredient is a drug used for pain relief, preferably selected from the group comprising opioids and opioid peptides, non-peptidic opioid analogues, non-opioid analgesics, antidepressants, anticonvulsants.

Aspect 14: The hydrogel-forming composition according to any one of aspects 11 to 13, wherein said linker is covalent.

Aspect 15: The hydrogel-forming composition according to any one of aspects 11 to 14, wherein said linker is chosen from the list comprising: amide, peptide bond, ester, carbonate, carbamate, glycoside, acetal, disulfide, hydrazone, tert-butyloxycarbonyl, paramethoxybenzyl, dialkyl, diaryldialkoxysilane, orthoester, 13-thiopropionate, ketal, phosphoramidate, vinyl ether, imine, aconityl, trityl, polyketal and azo.

Aspect 16: The hydrogel-forming composition according to any one of aspects 11 to 15, wherein the hydrogel-forming composition is a peptide, preferably a biodegradable peptide.

Aspect 17: The hydrogel-forming composition according to any one of aspects 11 to 16, wherein the amphipathic peptide hydrogelator is a peptide comprising between 4 and 16 amino acids, comprising the following sequence:

(X—Y)$n$, (X—Y)$n$(X), (Y—X)$n$, (Y—X)$n$(Y), wherein (i) n is an integer from 2-8,
(ii) X is a hydrophobic amino acid and Y is a hydrophilic amino acid,
(iii) the N-terminus and C-terminus can be independently substituted with respectively Ra and Rb as defined herein, and
(iv) the amphipathic peptide hydrogelator preferably comprises a C-terminal amide.

Aspect 18: The hydrogel-forming composition according to any one of aspects 11 to 17, wherein the amphipathic peptide hydrogelator is a hexapeptide.

Aspect 19: The hydrogel-forming composition according to any one of aspects 11 to 18, wherein the hydrophobic amino acid(s) are selected from the group consisting of: Phe, Trp, Tyr, Ala, Val, Leu, Iie, Met, Pro and Gly and wherein the hydrophilic amino acid(s) are selected from the group consisting of: Gln, Glu, Asn, Ser, Thr, Cys, Arg, His, Lys, Asp and Gly.

Aspect 20: The hydrogel-forming composition according to any one of aspects 11 to 19, wherein the amphipathic peptide hydrogelator has an amino acid sequence according to any one of SEQ ID NOs: 1 to 26, preferably any one of SEQ ID NOs: 1, 2, 4, 5, 9, 10, 11, 12, 13, 14, 15, 16, 17, 18, 19, 20, 21, 22, 23, 24, 25 or 26 (cf. Table 1 below). In some embodiments, the amphipathic peptide hydrogelator sequences as shown in Table 1 below can additionally include a 13-(homo) amino acid such as e.g. a $13^3$-homo-Phe, $13^3$-homo-Trp or $13^3$-homo-Tyr which is coupled in front of the original Phe, Trp or Tyr residue respectively present in said sequence, as exemplified in Table 3 below. In some embodiments, the amphipathic peptide hydrogelator sequences as shown in Table 1 below can additionally include one or more halogenated hydrophobic amino acid residues, such as e.g. phenylalanine, tyrosine or tryptophan comprising a Bromine, Iodine, Chlorine or Fluorine coupled to their ring, as exemplified in any one of SEQ ID NOs: 37, 38, 39, 40, 41, 42 or 43. In some embodiments, particularly when the amphipathic peptide hydrogelator of the hydrogel-forming composition comprises unnatural amino acids such as 13-(homo) amino acids or halogenated amino acids, the peptide in said hydrogel-forming composition can also comprise a linker e.g. as defined in aspect 15, between the amphipathic peptide hydrogelator and the bioactive peptide.

Aspect 21: The hydrogel-forming composition according to any one of aspects 11 to 20, wherein the resulting biogel has a pH of at least 4, preferably ranging from 4 to about 8, preferably ranging from 6 to about 8, most preferably of 7.4.

Aspect 22: The hydrogel-forming composition according to any one of aspects 11 to 21, wherein the amphipathic peptide hydrogelator comprises a C-terminal amide.

Aspect 23: The hydrogel-forming composition according to any one of aspects 11 to 22, wherein the amphipathic peptide hydrogelator has an amino acid sequence according to SEQ ID NO: 16, or the salt-forms thereof, preferably the trifluoroacetic salts, sodium chloride salts or acetic acid salts.

Aspect 24: The hydrogel-forming composition according to any one of aspects 11 to 23, wherein the hydrogel-forming composition is a peptide with an amino acid sequence according to any one of SEQ ID NOs: 27, 28, 29, 30, 31, 32, or 44 to 56, preferably SEQ ID NO: 30 or 48 (cf. Table 2). In some embodiments, the peptide sequences as shown in Table 2 below can additionally include a β-(homo) amino acid such as e.g. a β³-homo-Phe, β³-homo-Trp or β³-homo-Tyr, which is coupled in front of the original Phe, Trp or Tyr residue respectively present in said sequence. In some embodiments, the amphipathic peptide hydrogelator sequences as shown in Table 2 below can additionally include one or more halogenated hydrophobic amino acid residues, such as e.g. phenylalanine, tyrosine or tryptophan comprising a Bromine, Iodine, Chlorine or Fluorine coupled to their ring. In some embodiments, the peptide in said hydrogel-forming composition can also comprise a linker e.g. as defined in aspect 15, between the amphipathic peptide hydrogelator and the bioactive peptide.

Aspect 25. The hydrogel-forming composition according to any one of aspects 1 to 24,
wherein the amphipathic peptide hydrogelator comprises a dyad formed by a β-(homo) amino-acid and an alpha-amino acid.

Aspect 26. The hydrogel-forming composition according to aspect 25, wherein the hydrogel-forming composition is a peptide with an amino acid sequence according to SEQ ID NO: 33, 34, 35, or 36, preferably 33.

Aspect 27: The hydrogel-forming composition according to any one of aspects 1 to 26, for use in medicine.

Aspect 28: Use of the hydrogel-forming composition according to any one of aspects 1 to 26 for the production of a medicament for use in medicine.

Aspect 29: The hydrogel-forming composition according to any one of aspects 1 to 26 for use in a medical application chosen from the list comprising drug delivery systems, tissue engineering, tissue repair, regenerative medicine, diagnostics, wound dressing, separation of biomolecules or cells, barrier materials to regulate biological adhesion and biosensor; preferably drug delivery systems.

Aspect 30: Use of the hydrogel-forming composition according to any one of aspects 1 to 26 in a medical application chosen from the list comprising drug delivery systems, tissue engineering, tissue repair, regenerative medicine, diagnostics, wound dressing, separation of biomolecules or cells, barrier materials to regulate biological adhesion and biosensor; preferably drug delivery systems.

Aspect 31: The hydrogel-forming composition according to any one of aspects 1 to 26 for use in personal care applications chosen from the list comprising pharmaceuticals, dietary supplements, consumer products used in personal hygiene and/or beautification, cosmeceuticals and cosmetics.

Aspect 32: Use of the hydrogel-forming composition according to any one of aspects 1 to 26 in personal care applications chosen from the list comprising pharmaceuticals, dietary supplements, consumer products used in personal hygiene and/or beautification, cosmeceuticals and cosmetics.

Aspect 33: The hydrogel-forming composition according to any one of aspects 1 to 26 for use in cosmetics chosen from the list comprising skin moisturizers, perfumes, lipsticks, fingernail polishes, eye and facial makeup preparations, shampoos, permanent waves, hair colors, toothpastes, and deodorants.

Aspect 34: Use of the hydrogel-forming composition according to any one of aspects 1 to 26 in cosmetics chosen from the list comprising skin moisturizers, perfumes, lipsticks, fingernail polishes, eye and facial makeup preparations, shampoos, permanent waves, hair colors, toothpastes, and deodorants.

Aspect 35: The hydrogel-forming composition according to any one of aspects 1 to 26 for use in controlled release of one or more biologically active ingredient(s).

Aspect 36: Use of the hydrogel-forming composition according to according to any one of aspects 1 to 26 for the controlled release of one or more biologically active ingredient(s).

Aspect 37: Use of the hydrogel-forming composition according to any one of aspects 1 to 26 as a matrix/scaffold suitable for 2D or 3D in vitro cell culture, tissue engineering and/or tissue repair.

Aspect 38: A method of treating acute, chronic and/or neuropathic pain by administering the hydrogel-forming composition according to any of aspects 1 to 26.

Aspect 39: The hydrogel-forming composition according to any one of aspects 1 to 26 for use in the treatment of acute, chronic and/or neuropathic pain.

Aspect 40: Use of the hydrogel-forming composition according to any one of aspects 1 to 26 in the treatment of acute, chronic and/or neuropathic pain.

Aspect 41: A method for producing a hydrogel-forming composition according to any one of aspects 1 to 26, comprises the steps of:
(a) synthesizing and purifying a hydrogel-forming peptide
(b) mixing said hydrogel-forming peptide with one or more biologically active ingredient(s), or coupling said hydrogel-forming peptide to one or more biologically active ingredient(s), and
(c) contacting said hydrogel-forming composition obtained in (b) with an aqueous medium and allowing the formation of the hydrogel to take place.

Aspect 42: The method according to aspect 41, wherein step (c) is performed in phosphate buffered saline (PBS), saline solution, water, or a combination thereof, preferably at a concentration of at least 2 and at most 20 mM, more preferably at least 5 and at most 15 mM, most preferably 10 mM, optionally supplemented with NaOH.

Aspect 43: The method according to aspect 41 or 42, wherein the method is performed at a pH ranging from about 3 to about 11, preferably from about 4 to about 8, more preferably at physiological conditions, most preferably at a pH of 7.4.

Aspect 44: A method for producing a hydrogel-forming composition according to any one of aspects 3 to 10, 25, or 26, comprising the steps of:
(a) synthesizing and purifying the amphipathic peptide hydrogelator, optionally followed by salt exchange,
(b) dissolving one or more biologically active ingredient(s) or biological material in an aqueous medium containing a buffer,
(c) contacting said aqueous medium containing one or more biologically active ingredient(s) and/or biological material of (b) with the peptide obtained in (a) and allowing the formation of the co-formulation to take place.

Aspect 45: A method for producing a hydrogel-forming composition according to any one of aspects 10 to 25, comprising the steps of:
(a) synthesizing and purifying the amphipathic peptide hydrogelator, optionally followed by salt exchange,
(b) coupling the peptide obtained in (a) with one or more biologically active ingredient(s), optionally via a linker, thereby forming a complex, (c) dissolving the complex formed in (b) in an aqueous medium containing a buffer and allowing the formation of a biogel composition to take place.

Aspect 46: A method for producing a hydrogel-forming composition according to any one of aspects 10 to 25, comprising the steps of:
(a) synthesizing and purifying the amphipathic peptide hydrogelator coupled to one or more biologically active ingredient(s), optionally followed by salt exchange,
(b) dissolving the complex formed in (a) in an aqueous medium containing a buffer and allowing the formation of a biogel composition to take place.

Aspect 47: The method for producing a hydrogel-forming composition according to aspect 45 or 46, wherein the biologically active ingredient is a peptide or a protein, preferably selected from the group comprising: synthetic or natural peptides, biological macromolecules, polypeptides, proteins, peptide analogues, peptidomimetics and antibodies, nanobodies, antibody fragments and derivatives thereof.

Aspect 48: A method of treating a medical condition in a subject with the hydrogel-forming composition according to any one of aspects 1 to 26, said subject preferably being in need of administration of any one or more of the active agents as identified herein in a controlled release manner.

Aspect 49: A method of treating acute, chronic and/or neuropathic pain in a subject with the hydrogel-forming composition according to any one of aspects 1 to 26, said subject preferably being in need of administration of one or more drugs used for pain relief, preferably selected from the group comprising opioids and opioid peptides, non-peptidic opioid analogues, non-opioid analgesics, antidepressants and anticonvulsants.

Aspect 50: The method according to aspect 48, wherein said medical condition is chosen from the list comprising: tissue engineering, tissue repair, regenerative medicine, or wound dressing, Aspect 51: The hydrogel-forming composition according to any one of aspects 1 to 26 present in or forming part of: a drug delivery system, a tissue engineering composition, a tissue repair composition, a composition for regenerative medicine, a diagnostic composition, a wound dressing system, a system for separation of biomolecules or cells, barrier materials for regulating biological adhesion or in a biosensor; preferably in a drug delivery system.

Aspect 52: The hydrogel-forming composition according to any one of aspects 1 to 26 present in or forming part of: personal care applications chosen such as pharmaceuticals, dietary supplements, consumer products used in personal hygiene and/or beautification, cosmeceuticals and cosmetics.

BRIEF DESCRIPTION OF THE FIGURES

FIG. 8 represents the plasma concentration of amphipathic peptide hydrogelator 2 as a function of time (semi Log). Samples were taken after 0, 5, 10, 15, 30, 60 and 90 minutes. The experiment was performed on three independent samples. The average result is plotted allowing to determine the equation which describe the degradation as a function of time as $y=-0.02024x+0.9611$ given an half-life of 14.71±0.15 min.

FIG. 9 represents the qualitative cytotoxicity determined using a two-color fluorescence cell viability assay that is based on the simultaneous determination of live and dead cells grown on ultra-low attachment (ULA) plates, plates coated with tissue culture polystyrene (TCPS), or coated with hydrogels formed by hydrogelator peptide 2 or 4. Scale bar calculation: 200 μm is represented as 16.3% of the width of the original image. Right panels of A, B and C (right) show predominantly green fluorescent cells (live cells), while D shows an evenly distributed number of red (dead cells) and green (live cells) fluorescent cells.

FIG. 11 represents the antinociceptive effects of morphine in the mouse tail-flick test after s.c. administration, applied in solution. Left panel: Time course of the antinociceptive response as % of Maximum Possible Effect (¾MPE). Doses of morphine are given per mouse. Data are the mean±SEM of 5 to 10 mice per group.

FIG. 22 represents the antinociceptive effects of peptide-based analgesics in co-formulation with hydrogelator peptide CM-63 (SEQ ID NO: 16) in the mouse tail-flick test after s.c. administration. (A) Time course of the antinociceptive response to opioid peptide CM-80-OP (SEQ ID NO: 58) co-formulated with a hydrogel of hydrogelator peptide CM-63 (SEQ ID NO: 16) or MBG-6 (SEQ ID NO: 2) as % of Maximum Possible Antinociceptive Effect (¾MPE); (B) time course of the antinociceptive response to opioid peptide EO-CM-OP (SEQ ID NO: 57) co-formulated with a hydrogel of hydrogelator peptide CM-63 (SEQ ID NO: 16) as % of Maximum Possible Antinociceptive Effect (3/MPE); (C) time course of the antinociceptive response to opioid peptide KGOP01 (SEQ ID NO: 59) co-formulated with a hydrogel of hydrogelator peptide CM-63 (SEQ ID NO: 16) as % of Maximum Possible Antinociceptive Effect (¾MPE) KGOP01 in co-formulation with the hydrogel CM-63, in the mouse tail-flick test after s.c. administration.

FIG. 23 represents the process of degradation of biogels CM-58 (SEQ ID NO: 31), CM-136 (SEQ ID NO: 48) and CM-137 (SEQ ID NO: 49).

FIG. 25 represents the structures of the three types of cargo used within example 9: small molecule 4-amino-2-cyclohexylmethyl-indolo[3,4-c]azepin-2-on 3, 15-residue peptide 4 and cAbVCAM1-5 Nb 5, covalently linked to a chelator holding the radioactive isotype $^{111}$In.

FIG. 26 represents the nuclear imaging of the in vivo release of a small molecule (A), a peptide (B) and a nanobody (C) from the injection site after s.c. injection. The three types of cargos were co-formulated within hydrogelator peptide 2 (SEQ ID NO: 2) (w/v¾ in PBS, upper half of images and full curves) or injected in solution as control (lower half of images and dotted curves).

FIG. 29 represents the preferred sequences of the hydrogelators that form a gel are listed below. The grey circles represent hydrophobic a (D or L) amino acids and the open circles represent hydrophilic (charged or non-charged) a (D or L) amino acids.

DETAILED DESCRIPTION OF THE INVENTION

Figure 1:
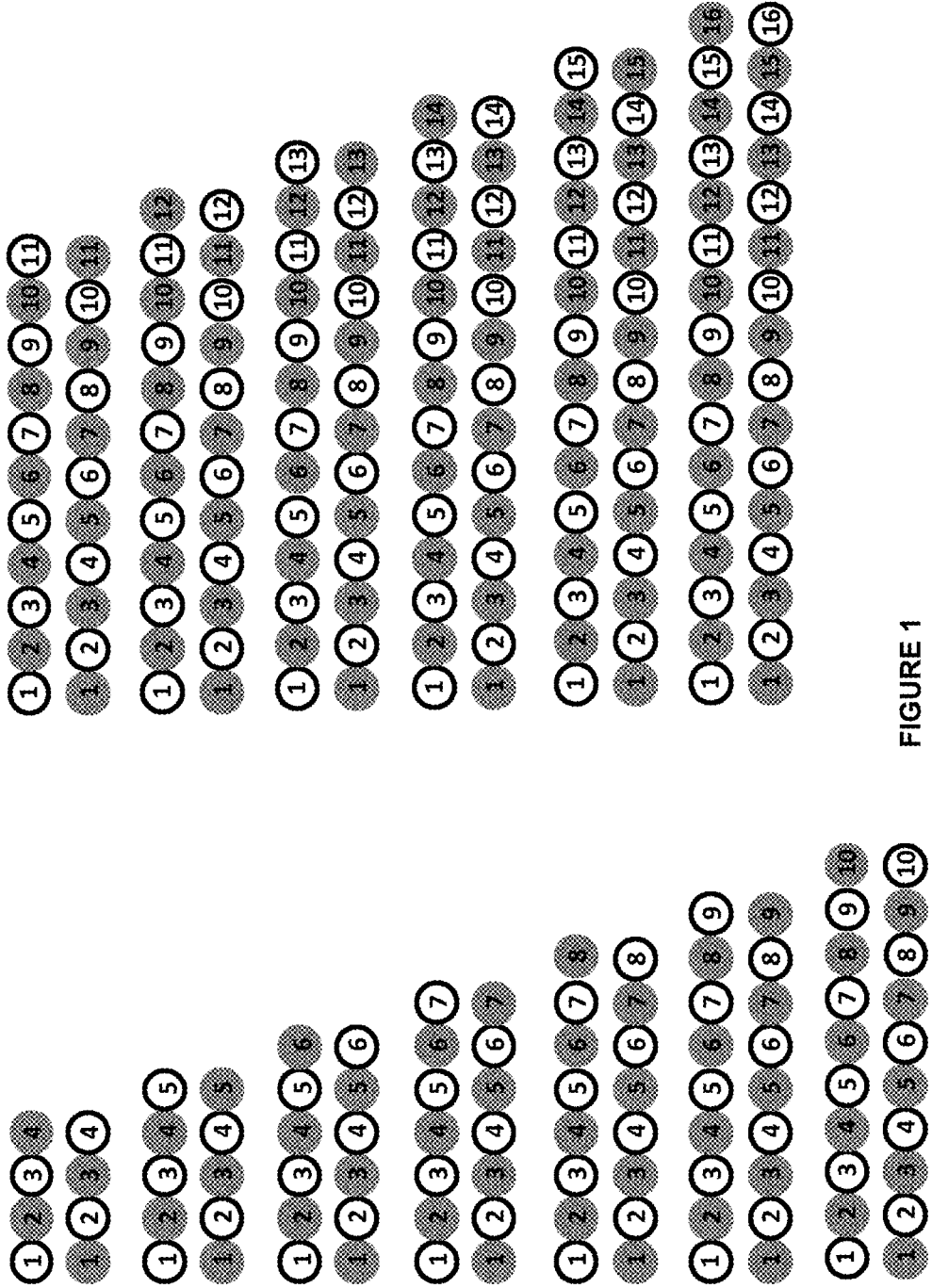
FIG. 1 represents a scheme for the amino acid sequences of the amphipathic hydrogelator peptide.

Before the present hydrogel-forming compositions, the hydrogels, methods of production and uses thereof in the invention are described, it is to be understood that this invention is not limited to particular hydrogel-forming compositions, hydrogels, methods of production and uses thereof, as described, as such hydrogel-forming compositions, hydrogels, methods of production and uses thereof may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms also encompass "consisting of" and "consisting essentially of".

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of and from the specified value, in particular variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Whereas the term "one or more", such as one or more members of a group of members, is clear per se, by means of further exemplification, the term encompasses inter alia a reference to any of said members, or to any two or more of said members, such as, e.g., any :::::3,:::::4,:::::5,:::::6 or :::::7 etc. of said members, and up to all said members.

All documents cited in the present specification are hereby incorporated by reference in their entirety.

Unless otherwise specified, all terms used in disclosing the invention, including technical and scientific terms, have the meaning as commonly understood by one of ordinary skill in the art to which this invention belongs. By means of further guidance, term definitions may be included to better appreciate the teaching of the present invention.

The present invention relates to hydrogel-forming compositions for controlled release of a biologically active ingredient and/or biological material, the uses thereof and their methods of production. Depending on the required dose, rate of diffusion, the concentration and the volume of the hydrogel-forming compositions can be adapted.

In a first aspect, the present invention relates to a hydrogel-forming composition for controlled release of a biologically active ingredient and/or biological material, comprising:
 (a) an amphipathic peptide hydrogelator comprising at least 4 and at most 16 amino acid residues; and
 (b) one or more biologically active ingredients and/or biological materials.

As used herein "peptide" refers to a short truncated protein generally comprising at least 2 naturally occurring or synthetic amino acids which can also be further modified including covalently linking the peptide bonds of the alpha carboxyl group of a first amino acid and the alpha amino group of a second amino acid by eliminating a molecule of water. The amino acids can be either those naturally occurring amino acids or chemically synthesized variants of such amino acids or modified forms of these amino acids which can be altered from their basic chemical structure by addition of other chemical groups which can be found to be covalently attached to them in naturally occurring compounds. In present invention, the term peptide can refer to the amphipathic peptide hydrogelator as well as to the biologically active ingredient, or to the combination thereof if both the hydrogelator and active ingredient comprise amino acids.

As used herein "protein" refers to a polypeptide made of amino acids arranged in a linear chain and joined together by peptide bonds between the carboxyl and amino groups of adjacent amino acid residues. Generally a protein is a large polypeptide such as a polypeptide comprising more than 30, more than 40 or more than 50 amino acids. Generally, a protein will have a secondary structure due to the folding of the polypeptide chain. As used herein, the term "hydrogelator" refers to a peptide that is capable of forming a hydrogel. The hydrogelator according to present invention is a peptide hydrogelator, more specifically an amphipathic peptide hydrogelator.

The term "hydrogel" as used herein, refers to a macromolecular polymer gel constructed of a network of cross-linked polymer chains. The net-like structure enhances the hydrogel's ability to absorb large amounts of water via hydrogen bonding. In present invention, the hydrogel is preferably self-assembling.

As used herein, the term "amphipathic" refers to the characteristic of possessing both a polar and a non-polar region and exhibiting both hydrophilic and hydrophobic properties. For example, a peptide of which the peptide sequence comprises alternating hydrophobic and hydrophilic amino acids is amphipathic.

In particular embodiments, the amphipathic peptide hydrogelator according to present invention comprising at least 4 and at most 16 amino acid residues, preferably at least 5 and at most 8 amino acid residues, most preferably 6 amino acid residues.

The biological stability, mechanical strength and release properties can be tuned by structural modifications in the amino acid sequence of the amphipathic peptide hydrogelator.

The peptide possesses tunable storage moduli and forms a transparent self-supporting gel with shear-thinning behavior. The amino acid residues of the peptide hydrogelator can be alpha-amino acid residues, (L- or D-optical isomers) or 13-amino acid residues, preferably L-a-amino acid residues or amino acid analogues. One or more amino acid residues in the amino acid sequence of the amphipathic peptide hydrogelator can be halogenated.

Preferably, when the peptide hydrogelator of the hydrogel-forming composition (e.g. biogel) comprises unnatural amino acids such as D-amino acids, 13-amino acids or halogenated amino acids, and/or has increased biological stability, the hydrogel-forming composition also comprises a linker as described elsewhere herein.

In particular embodiments, the amphipathic peptide hydrogelator comprises the following sequence: (X—Y)n, (X—Y)n(X), (Y—X)n, (Y—X)n(Y), wherein
(i) n is an integer from 2-8,
(ii) X is a hydrophobic amino acid and Y is a hydrophilic amino acid,
(iii) the N-terminus and C-terminus can be independently substituted with respectively Ra and Rb, and preferably
(iv) the amphipathic peptide hydrogelator comprises a C-terminal amide.

Possible amphipathic peptide hydrogelator sequences are (see FIG. 1):

```
Tetrapeptides: X-Y-X-Y or Y-X-Y-X

Pentapeptides: X-Y-X-Y-X or Y-X-Y-X-Y

Hexapeptides: X-Y-X-Y-X-Y or Y-X-Y-X-Y-X

Heptapeptides: X-Y-X-Y-X-Y-X or Y-X-Y-X-Y-X-Y

Octapeptides: X-Y-X-Y-X-Y-X-Y or Y-X-Y-X-Y-X-Y-X

Nonapeptides: X-Y-X-Y-X-Y-X-Y-X or Y-X-Y-X-Y-X-Y-
X-Y

Decapeptides: X-Y-X-Y-X-Y-X-Y-X-Y or Y-X-Y-X-Y-
X-Y-X

Undecapeptides: X-Y-X-Y-X-Y-X-Y-X-Y-X or Y-X-Y-X-Y-
X-Y-X-Y-X-Y

Dodecapeptides: X-Y-X-Y-X-Y-X-Y-X-Y-X-Y or Y-X-Y-X-
Y-X-Y-X-Y-X-Y-X

Tridecapeptides: X-Y-X-Y-X-Y-X-Y-X-Y-X-Y-X or Y-X-
Y-X-Y-X-Y-X-Y-X-Y-X-Y

Tetradecapeptides: X-Y-X-Y-X-Y-X-Y-X-Y-X-Y-X-Y or
Y-X-Y-X-Y-X-Y-X-Y-X-Y-X-Y-X

Pentadecapeptides: X-Y-X-Y-X-Y-X-Y-X-Y-X-Y-X-Y-X or
Y-X-Y-X-Y-X-Y-X-Y-X-Y-X-Y-X-Y Hexadecapeptides: X-Y-X-Y-X-Y-X-Y-X-Y-X-Y-X-Y-X-Y
or Y-X-Y-X-Y-X-Y-X-Y-X-Y-X-Y-X-Y-X
```

In each of said exemplary peptides, the N-terminus and C-terminus can be independently substituted with respectively Ra and Rb as defined herein.

In a particular embodiment, the hydrogel-forming composition is a peptide wherein the N-terminus of the hydrogel-forming peptide bears one or two Ra groups each independently selected from $R^1$, or bears one $R^1$ group and one group selected from C(=Z)$R^1$, C(=Z)Z$R1$, C(=Z)NH$R^1$ and C(=Z)N($R^1$)$_2$;
wherein each Z independently is O or S; wherein each $R^1$ is independently selected from H, an optionally substituted linear or branched $C_{1\_10}$alkyl, an optionally substituted $C_{3\_10}$cycloalkyl, an optionally substituted aryl$C_{1\_6}$ alkyl and an optionally substituted aryl; and wherein the C-terminus of the hydrogel-forming peptide bears a Rb group selected from O$R^2$ or N($R^2$)$_2$; wherein each $R^2$ independently is selected from H, an optionally substituted linear or branched $C_{1\_10}$alkyl, an optionally substituted $C_{3\_10}$cycloalkyl, an optionally substituted aryl$C_{1\_6}$ alkyl, and optionally substituted aryl; or a salt form thereof.

Whenever the term "substituted" as used herein, it is meant to indicate that one or more hydrogen atoms on the atom indicated in the expression using "substituted" is replaced with a selection from the indicated group, provided that the indicated atom's normal valence is not exceeded, and that the substitution results in a chemically stable compound, i.e. a compound that is sufficiently robust to survive isolation from a reaction mixture. In preferred embodiments, the substitute is halogen or methoxy group.

As used herein $C_{1\_10}$alkyl as a group or part of a group defines straight or branched chain saturated hydrocarbon groups having from 1 to 10 carbon atoms such as methyl, ethyl, 1-propyl, 2-propyl (iPr), 1-butyl, 2-methyl-1-propyl (i-Bu), 2-butyl (s-Bu), 2-dimethyl-2-propyl (t-Bu), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, pentyl and its isomers such as 2-methylbutyl, hexyl and its isomers such as 2-methylpentyl, heptyl and its isomers such as 2-methylhexyl, octyl, nonyl, decyl and their respective isomers, and the like.

Of interest amongst $C_{1\_10}$alkyl is $C_{1\_6}$alkyl, which is as specified above and has from 1 to 6 carbon atoms; of specific interest amongst $C_{1\_6}$alkyl is $C_{1\_4}$alkyl, which is as specified above and has from 1 to 4 carbon atoms; of interest amongst $C_{1\_4}$alkyl is methyl or ethyl.

$C_3$-$C_{10}$cycloalkyl defines cyclic and, where possible, bicyclic saturated hydrocarbon groups having from 3 to 10 carbon atoms such as, e.g., cyclopropyl, cyclobutyl, cyclopentyl, cyclohexyl, cycloheptyl, cyclooctyl, cyclononyl, cyclodecyl, decalinyl. In one embodiment C3-C10cycloalkyl is monocyclic C3-C7cycloalkyl.

$C_{1\_10}$alkyl and $C_3$-$C_{10}$ cycloalkyl groups may be optionally substituted with one or more, in particular with 1, 2 or 3, substituents, which each independently may be selected from $C_{1\_5}$alkyl, C3-C7cycloalkyl, halogen, C1_5alkoxy, hydroxyl, amino, mono- and di-C1_5alkyl amino, aryl, cyano, carboxyl, $C_{1\_6}$alkylcarbonyl, $C_{1\_6}$alkyloxycarbonyl, mercapto and CF$_3$. In one embodiment the substituents are selected from $C_{1\_6}$alkyl, $C_3$-$C_7$cycloalkyl, halogen, $C_{1\_5}$ alkoxy, hydroxyl, amino, mono- and di-C1_5alkyl amino, aryl, carboxyl, C1_5alkylcarbonyl, C1-6alkyloxycarbonyl.

The term "aryl" as used herein means an aromatic hydrocarbon radical of 6-14 carbon atoms such as phenyl, naphthalenyl, anthracenyl, biphenyl, and the like. Particular aryl groups are phenyl and naphthyl, especially phenyl.

An aryl group may be optionally substituted with one or more, in particular with 1, 2, 3, 4, or 5, or more in particular with 1, 2 or 3 substituents which each independently may be selected from C1_5alkyl, C3-$C_7$cycloalkyl, halogen, C1_5alkoxy, hydroxyl, amino, mono- and di-C1_5alkyl amino, aryl, nitro, cyano, carboxyl, $C_{1\_6}$alkylcarbonyl, $C_{1\_6}$alkyloxycarbonyl, azido, mercapto and CF3_.

The term "aryl$C_{1\_6}$alkyl" as used herein refers to a $C_{1\_6}$alkyl group substituted with an aryl group. In one embodiment the alkyl group is a C1_4alkyl and the group is "arylC1_4alkyl". C1-$_4$ alkyl and aryl are as specified herein. The aryl$C_{1\_6}$alkyl group is linked to the rest of the molecule via a carbon atom of the alkyl moiety. Aryl$C_{1\_6}$alkyl alkyl groups include benzyl, 2-phenylethyl, 1-phenylethyl, naphthylmethyl, 2-naphthylethyl, and the like.

The term "halogen" is generic to fluoro, chloro, bromo and iodo.

In a particular embodiment the N-terminus of the hydrogel-forming peptide bears one or two $R_a$ groups each independently selected from an optionally substituted linear or branched $C_{1-10}$alkyl, or bears one hydrogen and one group selected from $C(=O)R^1$, $C(=O)OR^1$, $C(=O)NHR^1$ and $C(=O)N(R^1)_2$; and each $R^1$ is independently as specified herein.

In further embodiments each $R^1$ independently is H, a linear or branched $C_{1-10}$alkyl, $C_{3-10}$cycloalkyl, an aryl$C_{1-6}$alkyl or an aryl. $R^1$ may also be a phenyl or a phenyl substituted with 1, 2 or 3 substituents selected from halogen, $C_{1-6}$alkyl and $C_{1-6}$alkyloxy.

In other embodiments each $R^1$ independently is H or a linear or branched $C_{1-6}$ alkyl. $R^1$ may be H or a methyl.

In further embodiments one Ra is H and the other Ra is H, a linear or branched $C_{1-10}$ alkyl, or C(=O)R1; in particular embodiments one Ra is Hand the other Ra is H or C(=O)R1; wherein in the latter $R^1$ is a linear or branched $C_{1-6}$ alkyl; or in particular embodiments one Ra is H and the other Ra is H or an acetyl.

In one embodiment one Ra is hydrogen and the other Ra is hydrogen or $C_{1-4}$ alkylcarbonyl.

To avoid ambiguity it should be clear that when the C-terminus of the peptides forms a group CORb, the carbonyl in said group CORb is part of the C-terminal amino acid.

In a particular embodiment the C-terminus of the hydrogel-forming peptide bears a Rb group selected from $OR^2$ or $N(R^2)_2$ and each $R^2$ is as specified herein.

In other embodiments each $R^2$ independently is H, a linear or branched $C_{1-10}$ alkyl, a $C_{3-10}$ cycloalkyl, a aryl$C_{1-6}$ alkyl or a phenyl optionally substituted with 1, 2 or 3 substituents selected from halogen, $C_{1-6}$ alkyl and $C_{1-6}$ alkyloxy. In particular embodiments each $R^2$ independently is H, a linear or branched $C_{1-6}$ alkyl, a benzyl or a phenyl.

In certain embodiments, Rb is a group $OR^2$ wherein $R^2$ is H or a linear or branched $C_{1-6}$ alkyl; or Rb is a group $N(R^2)_2$ wherein each $R^2$ independently is H or a linear or branched $C_{1-6}$ alkyl.

In certain embodiments Rb is hydroxyl, amino ($NH_2$), $C_{1-6}$ alkylNH—, ($C_{1-6}$ alkyl)2NH—; in particular Rb is OH, amino or aminomethyl. In particular embodiments Rb is OH or $NH_2$.

Embodiments of the invention concern those peptides either wherein each Ra is H and/or wherein Rb is OH or NH2.

In particular embodiments, said amphipathic peptide hydrogelator is a hexapeptide.

Short amphipathic peptide hydrogelator sequences are preferred as they are simpler to produce, better tunable and have lower production costs because it simplifies the synthesis and purification of larger quantities of peptides. When the peptide sequences are too short (two or three amino acids), structural variations might immediately lead to loss of hydrogelating ability. Therefore, an alpha-peptide of intermediate length, i.e. between 4 and 16 amino acids, preferably between 5 and 8 amino acids, most preferably a hexapeptide, is preferred.

The use of biodegradable, short, tunable and biocompatible amphipathic peptide hydrogelators with a high loading capacity allows controlling and extending the duration of action of a biologically active ingredient. Moreover, these advantages offer the possibility to be compatible and applicable for different types of biologically active ingredients ranging from small molecules to proteins. Constituted by peptides only, these systems take advantage of low production costs, which is very important for remaining competitive and allowing access for most patients. This technology could be broadly applicable to other peptide-based (and protein-based) therapeutics and drug candidates for different applications. The simplicity of the formulation (e.g. no need for additional excipients) might also be a significant advantage.

In particular embodiments, the amphipathic peptide hydrogelator is a hexapeptide with the following formula: X—Y—X—Y—X—Y, wherein X is a hydrophobic amino acid, preferably Phe, Trp, Tyr, Ala, Val, Leu, Iie, Met, Pro or Gly and Y is a hydrophilic amino acid, preferably Gin, Glu, Asn, Ser, Thr, Cys, Arg, His, Lys, Asp or Gly.

The term "hydrophobic amino acids" refers to naturally occurring amino acids having a hydrophobic side chain, such as alanine (Ala), valine (Val), leucine (Leu), isoleucine (Iie), methionine (Met), praline (Pro) and the aromatic amino acids phenylalanine (Phe), tyrosine (Tyr) and tryptophan (Trp). Further included is the non-natural amino acid cyclohexylalanine. Other examples include ring-substituted phenylalanine, tyrosine or tryptophan derivatives, such as halogenated phenylalanine or halogenated tryptophan. The halogen used for halogenation may be any halogen known in the art, including Bromine, Iodine, Chlorine and Fluorine. (Non-limiting examples of ring-substituted phenylalanine, tyrosine or tryptophan derivatives include fluoro/chloro/bromo/iodo/cyano-phenylalanine, a.tyrosine, m.tyrosine, dimethyltyrosine derivates, dimethyltryptamine, fluoro-tryptophan, hydroxy-tryptophan, methoxy-tryptophan. Due to it minimal side chain, Glycine (Gly) can fit into both hydrophilic and hydrophobic environments. Therefore, Gly could successfully replace a hydrophobic amino acid.

The term "hydrophilic amino acids" refers to amino acids having a hydrophilic side chain; such side chain may be uncharged, positively (cationic) or negatively charged (anionic) under normal physiological conditions, in particular at neutral pH. Uncharged hydrophilic amino acids include asparagine (Asn) and glutamine (Gin), serine (Ser), threonine (Thr), cysteine (Cys); positively charged hydrophilic amino acids include arginine (Arg), histidine (His) and lysine (Lys), and the non-natural amino acid ornithine; negatively charged amino acids include aspartic acid (Asp) and glutamic acid (Glu). Due to it minimal side chain, Glycine (Gly) can fit into both hydrophilic and hydrophobic environments. Therefore, Gly could successfully replace a hydrophilic amino acid.

As known in the art, hydrogels require a pH of at least 4, more preferably a pH that is in the range of pH 6 to pH 8, more preferably about physiological pH for in vivo administration to avoid a pain sensation in the host. The pH of the hydrogel can be influenced by controlling the pH of the hydrogel-forming composition itself and/or by addition of buffers. Various pH buffers can be used. For example, tris(hydroxymethyl)aminomethane (Tris), N-(tri(hydroxymethyl)methyl)glycine (Tricine), 3-[N-tris(hydroxymethyl)methylamino]-2-(TAPSO), 3-(N,N-Bis[2-hydroxyethyl]amino)-2-hydroxypropanesulfonic acid hydroxypropanesulfonic acid (DIPSO), 2-[4-(2-hydroxymethyl)-piperazin-1-yl]ethanesulfonic acid (HEPES), 2-[1,3-dihydroxy-2-(hydroxymethyl) propan-2-yl]amino]ethane-sulfonic acid (TES), 3-Morpholinopropane-1-sulfonic acid (MOPS), N,N-bis(2-hydroxyethyl)-2-aminoethanesulfonic acid (BES), 1,4-Piperazinediethanesulfonic acid (PIPES), 2-(N-morpholino) ethanesulfonic acid (MES) and other buffers known to the skilled person.

In particular embodiments, the amphipathic peptide hydrogelator according to present invention has an amino acid sequence according to any one of SEQ ID NOs: 1-26

(Table 1), preferably any one of SEQ ID NOs: 1, 2, 4, 5, 9, 10, 11, 12, 13, 14, 15, 16, 17, 18, 19, 20, 21, 22, 23, 24, 25 or 26 or the salt-forms thereof, preferably the trifluoroacetic salts, sodium chloride salts or acetic acid salts.

In particular embodiments, the amphipathic peptide hydrogelator according to present invention comprises at least one halogenated phenylalanine or tryptophan residue. The halogen used for halogenation may be any halogen, such as Bromine, Iodine, Chlorine, or Fluorine, preferably, Bromine or Iodine.

In particular embodiments, the amphipathic peptide hydrogelator according to present invention has an amino acid sequence according to any one of SEQ ID NOs: 37-43 (Table 1), or the salt-forms thereof, preferably the trifluoroacetic salts, sodium chloride salts or acetic acid salts.

The preferred sequences of the hydrogelators that form a gel are provided in FIG. 29.

In further particular embodiments, the amphipathic peptide hydrogelator according to present invention has a peptide sequence according to SEQ ID NO: 16 or SEQ ID NO: 18 or the salt-forms thereof, preferably the trifluoroacetic salts, sodium chloride salts or acetic acid salts.

In further particular embodiments, the amphipathic peptide hydrogelator according to present invention can be used for a more sustained release of drugs, implying a need for improved proteolytic stability of the peptide hydrogelators. The proteolytic stability of such peptide substrates can hence improve the release properties of the resulting hydrogels. Natural L-amino acid containing peptides are well known to be easily recognized and degraded by proteolytic enzymes. To tackle this susceptibility to proteolysis, different 'tricks' can be considered, such as the incorporation of D-amino acids, halogenated phenylalanine or tryptophan residues and/or 13-(homo) amino acids. Within the field of peptide hydrogels, the modification of one chiral centre from L to D changes the orientation of the side chain and this can in turn strongly affect the macroscopic properties of the gel. In literature, it was shown that the gelation properties of heterochiral peptide hydrogelators can be altered, even via the chirality switch of a single residue. Homochirality of peptide hydrogelators appeared to be beneficial in terms of mechanical properties compared to mixtures of both L- and D-peptides. In order to circumvent this issue, retro-inverso peptide analogues can be developed to increase the proteolytic stability of the peptide, while maintaining side chain topology. As an example, the retro-inverso peptidomimetic of sequence peptide 2, sequence peptide 24, combines reversal of the N-----+C side chain sequence of the parent peptide, and the inversion of the chirality of each amino acid (from L to D). The retro-inverso (RI) peptide peptide 24 presents the same three-dimensional side chain topology as its L-counterpart peptide 1. Peptide analogue peptide 18 can be regarded as an intermediate between peptide 2 and peptide 24, since the amino acid sequence is reversed, yet L-chirality is preserved. The same can of course be done in any one of the other sequences as defined in Tables 1 and 2 below, which also forms part of the invention.

In further particular embodiments, the amphipathic peptide hydrogelator can comprise a peptide as defined in Tables 1 or 2, wherein a 13-(homo) amino acid is introduced to increase the proteolytic stability of the peptide gelator. For this, a dipeptidic $13^3$-(homo)-phenylalanine-a-phenylalanine ($13^3$-homo-Phe-a-Phe) segment was introduced into peptide 2, now called peptide 27. The introduction of such a hydrophobic "dyad" can be important to keep the right alternation between hydrophobic and hydrophilic residues, affording an amphipathic heptapeptide able to promote 13-sheet formation. Mixed a/13-peptide hydrogelators were shown to be less prone to enzymatic degradation in solution as well as in a gel state, in presence of elastase.

In further particular embodiments, the amphipathic peptide hydrogelator according to present invention has an amino acid sequence according to any one of SEQ ID NOs: 1-26 (Table 1), wherein a halogenated phenylalanine or tryptophan residue is inserted to increase the rigidity, the proteolytic stability of the peptide gelator and/or in vivo stability of the resulting gel.

Salt-forms of the hydrogel-forming peptides include, where possible, acid addition and base addition salt forms. Preferred are those that are pharmaceutically acceptable. The pharmaceutically acceptable acid addition salts can conveniently be obtained by treating the peptides having a basic group with such appropriate acid. Appropriate acids comprise, e.g., inorganic acids such as hydrohalic acids, e.g. hydrochloric or hydrobromic acid, sulfuric, nitric, and phosphoric acid; or organic acids such as acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic acid. The peptides containing an acidic proton may also be converted into their metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts. Of particular interest are the trifluoroacetate salts.

As used herein, the term "hydrogel-forming composition" refers to the resulting product of the act of combining parts or elements to form a whole which has the ability to form a hydrogel. In present invention, the elements which are combined are at least an amphipathic peptide hydrogelator and one or more of biologically active ingredients and/or biological materials.

The hydrogel-forming composition according to present invention can be either a co-formulation or a biogel composition.

The hydrogel-forming compositions of the invention may also be dried to form xerogels, which may be reconstituted by addition of water.

The term "co-formulation" as used herein, refers to a hydrogel-forming composition comprising more than one molecule. As used herein, the co-formulation always comprises an amphipathic peptide hydrogelator which serves as a drug delivery platform by encapsulating the biologically active ingredient and/or biological material as a cargo. With the co-formulation approach, both the amphipathic peptide hydrogelator and the incorporated biologically active ingredient can be modified separately, depending on the need (e.g. cargo, dose, rate of release).

As used herein, the term "biogel composition" refers to a hydrogel-forming composition in which the amphipathic peptide hydrogelator and the biologically active ingredient are coupled, optionally by a linker. In a preferred embodiment, the biologically active ingredient is also a peptide, preferably selected from the group comprising: synthetic or natural peptides, biological macromolecules, polypeptides, proteins, peptide analogues, peptidomimetics, antibodies, nanobodies, antibody fragments and derivatives thereof. When both the amphipathic peptide hydrogelator and the biologically active ingredient are peptides, the coupling (e.g. through an amide or peptide bond) of the amphipathic peptide hydrogelator amino acid sequence and the biologically active ingredient amino acid sequence results in the formation of a single peptide. This simplifies the production process of the biogel composition. In a particular embodiment, the biogel composition is a peptide, preferably a biodegradable peptide. The term "biogel" as used herein, refers to a hydrogel comprising the biogel composition as described herein.

As used herein, the term "controlled release" refers to the presentation or delivery of ingredients in response to stimuli or time. Controlled release can be achieved by, for example, use of an injectable drug carrier such as gels, implants and devices. In present invention, hydrogels are preferably used for controlled release of one or more biologically active ingredients.

As used herein, the term "biologically active ingredient" (sometimes also referred to as "active ingredient" or "active pharmaceutical ingredient") is meant to include ingredients or agents that are biologically active. Also covered by these terms are diagnostic agents as well as so-called "cosmeceuticals". Diagnostic agents include, for example, fluorescent proteins (e.g. green fluorescent protein or GFP) or radiolabeled molecules. Cosmeceuticals include active ingredients that have an effect on the outer appearance of an individual such as on skin, hair, lips, and eyes, and encompass anti-wrinkling agents and agents that improve complexion. In these applications the hydrogels preferably are administered externally. Active pharmaceutical ingredients (also referred to as drugs) are of particular interest and form a subgroup of biologically active ingredients.

The biologically active ingredients may include small molecules (such as those having a molecular weight of less than about 1,500), synthetic or natural active ingredients such as monosaccharides, disaccharides, trisaccharides, oligosaccharides, peptides, nucleic acids but also nucleic acid analogues and derivatives; or large molecules, including plasmids, vectors, polysaccharides, biological macromolecules, e.g., larger peptides (polypeptides), proteins, peptide analogues, peptidomimetics, antibodies, antibody fragments, nucleic acid based molecules (e.g. DNA, RNA, mRNA, tRNA, RNAi, siRNA, microRNA, or any other DNA or RNA-like molecules), polynucleotides, oligonucleotides, enzymes, antibiotics, antiviral agents, antifungal agents, anti-inflammatory agents, growth stimulating or inhibiting agents, blood clotting or coagulation factors, immunomodulators, natural ligands, immunoglobulins, extracts made from biological materials such as bacteria, plants, fungi, or animal cells or tissues, therapeutic agents, preventatives, diagnostic agents, imaging agents, aptamers (including or protein aptamers) or derivatives thereof. Macromolecules can be present in a modified form. For example, linked to a label (e.g. labeled nanobodies) or linked to another molecule (e.g. antibody drug conjugates).

In one embodiment the biologically active ingredients are water-soluble, particularly are water-soluble active pharmaceutical ingredients. Such ingredients may belong to Class I or III of the Biopharmaceutical Classification System (BCS), which classifies drug substances into four classes: Class I-High Permeability, High Solubility; Class II-High Permeability, Low Solubility; Class III-Low Permeability, High Solubility; Class IV-Low Permeability, Low Solubility. Water-soluble drugs can also be specified by the amount of a water (g) required to solve 1 g of a compound, wherein water-soluble drugs are those fulfilling the following solubility qualifications: 10-30 g ("soluble"); 30-100 g ("sparingly soluble"); 100-1000 g ("slightly soluble"); 1000-10000 g ("very slightly soluble" or "poorly soluble"); or particularly soluble, sparingly soluble and slightly soluble drugs.

Drugs that can be incorporated in the hydrogels of the invention include those used in the treatment of diseases related to the nervous system such as ALS, Alzheimer's disease, Parkinson's disease; psychotherapeutic diseases such as bipolar disorder, anxiety, depression; metabolic diseases such as diabetes (e.g. insulin) and hypolipemic agents; infectious diseases such as antifugals, antibiotics, antivirals such as to treat HIV or HCV; cardiovascular conditions such as antihypertensives; anti-acne agents; anti-allergic agents; anti-asthmatics; anticancer agents; hormonal contraceptives; analgesics; agents to treat sleep disorders and overweight; anti-inflammatories; mucolytics; antitussives; antiulceratives. Of interest for incorporation into the hydrogels are drugs that are used in the treatment of chronical diseases.

In particular embodiments, the biologically active ingredient is a drug used for pain relief, preferably selected from the group comprising opioids and opioid peptides, non-peptidic opioid analogues, non-opioid analgesics, antidepressants and anticonvulsants. Non-limiting examples of opioids are morphine or morphine-derivatives such as esters of morphine or ethers of morphine, 14-alkoxymethopon derivatives such as 14-methoxymetopon or 14-methoxy-5-methylmorphinone, codeine, dihydrocodeine, fentanyl, hydrocodone, hydromorphone, meperidine, tramadol, methadone, pethidine, oxycodone, preferably morphine and 14-methoxymetopon, more preferably 14-methoxymetopon.

In particular embodiments, the biologically active ingredient is an anti-inflammatory drug preferably C-type natriuretic peptide.

In one embodiment the biologically active ingredients are antibodies or antibody fragments. The term "antibody" is meant to include monoclonal antibodies, polyclonal antibodies and multispecific antibodies (e.g. bispecific antibodies). Antibody fragments comprise a portion of an antibody, generally the antigen binding or variable region thereof. Examples of antibody fragments include Fab, Fab', F(ab').sub2 and Fv fragments; nanobodies, diabodies; linear antibodies; single-chain antibody molecules; multispecific antibodies formed from antibody fragments.

In particular embodiments, the biologically active ingredient is a high molecular weight therapeutic cargo, more preferably a peptide with a molecular weight of at least 1000 Da, at least 5000 Da, at least 10 000 Da, at least 15 000 Da, preferably at least 1500 Da.

In particular embodiments, the biologically active ingredient is a peptide-based analgesic, preferably an opioid peptide, more preferably an opioid peptide with the sequence Dmt-OLys-Phe-Phe-$NH_2$ (Table 5; EO-CM-OP; SEQ ID NO: 57), Dmt-OArg-Phe-Phe-NH2 (Table 5; CM-80-OP; SEQ ID NO: 58) or Dmt-DArg-Aba-I3Ala-$NH_2$ (Table 5; KGOP01; SEQ ID NO: 59).

The biologically active ingredient can also be a vaccine. Vaccines that can be incorporated in the hydrogels of the present invention include killed, but previously virulent, micro-organisms that have been treated with chemicals, heat, radioactivity or antibiotics. Examples include influenza, cholera, bubonic plague, polio, hepatitis A, and rabies.

Further included are attenuated microorganisms, in particular attenuated viruses such as in the vaccines against viral diseases, yellow fever, measles, rubella, mumps, and the bacterial disease typhoid.

Further included is the *Mycobacterium tuberculosis* vaccine. A further type includes the toxoid-based vaccines such as tetanus and diphtheria vaccines. Still a further class of vaccines are those based on protein subunits (or protein fragments) such as the subunit vaccine against Hepatitis B virus, the virus-like particle (VLP) vaccine against human papillomavirus (HPV) and the *Haemophilus* influenza type B vaccine.

The hydrogel-forming compositions of the invention can also be used for the controlled release of the various biologically active ingredients encapsulated in the hydrogel networks. Controlled release may be sustained delivery for periods varying from days (such as one day, two, three, four, five, six or seven days), to weeks (such as one week, two, three or four weeks) or even months (such as one month, or two or three months).

The hydrogel-forming compositions of the invention preferably contain the biologically active ingredient in a therapeutically effective amount, which refers to an amount effective in the prevention or treatment of a disease or disorder, for the prevention or treatment of which the biologically active ingredient is effective. The hydrogel-forming compositions may be used in a method of treatment of or prophylaxis in a patient suffering from a disease or disorder, said method comprising the administration to said patient a therapeutically effective amount of the hydrogel-forming composition.

The hydrogel-forming compositions of the invention can take the form of pharmaceutical compositions comprising a hydrogel as described herein which comprises a biologically active ingredient, in particular may be an active pharmaceutical ingredient. If desired the hydrogel-forming compositions may contain further carrier materials.

Preferred are hydrogel-forming compositions for parenteral use, in particular parenteral pharmaceutical compositions for subcutaneous or intramuscular administration. The parenteral pharmaceutical compositions may contain any of the carrier materials customarily used in such hydrogel-forming compositions. The hydrogel-forming compositions of the invention can also be formulated such that they are fit for implantation. In that instance the viscosity may be increased to obtain a more solid (in particular solid like) consistency.

In particular embodiments, biological materials can also be living matter such as cells or exosomes, which are incorporated in the hydrogels of the invention. The latter form a scaffold in which the encapsulated cells or exosomes maintain viability and function.

In particular embodiments, such biological materials can be used in cell therapy, tissue repair or in tissue engineering applications, where hydrogel encapsulated cells are injected or implanted in the body in the desired site to effect therapy or respectively to regenerate damaged or diseased tissues.

In particular embodiments, depending on the cell type, the hydrogel-forming compositions of the present invention may be injected or implanted into any acceptable tissue such as, for example, cartilage, bone, tendon, ligament, intervertebral disc, meniscus, bladder, cardiac muscle, skeletal muscle, myocardium, fascia, adipose tissue, nerve, heart valve, intestine, lung, blood vessels, as well as organs such as kidney, liver, pancreas, stomach, and colon.

In particular embodiments, the cells may be tenocytes, fibroblasts, ligament cells, endothelial cells, lung cells, epithelial cells, smooth muscle cells, cardiac muscle cells, skeletal muscle cells, islet cells, neuronal cells, hepatocytes, kidney cells, bladder cells, urothelial cells, chondrocytes, and bone-forming cells.

In particular embodiments in which encapsulated cells are non-proliferating cells, the latter may be pancreatic islets, hepatic cells, neural cells, renal cortex cells, vascular endothelial cells, thyroid or parathyroid cells, adrenal cells, thymic cells, ovarian cells, or chondrocytes. Further, the cells may be stem cells, such as bone marrow-derived stem cells, embryonic stem cells, umbilical cord-derived stem cells, placenta-derived stem cells, and amniotic fluid-derived stem cells. Sources of the cells may include fetal or adult organisms, particularly mammals, or established cell lines.

In a related aspect the invention provides the hydrogel-forming composition as disclosed herein for use in medicine.

In particular embodiments, the hydrogel-forming composition according to the invention is used for a medical application chosen from the list comprising drug delivery systems, tissue engineering, tissue repair, regenerative medicine, diagnostics, wound dressing, separation of biomolecules or cells, barrier materials to regulate biological adhesion and biosensor; preferably drug delivery systems.

In particular embodiments, the hydrogel-forming composition according to the invention is used for personal care applications chosen from the list comprising pharmaceuticals, dietary supplements, consumer products used in personal hygiene and/or beautification, cosmoceuticals and cosmetics.

In particular embodiments, the hydrogel-forming composition according to the invention is used for cosmetics chosen from the list comprising skin moisturizers, perfumes, lipsticks, fingernail polishes, eye and facial makeup preparations, shampoos, permanent waves, hair colors, toothpastes, and deodorants. For example, the use of the hydrogel-forming composition according to the invention as a skin care product could increase skin moisture, elasticity, wrinkle smoothing and supply the skin with essential substances (minerals, vitamins, fatty acids, lipids etc.).

In particular embodiments, the hydrogel-forming composition according to the invention is used as a matrix/scaffold suitable for 2D or 3D in vitro cell culture, tissue engineering and/or tissue repair. More particularly, the hydrogel-forming composition according to the invention can also be used for artificial in vitro models.

In particular embodiments, the hydrogel-forming composition according to present invention is used for the controlled release of one or more biologically active ingredient(s).

The hydrogel-forming composition can be administered to a subject by an administration route chosen from the list comprising topical, subcutaneous, intra-articular, epidural, intracerebral, intracerebroventricular, intracardiac, intramuscular, intraocular, intraperitoneal, intrathecal, intrauterine and intravaginal.

In particular embodiments, the hydrogel-forming composition is used for subcutaneous delivery of one or more biologically active ingredient(s).

In particular embodiments, the hydrogel-forming composition is used for the treatment of a disease chosen from the list comprising, but not limited to, infectious diseases, allergies, intestinal diseases, endocrine disease, cardiovascular diseases, pulmonary diseases, skin diseases, central nervous system diseases, inflammatory diseases and cancers.

In particular embodiments, the hydrogel-forming composition is used for the treatment of acute, chronic and/or neuropathic pain.

In a further aspect of the invention, the hydrogel-forming composition for controlled release of one or more biologically active ingredient(s) and/or biological material is a co-formulation.

Preferably, such a co-formulation comprises:
(a) an amphipathic peptide hydrogelator comprising at least 4 and at most 16 amino acid residues; and
(b) one or more biologically active ingredients and/or biological materials.

In particular embodiments, the biologically active ingredient and/or biological material is as described herein.

In particular embodiments, the amphipathic peptide hydrogelator is as described herein.

In particular embodiments, the hydrogel-forming composition for controlled release of a biologically active ingredient and/or biological material is a co-formulation and such co-formulations can be used as carriers for various biologically active ingredients as well as biological materials. Thus the invention provides co-formulations comprising a hydrogel as described herein and one or more biological materials or one or more biologically active ingredients, or a combination thereof. The co-formulations containing cells may also be useful in cell-based high-throughput screening and drug discovery. The co-formulation as described herein can release therapeutics via various mechanisms, such as (de) swelling, external triggers: pH or temperature, erosion, diffusion. Moreover, the co-formulation can release therapeutics in a sustained manner over prolonged periods of time.

In a further aspect of the invention, the hydrogel-forming composition for controlled release of a biologically active ingredient is a biogel composition for controlled release of a biologically active ingredient, comprising:
(a) an amphipathic peptide hydrogelator comprising at least 4 and at most 16 amino acid residues; and
(b) one or more biologically active ingredients
wherein (a) and (b) are coupled, optionally by a linker.

In particular embodiments, additional amphipathic peptide hydrogelators can be added to the mixture of (a) and (b) above, e.g. when (a) and (b) are coupled. Is such an embodiment, the hydrogel composition would comprise coupled (a) and (b) plus additional (a) in a mixture.

In particular embodiments, the biogel composition is used as a biologically active ingredient in the co-formulation composition as described herein.

In the context of present invention, the term "biogel composition" is as described herein.

In the context of present invention, the term "coupled" as used herein is synonymous with "connected", "bound", "fused", "joined" and refers to a physical link between at least two components or to bring together different elements into a complex.

In particular embodiments of the biogel composition as described herein, the biologically active ingredient is a peptide or a protein, preferably selected from the group comprising: synthetic or natural peptides, biological macromolecules, polypeptides, proteins, peptide analogues, peptidomimetics and antibodies and derivatives thereof.

In particular embodiments of the biogel composition as described herein, the amphipathic peptide hydrogelator and biologically active ingredient are alpha-peptides. The use of unprotected and unmodified alpha-peptide sequences, synthesized from natural amino acids and lacking any synthetic protecting group, is extremely attractive for in vivo applications as such systems are easily degraded by proteolytic enzymes, giving way to non-toxic L-amino acids and peptide segments. For application of the biogel composition according to present invention as drug delivery systems, biogel compositions can modulate release kinetics by alteration of the peptide sequence. To achieve prolonged in vivo stability, unnatural amino acids such as D-amino acids, 13-amino acids, or 13-(homo)-amino acids can be used.

As used herein, the term "linker" refers to a connecting element that serves to link other elements. In present invention, the linker, preferably a cleavable linker, is a unit including 'spacers' like glycine units or polyethylene glycol (PEG) units. When the hydrogel-forming composition is a biogel composition, the linker is used to connect the biologically active ingredient to the amphipathic peptide hydrogelator.

In particular embodiments of the biogel composition as described herein, the linker is a covalent linker, achieving a covalent bond. The terms "covalent" or "covalent bond" refers to a chemical bond that involves the sharing of one or more electron pairs between two atoms. For many molecules, the sharing of electrons allows each atom to attain the equivalent of a full outer electron shell, corresponding to a stable electronic configuration. Covalent bonds include different types of interactions, including a-bonds, TT-bonds, metal-to-metal bonds, agostic interactions, bent bonds and three-center two-electron bonds.

Figure 2:
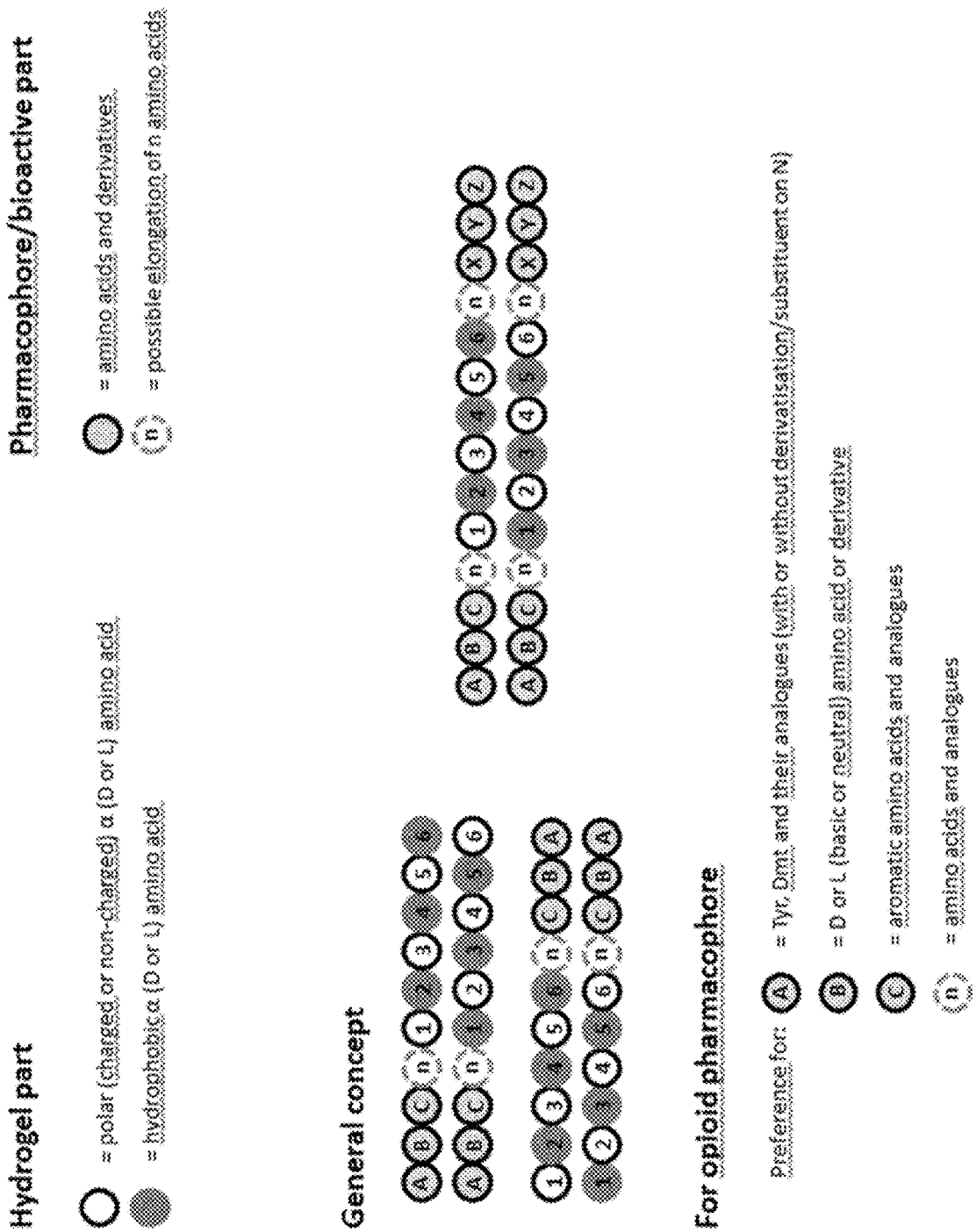
FIG. 2 represents a scheme for exemplary amino acid sequences of the hydrogel forming composition which form a biogel. 'n' represents a peptide linker comprising of an undefined number of amino acids or analogues thereof. In the description, 'n' is referred to as 'K' to avoid possible confusion with the chemical element Nitrogen ('N') and the integer in the chemical formulas used herein. The combination A-B-C, C-B-A, or X—Y—Z in the figure represents a peptide active agent, wherein 'A', 'B', 'C', 'X', 'Y' and 'Z' are random amino acids or derivatives thereof. It should be clear that the sequences A-B-C and X—Y—Z could be replaced by any other number or sequence of amino acids, depending on the active ingredient. 'X', 'Y' and 'Z' are referred to as 'E', 'F', 'G' in the description to avoid possible confusion with the defined hydrophobic ('X'), hydrophilic amino acids ('Y'), and substituents S or O ('Z'). The letters used in this figure hence do not correspond to the one-letter code of amino acids.

In particular embodiments of the biogel composition as described herein, the linker is chosen from the list comprising amide, peptide bond, ester, carbonate, carbamate, glycoside, acetal, disulfide, hydrazone, tert-butyloxycarbonyl, paramethoxybenzyl, dialkyl, diaryldialkoxysilane, orthoester, 13-thiopropionate, ketal, phosphoramidate, vinyl ether, imine, aconityl, trityl, polyketal and azo. An exemplary linker can be a peptide linker of one or more amino acids or derivatives thereof, such as shown in FIG. 2, indicated with 'n'. Further herein the linker 'n' is referred to as 'K' to avoid possible confusion with the chemical element Nitrogen ('N') and the integer in the chemical formulas used herein. Preferably, the peptide linker is a peptide motif which is specifically recognized and cleaved by an endopeptidase. Preferably, the linker is an ester, hydrazine, carbonate or peptide linker of one or more amino acids or derivatives thereof. In particular embodiments of the biogel composition as described herein, the linker is a cleavable linker. The term "cleavable" (sometimes also referred to as "biodegradable"), as used herein, refers to the capability of being split or divided, more particularly, dividing a complex molecule into simpler molecules. Proteolysis is the breakdown of proteins into smaller polypeptides or amino acids. Proteolysis is typically catalyzed by cellular enzymes called proteases. Low pH or high temperatures can also cause proteolysis without the need of enzymes. In vivo degradation of the hydrogel-forming composition according to present invention, results in the release of the bioactive domain, which can subsequently induce its biological effect in a region of interest.

Gel properties (e.g. stiffness, elasticity, viscosity,) are not limiting factors for present invention and might vary depending on their application.

The loading capacity of the hydrogel or biogel is preferably at least 5%, at least 10%, at least 20%, at least 30%, at least 40%, at least 50%, at least 60%, at least 70%, at least 80%, at least 90% or at least 95%, most preferably at least 70%. The loading capacity is party influenced by the solubility of the biologically active ingredient in a certain buffer (e.g. PBS) or water.

In particular embodiments of the biogel composition as described herein, the hydrogel forming composition is a biogel composition, preferably a peptide, preferably a biodegradable peptide. In particular embodiments, the biogel composition is a peptide with an amino acid sequence according to SEQ ID NO: 27, 28, 29, 30, 31, 32, 44, 45, 46, 47, 48, 49, 50, 51, 52, 53, 54, 55 or 56, preferably SEQ ID NO: 30 or 48.

Here, the biologically active ingredient is an opioid.

Present invention also includes variations upon the biogel composition peptide sequences listed in Table 2:

```
                                           (SEQ ID NO: 44)
H-Dmt-DArg-Phe-Phe-Glu-Phe-Gln-Phe-Lys-NH2

(SEQ ID NO: 45)
H-Dmt-DArg-Phe-Phe-Lys-Phe-Gln-Phe-Glu-Phe-NH2

(SEQ ID NO: 47)
H-Dmt-DArg-Phe-Phe-Glu-Trp-Gln-Trp-Lys-NH2

(SEQ ID NO: 44)
H-Dmt-DArg-Phe-Phe-DLys-DPhe-DGln-DPhe-DGlu-DPhe-
NH2
```

Additional variations can be obtained by the replacement of Dmt by Tyr or Tyr analogues, for example SEQ ID NO: 51, 52 and 56. The second amino acid can be a basic or neutral amino acid like Orn, Cit, Arg or mimetics or every D amino acid.

FIG. 2 provides a scheme with alternative peptide sequences for the biogel composition, with a focus on variations in the peptide sequence of the biologically active ingredient. The hydrogelator peptide sequence is not limited to the examples provided in the scheme and can be any sequence between 4 and 16 amino acids as described herein.

Possible peptide sequences are for example (see FIG. 2):

```
A-B-C-K-X-Y-X-Y or A-B-C-K-Y-X-Y-X,

A-B-C-K-X-Y-X-Y-X or A-B-C-K-Y-X-Y-X-Y,

A-B-C-K-X-Y-X-Y-X-Y or A-B-C-K-Y-X-Y-X-Y-X,

A-B-C-K-X-Y-X-Y-X-Y-X or A-B-C-K-Y-X-Y-X-Y-X-Y,

A-B-C-K-X-Y-X-Y-X-Y-X-Y or A-B-C-K-Y-X-Y-X-Y-X-Y-X,

A-B-C-K-X-Y-X-Y-X-Y-X-Y-X or A-B-C-K-Y-X-Y-X-Y-X-Y-X-Y,

A-B-C-K-X-Y-X-Y-X-Y-X-Y-X-Y or A-B-C-K-Y-X-Y-X-Y-X-Y-X-Y-X,

A-B-C-K-X-Y-X-Y-X-Y-X-Y-X-Y-X or A-B-C-K-Y-X-Y-X-Y-X-Y-X-Y-X-Y,

A-B-C-K-X-Y-X-Y-X-Y-X-Y-X-Y-X-Y or A-B-C-K-Y-X-Y-X-Y-X-Y-X-Y-X-Y-X,

A-B-C-K-X-Y-X-Y-X-Y-X-Y-X-Y-X-Y-X or A-B-C-K-Y-X-Y-X-Y-X-Y-X-Y-X-Y-X-Y,

A-B-C-K-X-Y-X-Y-X-Y-X-Y-X-Y-X-Y-X-Y or A-B-C-K-Y-X-Y-X-Y-X-Y-X-Y-X-Y-X-Y-X,

A-B-C-K-X-Y-X-Y-X-Y-X-Y-X-Y-X-Y-X-Y-X or A-B-C-K-Y-

X-Y-X-Y-X-Y-X-Y-X-Y-X-Y-X-Y,

A-B-C-K-X-Y-X-Y-X-Y-X-Y-X-Y-X-Y or A-B-C-K-
Y-X-Y-X-Y-X-Y-X-Y-X-Y-X-Y-X,

X-Y-X-Y-K-C-B-A or Y-X-Y-X-K-C-B-A,

X-Y-X-Y-X-K-C-B-A or Y-X-Y-X-Y-K-C-B-A,

X-Y-X-Y-X-Y-K-C-B-A or Y-X-Y-X-Y-X-K-C-B-A

X-Y-X-Y-X-Y-X-K-C-B-A or Y-X-Y-X-Y-X-Y-K-C-B-A,

X-Y-X-Y-X-Y-X-Y-K-C-B-A or Y-X-Y-X-Y-X-Y-X-K-C-B-A,

X-Y-X-Y-X-Y-X-Y-X-K-C-B-A or Y-X-Y-X-Y-X-Y-X-Y-K-C-
B-A,

X-Y-X-Y-X-Y-X-Y-X-Y-K-C-B-A or Y-X-Y-X-Y-X-Y-X-
K-C-B-A,

X-Y-X-Y-X-Y-X-Y-X-K-C-B-A or Y-X-Y-X-Y-X-Y-
X-Y-K-C-B-A,

X-Y-X-Y-X-Y-X-Y-X-Y-K-C-B-A or Y-X-Y-X-Y-X-
Y-X-Y-X-K-C-B-A,

X-Y-X-Y-X-Y-X-Y-X-Y-X-K-C-B-A or Y-X-Y-X-Y-
X-Y-X-Y-X-Y-K-C-B-A,

X-Y-X-Y-X-Y-X-Y-X-Y-X-Y-K-C-B-A or Y-X-Y-X-Y-
Y-X-Y-X-Y-X-Y-X-K-C-B-A,

X-Y-X-Y-X-Y-X-Y-X-Y-X-Y-X-K-C-B-A or Y-X-Y-X-
X-Y-X-Y-X-Y-X-Y-X-Y-K-C-B-A,

X-Y-X-Y-X-Y-X-Y-X-Y-X-Y-X-Y-K-C-B-A or Y-X-Y-X-
Y-X-Y-X-Y-X-Y-X-Y-X-K-C-B-A,

A-B-C-K-X-Y-X-Y-X-Y-K--E-F-G or A-B-C-K-Y-X-Y-X-K-E-F-G

A-B-C-K-X-Y-X-Y-X-Y-K-E-F-G or A-B-C-K-Y-X-Y-X-Y-K-E-
F-G

A-B-C-K-X-Y-X-Y-X-Y-X-K-E-F-G or A-B-C-K-Y-X-Y-X-Y-X-
K-E-F-G,

A-B-C-K-X-Y-X-Y-X-Y-X-K-E-F-G or A-B-C-K-Y-X-Y-X-Y-
X-Y-K-E-F-G,

A-B-C-K-X-Y-X-Y-X-Y-X-Y-K-E-F-G or A-B-C-K-Y-X-Y-X-
Y-X-Y-X-K-E-F-G,

A-B-C-K-X-Y-X-Y-X-Y-X-Y-X-K-E-F-G or A-B-C-K--Y-X-
Y-X-Y-X-Y-X-Y-K-E-F-G,

A-B-C-K-X-Y-X-Y-X-Y-X-Y-X-Y-K-E-F-G or A-B-C-K-Y-X-
Y-X-Y-X-Y-X-Y-X-K-E-F-G,

A-B-C-K-X-Y-X-Y-X-Y-X-Y-X-Y-X-K-E-F-G or A-B-C-K-Y-
X-Y-X-Y-X-Y-X-Y-X-Y-K-E-F-G,

A-B-C-K-X-Y-X-Y-X-Y-X-Y-X-Y-X-Y-K-E-F-G or A-B-C-K-
Y-X-Y-X-Y-X-Y-X-Y-X-Y-X-K-E-F-G,
```

-continued

A-B-C-K-X-Y-X-Y-X-Y-X-Y-X-Y-X-Y-X-K-E-F-G or A-B-C-K-Y-X-Y-X-Y-X-Y-X-Y-X-Y-X-Y-K-E-F-G,

A-B-C-K-X-Y-X-Y-X-Y-X-Y-X-Y-X-Y-X-Y-K-E-F-G or A-B-C-K-Y-X-Y-X-Y-X-Y-X-Y-X-Y-X-Y-X-K-E-F-G

A-B-C-K-X-Y-X-Y-X-Y-X-Y-X-Y-X-Y-X-K-E-F-G or

A-B-C-K-Y-X-Y-X-Y-X-Y-X-Y-X-Y-X-Y-K-E-F-G,
or

A-B-C-K-X-Y-X-Y-X-Y-X-Y-X-Y-X-Y-X-Y-K-E-F-G or

A-B-C-K-Y-X-Y-X-Y-X-Y-X-Y-X-Y-X-Y-X-K-E-F-G, wherein A-B-C is a peptide active agent, C-B-A is a peptide active agent and E-F-G is a peptide active agent, wherein A to C and E to G are random amino acids or derivatives or analogues thereof, and wherein (K) is a peptide linker comprising of an undefined number of amino acids or derivatives or analogues thereof. In some embodiments, A-B-C can be the inversed amino acid sequence of C-B-A, but intrinsically having the same biological activity. In some embodiments two different peptide active agents can be present on the C-terminal and N-terminal end of the hydrogelator peptide. It should be clear that the sequences A-B-C and E-F-G could be replaced by any other number or sequence of amino acids, depending on the active ingredient. The letters used in this section and in FIG. 2 do not correspond to the one-letter code of amino acids.

In a preferred embodiment of the peptide exemplified above, resulting in opioid-peptide hydrogels, 'A' is Tyr, Dmt or an analogue thereof (with or without derivatization/substituent), 'B' is a D- or L-(basic or neutral) amino acid or derivative thereof, 'C' is an aromatic amino acid or analogue thereof, 'K' is a linker comprising one or more amino acid(s) or analogue(s) thereof, 'X' is a hydrophobic amino acid, 'Y' is a hydrophilic amino acid and 'E', 'F' and 'G' are selected form any random amino acid or derivatives thereof.

The biologically active ingredient can be coupled to the hydrogelator peptide sequence C- or N-terminally, optionally by a linker sequence (K) consisting of an undefined number of amino acids or analogues thereof. When more than one biologically active ingredient is coupled to the hydrogelator peptide sequence, the biologically active ingredient C- and N-terminal of the hydrogelator peptide sequence can be identical or different.

The biogel composition according to present invention can be used for controlled-release of one or more biologically active ingredients. Controlled-release of the biologically active ingredient requires the biogel composition to be degraded over time by the body, allowing the release of the biologically active ingredient which can subsequently induce a biological effect. Depending on the required dose, the concentration and the volume of the biogel composition can be adapted. The presence of a cleavable linker between the hydrogelator part and the biologically active ingredient is especially advantageous when stepwise, proteolytic degradation of the biogel sequence (e.g. occurring from the C-terminal end towards the N-terminus of the biogel sequence) is not preferred or cannot be achieved.

Furthermore, it should be noted that stepwise degradation of the biogel could give rise to biogel fragments consisting of the biologically active ingredient and one or more amino acid residues of the hydrogelator part. For example, degradation of CM-136 may lead to the formation of a heptapeptide, pentapeptide or tripeptide (FIG. 23). It cannot be excluded that biogel fragments consisting of the biologically active ingredient and one or more amino acid residues of the hydrogelator part may be biologically active. For example, biogel fragments comprising an opioid analgesic and one or more amino acid residues of the hydrogelator part may be able to cross the blood-brain barrier and induce pain relief.

In another aspect, the invention provides methods for producing the hydrogel-forming compositions as defined herein.

The hydrogel can be prepared from the hydrogel-forming composition as described herein by allowing it to self-assemble into a hydrogel. Thus the invention further concerns a method for producing a hydrogel comprising a hydrogel-forming composition as specified herein, wherein the method comprises synthesizing and purifying the hydrogel-forming peptide, or preferably, an acid addition salt thereof, and allowing the hydrogel-forming peptide to assemble in the presence of a buffer, to obtain a self-sustaining hydrogel. This buffer can be water, saline solution, N-tris(hydroxymethyl)aminomethane (Tris), (tri(hydroxymethyl)methyl)glycine (Tricine), 3-[N-tris (Hydroxymethyl)methylamino]-2-hydroxypropanesulfonic acid (TAPSO), 3-(N,N-Bis[2-hydroxyethyl]amino)-2-hydroxypropanesulfonic acid acid (DIPSO), 2-[4-(2-hydroxymethyl)-piperazin-1-yl]ethanesulfonic acid (HEPES), 2-[[1,3-dihydroxy-2-(hydroxymethyl) propan-2-yl]amino] ethanesulfonic acid (TES), 3-Morpholinopropane-1-sulfonic acid (MOPS), N,N-bis(2-hydroxyethyl)-2-aminoethanesulfonic acid (BES), 1,4-Piperazinediethanesulfonic acid (PIPES), 2-(N-morpholino) ethanesulfonic acid (MES) and other buffers known to the skilled person.

In an aspect of the invention, the method for producing a hydrogel-forming composition according to present invention, comprises the steps of:

(a) synthesizing and purifying a hydrogel-forming peptide, optionally followed by salt exchange,
(b) mixing said hydrogel-forming peptide with one or more biologically active ingredients, or coupling said hydrogel-forming peptide to one or more biologically active ingredient(s), and
(c) contacting said hydrogel-forming composition obtained in (b) with an aqueous medium and allowing the formation of the hydrogel to take place.

The hydrogel-forming peptides described herein can be synthesized according to art-known methods of liquid phase or solid phase peptide synthesis by single amino acid coupling, fragment condensation or a combination thereof. Cleavage of synthesized peptides from a resin in solid phase peptide synthesis, removal of protecting groups and purification of peptides are well known in the art. Cleavage of synthesized peptides from a resin in solid phase synthesis can be done, for example, by trifluoroacetic acid. The synthesized peptides can be purified, e.g., by chromatography such as HPLC. For example, the peptides can be synthesized by solid phase methodology using standard coupling methods using t-butyloxycarbonyl (Boe) or 9-fluorenylmethoxy-carbonyl (Fmoc) protecting groups.

The peptides of the invention are self-assembling. In aqueous media they form supramolecular fibrillary assemblies, which eventually lead to the formation of hydrogel networks.

A concentration of 0.1 to 30¾w/v, 0.1 to 20% w/v, 0.1 to 20% w/v, more preferably of 0.5 to 5% w/v, most preferably 1 to 3% w/v, of peptide or peptide salt may be used to form self-sustaining hydrogels. The dose of biogel could also be changed by varying the concentration of the 'biogel composition' in the saline solution.

Aqueous media include water, in particular purified water such as mQ water; which water or purified water (such as mQ water) may contain a buffer. The pH of the buffer may be as mentioned above or may be in the range of pH 6 to pH 8.5, in particular in the range of pH 7 to pH 8. In one embodiment the buffer has a pH that ranges from about 3 to about 11, preferably at a pH ranging from about 4 to about 8, preferably about physiological pH, in particular a pH that is about 7.4.

In particular embodiments, the method for producing a hydrogel-forming composition according to present invention is performed at a pH ranging from about 3 to about 11, preferably at a pH ranging from about 4 to about 8, more preferably at physiological conditions, most preferably at a pH of 7.4.

Buffers that can be used include phosphate buffers, in particular HPO/-/H2PO4- based buffers wherein the counter ions are Na+ or K+, borate buffers, tris(hydroxymethyl)-aminomethane (Tris) buffers in particular Tris/HCl buffers, bicarbonate buffers, citrate buffers, and the like. The buffers may be supplemented with one or more salts such as sodium or potassium chloride or a combination thereof. The buffer can be a pre-prepared buffer solution, which may further contain one or more salts.

For example, tris(hydroxymethyl)aminomethane (Tris), N-(tri(hydroxymethyl)methyl)glycine (Tricine), 3-[N-tris(Hydroxymethyl)methylamino]-2-hydroxypropanesulfonic acid (TAPSO), 3-(N,N-Bis[2-hydroxyethyl]amino)-2-hydroxypropanesulfonic acid acid (DIPSO), 2-[4-(2-hydroxymethyl)-piperazin-1-yl]ethanesulfonic acid (HEPES), 2-[[1,3-dihydroxy-2-(hydroxymethyl) propan-2-yl]amino] ethanesulfonic acid (TES), 3-Morpholinopropane-1-sulfonic acid (MOPS), N,N-bis(2-hydroxyethyl)-2-aminoethanesulfonic acid (BES), 1,4-Piperazinediethanesulfonic acid (PIPES), 2-(N-morpholino) ethanesulfonic acid (MES) and other buffers known to the skilled person.

In a particular embodiment the buffer is PBS and the aqueous medium is purified water (so-called mQ water). The PBS preferably is used at a concentration that is in the range of 5 to 20 mM ions, in particular of 5 to 15 mM ions, more in particular the concentration is about 10 mM ions and is optionally supplemented with NaOH Hydrogels prepared using PBS are particularly interesting for use as carriers of biomaterials and active ingredients due to the buffering effect of PBS (to physiological pH) and the isotonic relation to the human body. In preferred embodiments, PBS (pH 7.4) or physiological saline solution (0.9% NaCl) are used as a buffer.

In another aspect of the invention, the method for producing a hydrogel-forming composition wherein the hydrogel-forming composition is a co-formulation according to the present invention, comprises the steps of:
(a) synthesizing and purifying the amphipathic peptide hydrogelator, optionally followed by salt exchange,
(b) dissolving one or more biologically active ingredient(s) or biological material in a aqueous medium containing a buffer
(c) contacting the peptide obtained in (a) with the aqueous medium containing one or more biologically active ingredient(s) or biological material of (b) and allowing the formation of the co-formulation to take place.

In particular embodiments, if the biological materials are living cells, the method for producing the co-formulation are performed under conditions (such as pH, temperature) in which the cells are viable and allows the dispersion of the living cells in the hydrogel network.

In another aspect of the invention, the method for producing a hydrogel-forming composition wherein the hydrogel-forming composition is a biogel composition according to the present invention, comprises the steps of:
(a) synthesizing and purifying the amphipathic peptide hydrogelator, optionally followed by salt exchange,
(b) coupling the peptide obtained in (a) with one or more biologically active ingredient(s), optionally via a linker, thereby forming a complex,
(c) dissolving the complex formed in (b) in an aqueous medium containing a buffer and allowing the formation of a biogel composition to take place.

In another aspect of the invention, the method for producing a hydrogel-forming composition wherein the hydrogel-forming composition is a biogel composition according to present invention, comprising the steps of:
(a) synthesizing and purifying the amphipathic peptide hydrogelator coupled to one or more biologically active ingredient(s), optionally followed by salt exchange,
(b) dissolving the complex formed in (a) in an aqueous medium containing a buffer and allowing the formation of a biogel composition to take place.

After protein synthesis and purification, it might be essential to eliminate salts, such as trifluorocetic acid (TFA), by salt exchange because they could be toxic and therefore undesirable in peptides intended for preclinical and clinical studies. For example, TFA can be removed by performing anion exchange on the same reversed phase HPLC on which the peptide was purified or TFA counterions can be replaced by a stronger acid such as hydrochloric acid (HCl).

In particular embodiments, the method for producing a hydrogel-forming composition, wherein the biologically active ingredient is a peptide or a protein, preferably selected from the group comprising: synthetic or natural peptides, biological macromolecules, polypeptides, proteins, peptide analogues, peptidomimetics, antibodies, antibody fragments and derivatives thereof.

The present invention is further illustrated in the following non-limiting examples.

EXAMPLES

Example 1: Design and Synthesis of Hydrogel Peptides for Co-Formulation

I) Materials and Methods

Peptide synthesis: Peptides were synthesized according to the standard solid-phase peptide synthesis method (W. Chan et al., 2000). Peptide purification was performed using preparative reverse high-performance liquid chromatography. A linear chromatography gradient starting from 10% of acetonitrile (+0.1% trifluoroacetic acid) to 80% in 20 min was used with a linear gradient. Trifluoroacetic acid (TFA) salt of pure product was obtained after lyophilisation of collected fractions.

Peptide Gelation:

The peptide gelation occurred by dissolving the TFA salt of the hexapeptide (2 mg) in 100 μL of PBS solution (pH 7.4) or physiological saline solution (0.9% NaCl).

II) Results

The design of new amphipathic a-peptide hydrogelators (Table 1) was based on fine-tuning the previously reported sequence H-Phe-Glu-Phe-Gln-Phe-Lys-OH 1 (MBG-1) (Table 1), which presented very promising results in terms of in vitro controlled release of model cargoes (M. Bibian et al., 2015).

The self-assembly process of hydrogelating peptides was influenced by different parameters such as the side chain hydrophobicity, ionic charges and the secondary structure propensity of the sequence. Indeed, formation of the 13-sheets that underpin hydrogelation occurred by hydrogen-bonding, noncovalent ionic and hydrophobic interactions between the side chains of the amino acids. Due to the very low pH (<4) of MBG-1 hydrogel, this hydrogelator was not suited for in vivo applications, as painful injections could emerge. To increase the hydrogel's pH, it was envisaged that the N- and C-terminal amino and carboxylic acid groups of the sequence could be replaced, respectively, by an acetyl and a carboxamide, while keeping similar gelation properties.

TABLE 1

Amphipathic α-peptide hydrogelators.

| alias | Sequence | Minimum gelation concentration (w/v % in PBS) | SEQ ID NO |
|---|---|---|---|
| 1 (MBG-1) | H-Phe-Glu-Phe*-Gln-Phe-Lys-OH | 1 (in mQ:PBS 50:50) | SEQ ID NO: 1 |
| 2 | H-Phe-Glu-Phe*-Gln-Phe-Lys-NH$_2$ | 2 | SEQ ID NO: 2 |
| 3 | Ac-Phe-Glu-Phe*-Gln-Phe-Lys-NH$_2$ | / | SEQ ID NO: 3 |
| 4 | H-DPhe-DGlu-DPhe*-DGln-DPhe-DLys-NH$_2$ | 3 | SEQ ID NO: 4 |
| 5 | H-Ile-Glu-Ile-Gln-Ile-Lys-NH$_2$ | 2 | SEQ ID NO: 5 |
| 6 | H-Leu-Glu-Leu-Gln-Leu-Lys-NH$_2$ | / | SEQ ID NO: 6 |
| 7 | H-Val-Glu-Val-Gln-Val-Lys-NH$_2$ | / | SEQ ID NO: 7 |
| 8 | H-Ala-Glu-Ala-Gln-Ala-Lys-NH$_2$ | / | SEQ ID NO: 8 |
| 9 | H-Cha-Glu-Cha-Gln-Cha-Lys-NH$_2$ | 2 | SEQ ID NO: 9 |
| 10 | H-Phe-Glu-Phe*-Asn-Phe-Lys-OH | 1 | SEQ ID NO: 10 |
| 11 | H-Phe-Glu-Phe*-Asn-Phe-Lys-NH$_2$ | 1 | SEQ ID NO: 11 |
| 12 | H-Trp-Glu-Trp*-Gln-Trp-Lys-NH$_2$ | 1 | SEQ ID NO: 12 |
| 13 | H-(2-Nal)-Glu-(2-Nal)-Gln-(2-Nal)-Lys-NH$_2$ | 2 | SEQ ID NO: 13 |
| 14 | H-Trp-Glu-Phe*-Gln-Phe-Lys-NH$_2$ | 2 | SEQ ID NO: 14 |
| 15 | H-Phe-Glu-Phe*-Gln-Trp-Lys-NH$_2$ | 2 | SEQ ID NO: 15 |
| 16 | H-Phe-Gln-Phe*-Gln-Phe-Lys-NH$_2$ | 2 | SEQ ID NO: 16 |
| 17 | H-DPhe-DGlu-DPhe*-DGln-DPhe-DLys-NH$_2$ | 2 | SEQ ID NO: 17 |
| 18 | H-Lys-Phe-Gln-Phe*-Glu-Phe-NH$_2$ | 2 | SEQ ID NO: 18 |
| 19 | H-DLys-DPhe-DGln-DPhe*-DGlu-DPhe-NH$_2$ | 2 | SEQ ID NO: 19 |
| 20 | H-Phe-Glu-Phe*-Lys-Phe-Ser-NH$_2$ | 1 | SEQ ID NO: 20 |
| 21 | H-Phe-Glu-Trp*-Gln-Phe-Lys-NH$_2$ | 2 | SEQ ID NO: 21 |
| 22 | H-DLys-DPhe-DAsn-DPhe*-DGlu-DPhe-NH$_2$ | 2 | SEQ ID NO: 22 |
| 23 | H-DLys-DPhe-DGlu-DPhe*-DGlu-DPhe-NH$_2$ | 2 | SEQ ID NO: 23 |
| 24 | H-DLys-DPhe-DGln-DPhe*-DGlu-DPhe-NH$_2$ | 2 | SEQ ID NO: 24 |
| 25 | H-DPhe-DGlu-DPhe*-DGln-DPhe-DLys-OH | 1 | SEQ ID NO: 25 |
| 26 | H-Lys-Phe-Gln-Phe*-Glu-Phe-OH | 2 | SEQ ID NO: 26 |
| 31 | H-Phe-Gln-Phe-Gln-Phe(3Br)-Lys-NH$_2$ | 1-2 | SEQ ID NO: 37 |
| 32 | H-Phe-Gln-Phe(3Br)-Gln-Phe(3Br)-Lys-NH$_2$ | 1-2 | SEQ ID NO: 38 |
| 33 | H-Phe(3Br)-Gln-Phe(3Br)-Gln-Phe(3Br)-Lys-NH$_2$ | 1-2 | SEQ ID NO: 39 |

TABLE 1-continued

Amphipathic α-peptide hydrogelators.

| alias | Sequence | Minimum gelation concentration (w/v % in PBS) | SEQ ID NO |
|---|---|---|---|
| 34 | H-Phe-Gln-Phe(3Br)-Gln-Phe-Lys-NH2 | 1-2 | SEQ ID NO: 40 |
| 35 | H-Phe(4Br)-Gln-Phe(4Br)-Gln-Phe(4Br)-Lys-NH$_2$ | 1-2 | SEQ ID NO: 41 |
| 36 | H-Phe-Gln-Phe-Gln-Phe(3I)-Lys-NH$_2$ | 1-2 | SEQ ID NO: 42 |
| 37 | H-Phe-Gln-Phe(3I)-Gln-Phe(3I)-Lys-NH$_2$ | 1-2 | SEQ ID NO: 43 |

In each of the peptides 1 to 26 and 31 to 37, a 13-(homo) amino acid could be built in at any position. In exemplary cases, a "Phe" or "DPhe" amino acid residue can be replaced by a "13$^1$-homo-Phe-Phe" or "13$^3$-homo-Phe-DPhe" combination, a "Trp" or "DTrp" amino acid residue can be replaced by a "13$^1$-homo-Trp-Trp" or "13$^3$-homo-Trp-DTrp" combination or a "Tyr" or "DTyr" amino acid residue can be replaced by a "13$^3$-homo-Tyr-Tyr" or "13$^3$-homo-Tyr-DTyr" combination. The replacement can be performed for any "Phe", "DPhe", "Trp", "DTrp", "Tyr" or "DTyr" amino acid residue present in the peptide. Preferably, said "Phe", "DPhe" or "Trp" amino acid residues are the "Phe", "DPhe" or "Trp" amino acid residues as indicated by an asterisk sign ('*') in Table 1. Specific examples are listed in Table 3 below.

Furthermore, in each of the peptides 1 to 26, one or more "Phe" or "DPhe" amino acid residues and/or one or more "Trp" or "DTrp" amino acid residues could be replaced by a halogenated "Phe" or "DPhe" amino acid residue or a halogenated "Trp" or "DTrp" amino acid residue, respectively. The halogen used for halogenation may be any halogen known in the art including Bromine, Iodine, Chlorine and Fluorine. Non-limiting examples of halogenated "Phe" amino acid residues are Phe(3Bromine) or Phe(3Br), Phe(4Br) or F(3Iodine) or Phe(3I), wherein the digit (e.g. 3 or 4) indicates the position of the halogenation on said amino acid. Specific examples are provided in peptides 31 to 37.

Peptide 2 possesses the same amino acid sequence as MBG-1 (FIG. 3, left), but the presence of an amide instead of an acid at the C-terminus increased the gel's pH from 3.49 to 4.02. The gelation of 2 occured by addition of phosphate buffered saline (PBS 10 mM; pH 7.4) at a concentration of 24 mM (2% w/v).

This indicated that the C-terminus could be altered without impeding hydrogel formation. In contrast, the addition of an acetyl group at the N-terminus, affording peptide 3 (Table 1), led to macroscopic aggregation under the same gelation conditions (PBS 10 mM; pH 7.4). This indicated that in this type of sequences the charge of the amine is necessary for self-assembly and stabilization of fibrous structures. Based on the premise that the free amine at the N-terminus was needed, while the C-terminal amide was tolerated for peptide self-assembly, the importance of aromaticity at the hydrophobic side of the 13-sheets was investigated next via replacement of Phe residues by aliphatic ones (peptides 5-9, Table 1). As the driving force of hydrogelation was amphipathicity in this family of peptides, the size, hydrophobic character and aromaticity of the amino acid side chains were considered. Among all these sequences, only peptides 5 and 9 (Table 1) formed gels at 2% w/v concentration in PBS, whereas analogues 6, 7 and 8 (Table 1) remained in solution.

These results could be explained by the relative lipophilicity of the composing amino acids. Indeed, at pH 7 Phe is classified as the most hydrophobic residue, followed by Iie, Leu, Val and Ala. The last sequence of this set, sequence 9 (Table 1), was designed to investigate the influence of aromaticity on the hydrogelation process. Cyclohexylalanine (Cha) is an unnatural amino acid, which can be regarded as the saturated version of Phe, with a significantly higher hydrophobicity. Although replacement of Phe by Iie or Cha still allowed formation of a hydrogel, the respective rheological data showed the formation of weaker gels, as compared to peptide 2 (Table 1) indicating that π-π stacking interactions are important for hydrogel formation.

The use of a-peptide hydrogelators, synthesized from natural amino acids, is extremely attractive for in vivo applications as such systems might easily be degraded by proteolytic enzymes, giving way to non-toxic amino acid and peptide segments. For application as drug delivery systems, peptide hydrogel systems can potentially also modulate release kinetics by alteration of the sequence. Control over drug-hydrogel fiber interactions and proteolytic degradation, could influence the release properties.

To achieve prolonged in vivo stability, unnatural amino acids such as D-amino acids or 13-amino acids could be used. The incorporation of D-amino acids, within amphipathic peptide hydrogelators, was reported beneficial for their biostability, but the most important challenge with such modifications consisted in retaining the gelling behavior. Indeed it was also reported that the switch of chirality from L to D of only one amino acid could disturb the self-assembly of 13-sheets, giving way to the loss of gel properties. Therefore, the synthesis of all-D sequence 4 (Table 1) was performed; wherein all L-amino acids were exchanged by the corresponding D-amino acids. Because hydrogelator peptides 2 and 4 (Table 1) presented the most promising physicochemical and gelation properties, subsequent in vitro and in vivo studies focused on these two sequences.

III) Conclusion

The Applicant developed a novel short amphipathic peptide-based hydrogel that formed a thixotropic or shear-thinning injectable gel under physiologically relevant conditions. The hydrophobicity of the amino acid side chains in these amphipathic peptides was varied and showed that aromaticity of the Phe residues was important for the formation of rigid hydrogels, as only cyclohexylalanine and isoleucine, bearing aliphatic side chains, could give way to a gel. Use of other aliphatic side chains resulted in no hydrogel formation or less rigid hydrogels.

Example 2: Characterization of Hydrogels for Co-Formulation

I) Materials and Methods

Rheology:
Dynamic rheometry measurements were performed on an AR-G2 rheometer (TA Instruments) equipped with electrically heated plates and a 10 mm-diameter aluminium parallel plate-plate geometry. Viscoelastic properties were measured by oscillatory frequency sweeps at 37° C. in the range between 0.01 and 10 Hz, using a controlled strain of 0.05%. Hydrogel samples were made 12 h in advance. A ring-shaped reservoir filled with a saturated $NH_4Cl$ solution was used as a solvent trap.

TEM:
Formvar carbon-coated 400-mesh copper grids (Agar Scientific, Stansted, United Kingdom) were treated with plasma using an ELMO Glow discharge system to clean the grid surface and to render the carbon surface hydrophilic. Hydrogel samples were prepared 12 h in advance as described above. Small aliquots of sample (5 μL) were pipetted onto the carbon grids for adsorption. After 30 s, excess of sample was removed by using a Whatman 541 filter paper. The loaded grids were stained during 10 s with 1% uranyl formate after which the grids were air-dried. Samples were analysed using a JEOL JEM-1400 transmission electron microscope, operating at accelerating voltage of 120 kV. Images were recorded on a CMOS TemCam-F416 camera and accessory software of TVIPS.

Cryo-TEM:
200-mesh copper grids coated with perforated carbon film (Lacey carbon film: ProSci-Tech Old, Australia) were used and were glow discharged in nitrogen for 5 s immediately prior to use. Hydrogel samples were prepared 12 h in advance as described above. Small aliquots of sample (4 μL) were pipetted onto the carbon grids for adsorption. After 30 s, excess of sample was removed by using a Whatman 541 filter paper. The grid was then plunged into liquid ethane cooled by liquid nitrogen. Frozen grids were stored in liquid nitrogen until required. Samples were analysed using a Gatan 626 cryoholder and Tecnai 12 Transmission electron microscope, operating at accelerating voltage of 120 kV. Images were recorded using an FEI Eagle 4k×4k CCD camera.

II) Results

The first step to characterize the hydrogels formed by the peptide hydrogelators consisted of applying the qualitative tilted tube method, in order to demonstrate the formation of a self-supporting gel. Both peptides 2 and 4 (Table 1) gave a transparent gel in the same conditions (PBS 10 mM at pH 7.4 with a minimum gelation concentration of 24 mM; 2% w/v). To evaluate the mechanical properties of these hydrogels in a more quantitative manner, rheological experiments were performed. The viscoelastic properties of the peptide hydrogels were measured by dynamic rheometry at 37° C. This technique allowed to measure the storage modulus G' (corresponding to the material's stiffness or rigidity), loss modulus G" (corresponding to the viscous properties of the material) and loss factor tan (o) (ratio of G" over G'). According to the Winter-Chambon criterion, a material reaches gelation in rheological terms if the phase angle o gets frequency-independent (F. Chambon et al., 1987 and H. Winter et al., 1987). However, the profiles of the peptide hydrogels showed a declining o as a function of frequency, corresponding to 'structured fluids' or 'weak gels', according to rheology (D. R. Picout et al., 2003).

Figure 6:
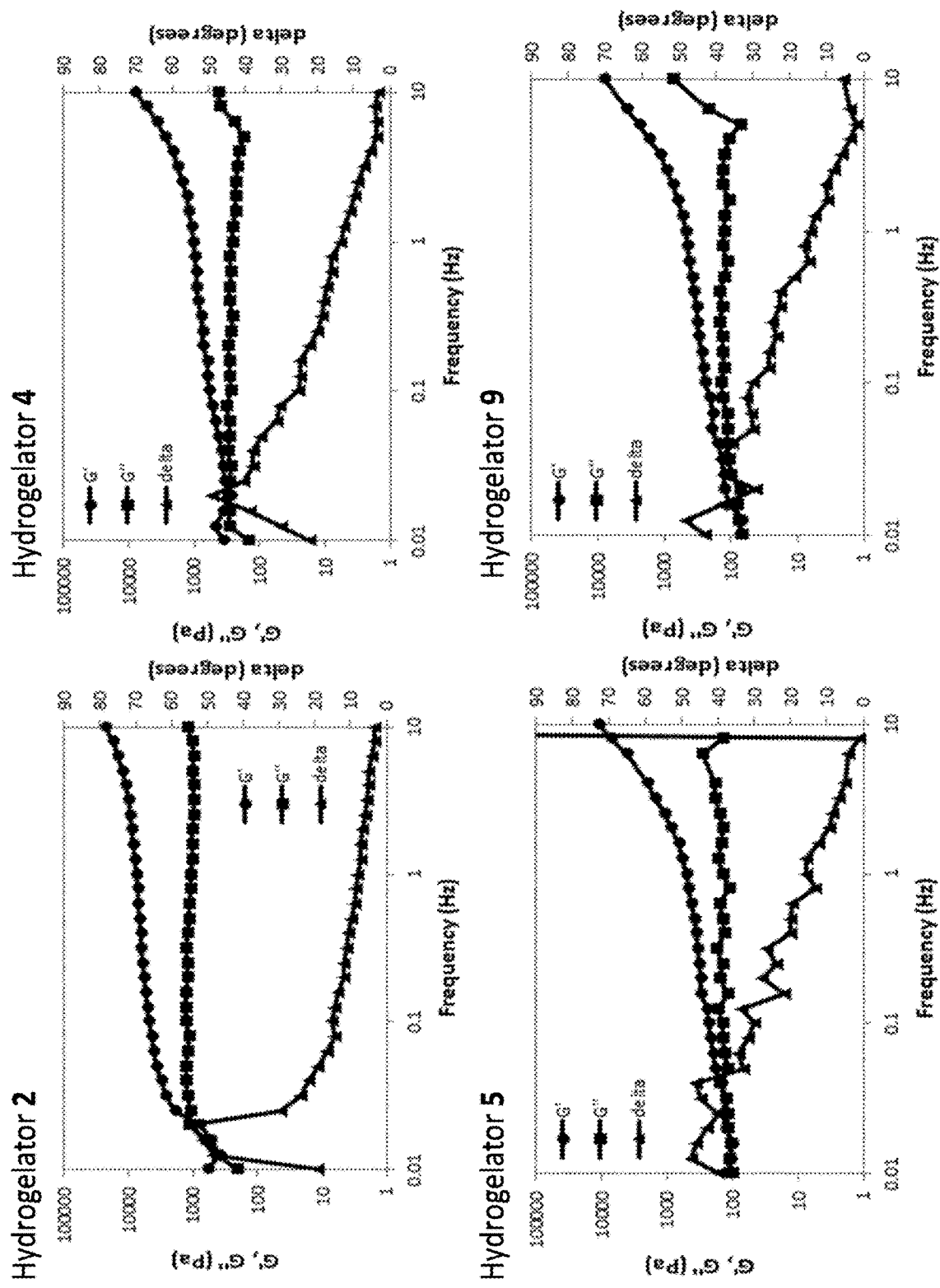
FIG. 6 represents the dynamic frequency sweep data for the amphipathic peptide hydrogelators 2, 4, 5 and 9 at a concentration of 2% w/v in PBS.

Peptide hydrogel 2 (Table 1) showed a G' value of ca. 8000 Pa (FIG. 6, value taken at a frequency of 1 Hz), comparable to its precursor MBG-1, which was described as a rather rigid hydrogel (M. Bibian et al., 2015). Hydrogelator peptide 4 (Table 1; FIG. 6) gave way to a less rigid hydrogel, having a G' value of ca. 1000 Pa.

Figure 7:
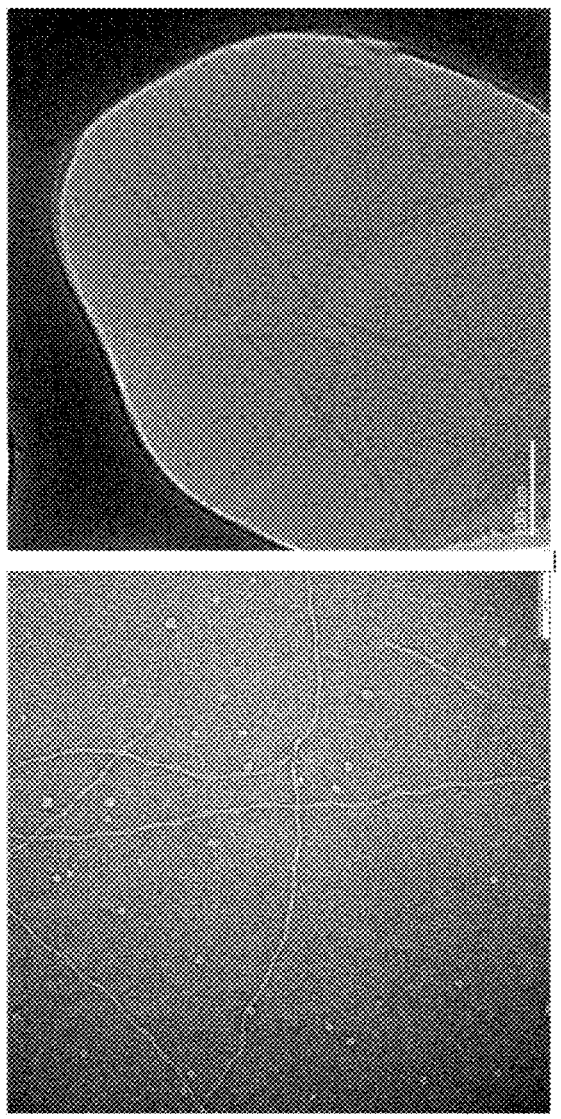
FIG. 7 represents the TEM image with negative staining of amphipathic peptide hydrogelator 2 (left, scale bar 70 nm) and cryogenic TEM picture for hydrogel formed by amphipathic hydrogelator peptide 4 (right, scale bar 200 nm).

In addition, transmission electron microscopy (TEM) was used to investigate the fiber morphology of the resulting hydrogels. For the hydrogels based on peptides 2 and 4 (Table 1), long, entangled fibers were observed, forming the hydrogel network (FIG. 7). Peptide hydrogelator 2 (Table 1) formed fibrils having a clear twist, whereas all-D peptide 4 (Table 1) forms straight fibers. Both hydrogels formed by said peptides contain fibers having a comparable thickness of ca. 10 nm.

III) Conclusion

Peptide 2 and its all-D counterpart 4 were characterized by TEM revealing the formation of nanofibrillar hydrogel networks which could be used for the entrapment and controlled release of drugs.

Example 3: In Vitro Stability of Hydrogels for Co-Formulation

I) Materials and Methods

Human plasma was obtained from the Belgian Red Cross (Vlaams-Brabant, Leuven). Prior to the stability test, selectivity, stability of the compound in the injection solvent, the effect of various incubation times at 4° C., linearity, accuracy and precision of the method were investigated. Frozen (−20° C.) human plasma samples were thawed and thermostated to 37+2° C. Dissolution of the lyophilized peptide and consecutive dilutions were performed in water. The resulting aqueous solutions of hydrogelator peptides 2 and 4 (Table 1) were spiked in human plasma (10:90 v/v) with final plasma concentrations of 72 μM, respectively. During the plasma stability study, samples were taken after 0, 5, 10, 15, 30, 60, 90, 120, 240, 1500 and 5700 min for hydrogelator peptide 4 (Table 1) and 0, 5, 10, 15, 30, 60, 90 and 120 min for hydrogelator peptide 2 (Table 1). On every time point 100 μL spiked plasma was transferred to a 500 μL Eppendorf tube and a protein crash was performed using 300 μL methanol+0.1% TFA (4° C.). Suspensions were vortexed for 15 seconds and placed at 4° C. for 30 to 45 minutes. After centrifugation at 14000 rpm for 20 minutes, 100 μL supernatant was diluted with 100 μL water in the injection vial. Injection samples were vortexed for 5 seconds and placed in the autosampler. For the calculation of the peptide half-life, only points with an area under the curve (AUC) higher than the AUC of the lowest standard were used. Concentrations were calculated by use of the calibration curve and transferred to a semi-log chart presenting the log concentrations as a function of time. The optimum curve was used to calculate the peptide-half life. Calculations were performed using Microsoft® Office Professional 2010 Excel.

II) Results

The stability (defined as half-life, $t_{1/2}$) of the peptide hydrogels in human plasma at 37° C. was investigated for hydrogelator peptides 2 and 4 (Table 1). While the half-life of hydrogelator peptide2 (Table 1) was calculated to be around 15 min (FIG. 8), the corresponding C-terminal carboxylic acid presented a half-life of approximately 2 min. Improved plasma stability is commonly observed for C-terminal carboxamides. However, no half-life could be determined for the sequence containing D-amino acids.

As expected, after 4 days of incubation with human plasma, all-D-analogue hydrogelator peptide 4 (Table 1) remained intact. The straightforward use of D-amino acids to synthesize stabilized peptide-based hydrogelator induced an exceptional increase of resistance towards proteolytic degradation.

Example 4: In Vitro Release Experiments of the Co-Formulation

I) Materials and Methods

Loaded drug delivery system was prepared by addition of 100 µL of PBS solution containing morphine hydrochloride with a concentration of 0.1% w/v on 2 mg peptide hydrogelator in an Eppendorf of 1.5 ml. PBS (0.5 ml) was gently added on the top of the resulting loaded hydrogel. This last step was the starting point for the kinetic monitoring. At selected time points, aliquots (10 µL) of the supernatant PBS were taken and were replaced by fresh PBS. For each sample, UV spectra (using analytical HPLC) were recorded and the absorbance signal was integrated at 215 nm. The percentage release profile of morphine was obtained by plotting the percent fraction as a function of time. The experiments were repeated in triplicate, and allowed to calculate the error bars.

II) Results

The ability of peptide hydrogels formed from hydrogelator peptides 2 and 4 (Table 1) to release bioactive molecules was first studied via in vitro experiments. These consisted of a static drug release from the hydrogel within an Eppendorf, using PBS as a physiologically relevant medium. Even though these experiments were not equivalent to behavior in in vivo environments, especially because no proteases were present, they gave an idea of the peptide's capacity to retain the investigated drugs. In the applied in vitro setting, the geometry of the sample, the aliquoting method, the volume of acceptor medium, and the hydrogel swelling/degradation/erosion properties determined the release profile.

As morphine is the most commonly analgesic drug clinically used to date for chronic pain management (Portenoy et al., 2002), it was chosen as an opioid agonist cargo to gain first insights into the release kinetics from the hydrogels described above. Additionally, a structurally related opioid antagonist, naloxone, was included in the study as well. The controlled release of mixed opioid agonist-antagonist systems (e.g. oxycodone-naloxone formulations) has been investigated for treatment of chronic low back pain, and hence this cargo molecule is also clinically relevant (Cloutier et al., 2013).

Figure 4:
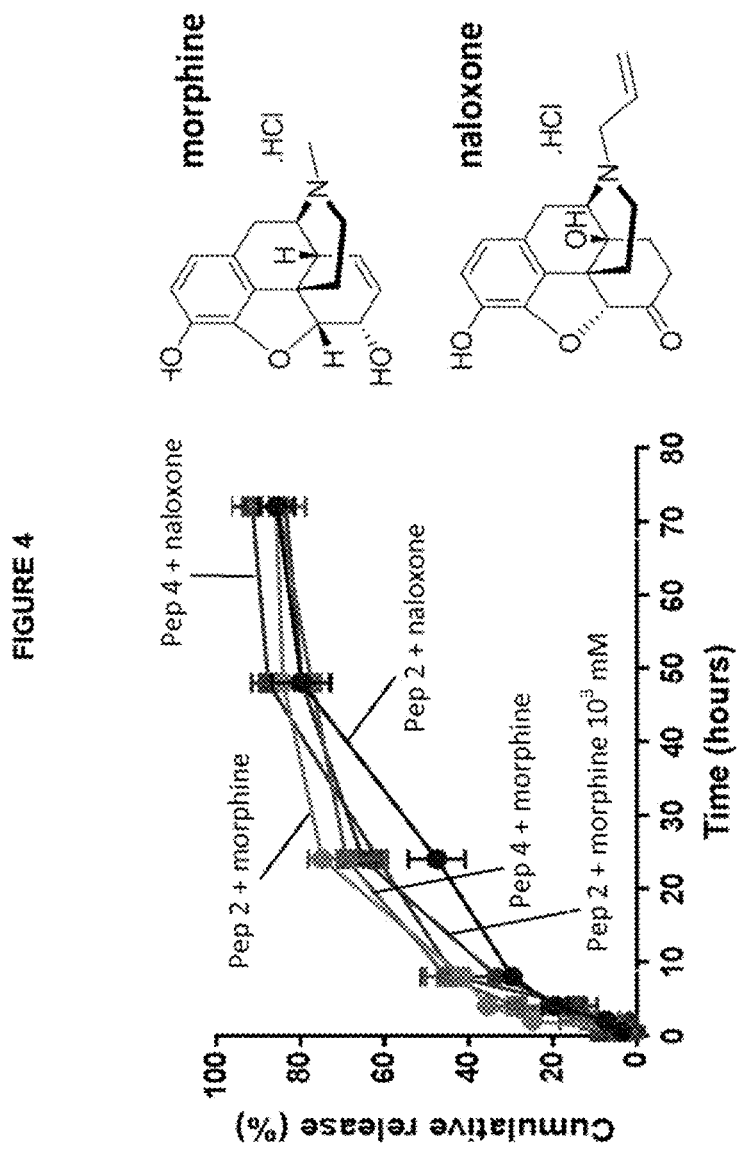
FIG. 4 represents the release profiles of morphine hydrochloride (3.1 mM; 0.1% w/v) and naloxone hydrochloride (0.5 mM; 0.02% w/v) from the self-assembled peptide hydrogels formed by amphipathic hydrogelator peptide 2 (graphs with circles 2% w/v,) and 4 (graphs with squares 2% w/v) and morphine hydrochloride (103 mM; 3.3% w/v) from hydrogelator 2 (2% w/v,) in PBS (10 mM, pH 7.4) at room temperature using a static release model. Data points represent the average of 3 samples with calculated error bars.

Morphine was solubilized in PBS to obtain a solution with a concentration of 3.1 mM (0.1% w/v). The resulting solution was directly added to the peptidic hydrogelator in an Eppendorf, to construct the drug delivery system loaded with morphine hydrochloride and ready for the release study. In this release model, hydrogels were gently covered with PBS. From this moment, the sampling of supernatant aliquots at regular time points started, and the samples were replaced with fresh PBS to keep a constant volume. HPLC measurements at 215 nm were performed, allowing to plot the percentage of released morphine hydrochloride as a function of time based on a calibration curve (FIG. 4). Overall, the morphine in vitro release profiles were characterized by a rapid initial release during the first hours (i.e. a burst effect), followed by a sustained release over 3 days resulting in a recovery of about 90%.

Interestingly, an increase of the morphine concentration to 3.3% w/v did not influence the release profile. This small burst effect (approximately 20%) could be attributed to fast morphine diffusion through the large pores of the hydrogel, the release of molecules which were weakly associated to the network, and/or the rapid evasion of drug molecules present at the surface of the hydrogel. This phenomenon caused considerable release at the initial stage, but should not necessarily be considered as a drawback. In fact, a moderate burst effect may be useful to provide immediate pain relief, followed by a prolonged therapeutic effect (X. Huang et al., 2001).

Comparison between the 'native' sequence of hydrogelator peptide 2 and the sequence of more stable hydrogelator peptide 4 (Table 1), both at room temperature, showed almost identical release rate of morphine, which may have been anticipated as no proteases were present. The influence of temperature (physiological temperature 37° C.) on the kinetic of morphine, release was also investigated for both hydrogelators at 2% w/v concentration (data not shown). At physiological temperature, the same release profiles were obtained. These in vitro release curves of morphine held promise for subsequent in vivo experiments.

Example 5: Biological Evaluation: Cytotoxicity and Antinociceptive Effect of the Co-Formulation A) Cytotoxicity I) Materials and Methods Cell viability Assay:

L929 (mouse fibroblast) cells were obtained from ATCC® and maintained in Gibco®, MEM with GlutaMAX supplemented with 10% FBS (SAFC, Sigma), 1% Anti-Anti (100x, Gibco®) and 1% NEAA (100x, Gibco®). Cells were maintained on tissue culture treated polystyrene (TCPS) plates at 37° C. in a humified atmosphere containing 5% $CO_2$ and 95% air. Cells were trypsinized, harvested and counted using a hemocytometer. The resulting cell suspension was diluted in Gibco® solution before addition to the hydrogels. For ease of handling and to produce homogeneous clear hydrogels, 100 µL of peptide hydrogels were prepared (in corresponding gelation conditions, see above) in Eppendorf tubes (0.5 ml) and transported using a 21G syringe to 96-well plates after simultaneously heating (60° C.) and mixing (900 rpm) using an Eppendorf ThermoMixer®. The hydrogels were left to set overnight in the wells at room temperature and were subsequently washed twice with 200 µL of Anti-Anti (100x, Gibco®) solution, 2 h each. After washing, media was removed and cells were seeded evenly over hydrogels. Cells were plated in duplicate on all hydrogels and control wells. Viability of cells on hydrogels was determined using the traditional Live/dead cell viability assay (Invitrogen) after culture durations of 24 h.

Live/Dead Cell Viability Assay:

Cells were plated in duplicate ($1\times10^5$ cell/well in 16 well plates) on control TCPS culture plate, control ULA plate and ULA plate containing the nanostructured hydrogels (including hydrogelator peptide 2, hydrogelator peptide 4 (Table 1)). Plates were incubated in 5% $CO_2$ at 37° C. for 1 day to allow cell attachment and spreading to occur. Live/dead cell viability assay was done using LIVE/DEAD® Viability/Cytotoxicity Kit *for mammalian cells* (Invitrogen) as per the manufacturer's instructions. Details of the assay are provided in the Supporting Information.

II) Results

Optical microscopy images of L929 cells grown on 96 well plates coated with peptide hydrogels formed by hydrogelator peptide 2 and 4 (Table 1) for a period of 24 h, showed cells with a somewhat rounded morphology (see FIG. 9), indicating that the cells did not spread on the peptide hydrogels, in contrast to the cells of the control TCPS plates (FIG. 9-B). The cytotoxicity of the hydrogels was qualitatively assessed using the Live/Dead cell viability assay (Invitrogen, see FIG. 9-C and 9-D) after 24 h of cell culturing on peptide hydrogels. For peptide hydrogel formed by hydrogelator peptide 2; this assay showed that the majority of cells were green fluorescent and thus, were viable in a similar way to those cultivated on control ULA (ultra-low adherence) plates (see FIG. 9-A). This peptide hydrogel can therefore be considered as biocompatible.

B) Nociceptive Assessment

I) Materials and Methods

Figure 5:
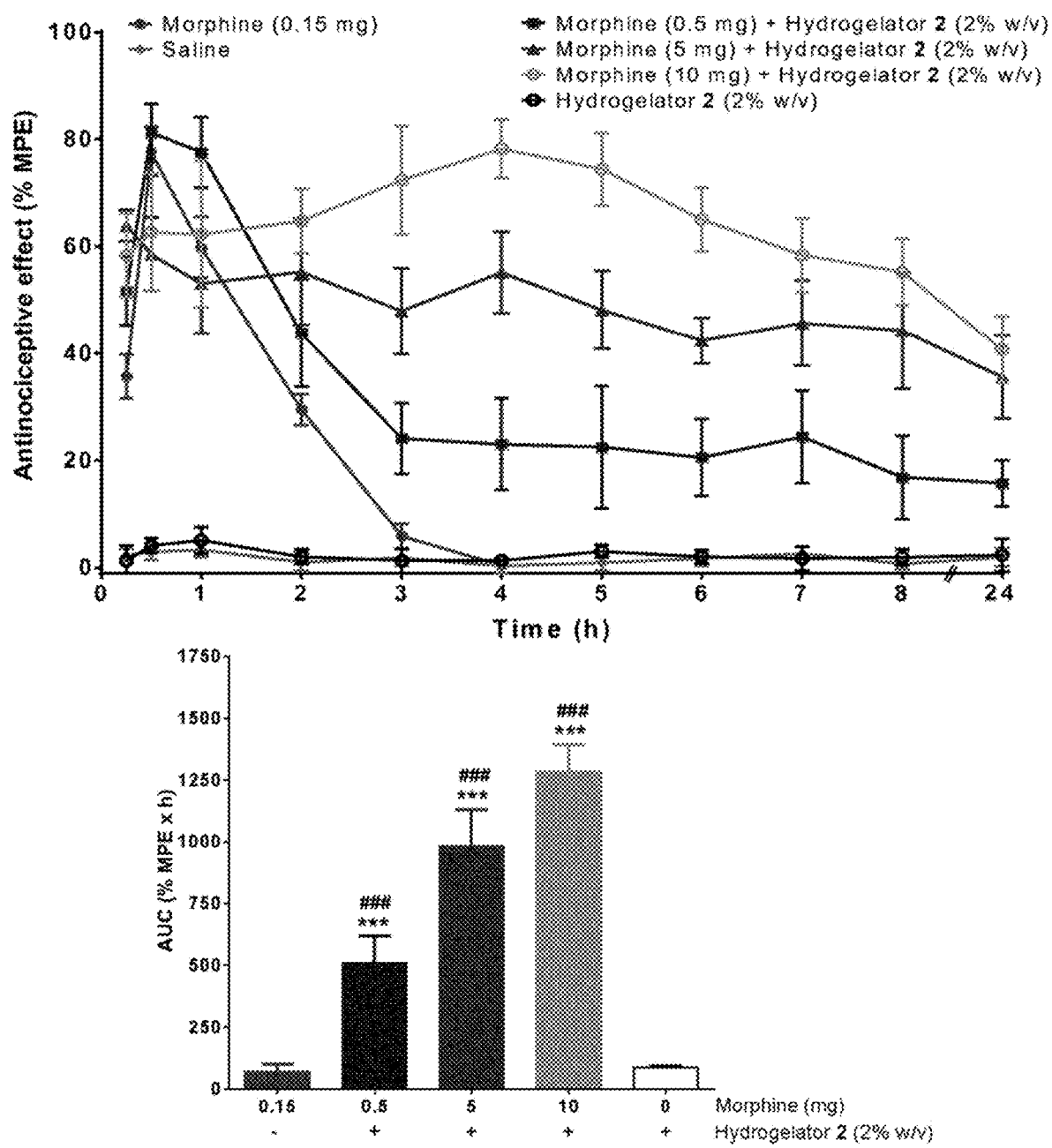
FIG. 5 represents the antinociceptive effects of morphine in the mouse tail-flick test after s.c. administration, applied in solution or co-formulated with hydrogel formed by amphipathic hydrogelator peptide 2 (2% w/v). Left panel: Time course of the antinociceptive response as % of Maximum Possible Effect (% MPE). Right panel: Areas under the curves (AUC) of the respective time curves. Doses of morphine are given per mouse. Data are the mean±SEM of 5 to 10 mice per group. ***$p<0.001$ vs. group treated with morphine in solution, ###$p<0.001$ vs. control group treated only with hydrogel formed by amphipathic hydrogelator peptide 2 (2% w/v) (ANOVA with Tukey's post-hoc test).

Animals and Drug Administration:

Male CD1 mice (6-8 weeks old, body weight average 30 g) were obtained from Charles River (Sulzfeld, Germany). Mice were group-housed in a temperature controlled room with a 12 h light/dark cycle and with free access to food and water. All animal studies were conducted in accordance with ethical guidelines and animal welfare standards according to Austrian regulations for animal research, and were approved by the Committee of Animal Care of the Austrian Federal Ministry of Science and Research. Groups of mice were s.c. administered either (1) morphine (Gatt-Koller GmbH, Innsbruck, Austria) dissolved in sterile physiological saline (0.9%) as bolus in a dose of 5 mg/kg (corresponding to 0.15 mg per mouse, volume of 10 µl/g body weight), (2) morphine (0.5, 5 or 10 mg per mouse, in a volume of 150 µl) formulated with hydrogelator peptide 2 (2% w/v) in physiological saline or (3) saline or hydrogelator peptide 2 (2% w/v) (Table 1) only used as controls (FIG. 5).

Each experimental group included five to ten animals.

Tail-Flick Test:

The radiant heat tail-flick test was used to assess antinociceptive effects of tested drugs after s.c. administration in mice using an UB 37360 Ugo Basile analgesiometer (Ugo Basile s.r.l., Varese, Italy) as described previously (A. Novoa et al., 2012). The reaction time required by the mouse to remove its tail due to the radiant heat was measured and defined as the tail-flick latency. A cut-off time of 10 s was also used in order to minimize tissue damage. The antinociceptive response was expressed as percent of Maximum Possible Effect (% MPE)=[(TL-BL)/(cut-off time-BL)]× 100. Data were analyzed with ANOVA using Tukey's multiple comparison test, and graphically processed with the GraphPad Prism Software (GraphPad Software Inc., San Diego, CA).

II) Results

Figure 3:
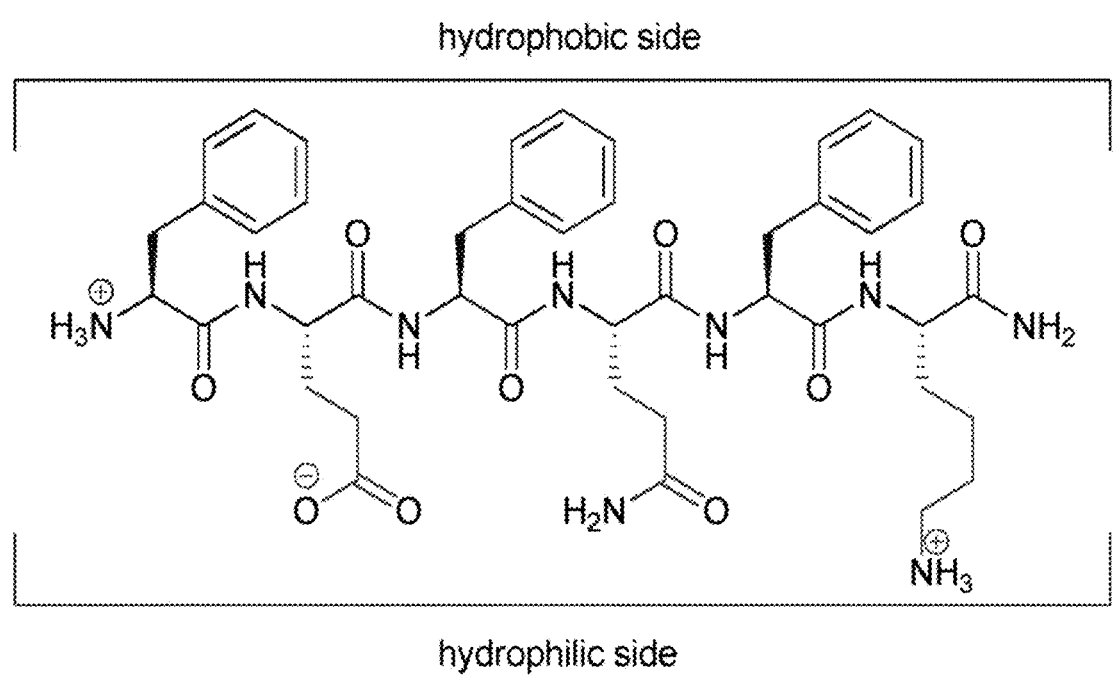
FIG. 3 represents the structure of amphipathic hydrogelator peptide 2 at pH 7.4 (left) and immediate re-gelation after injection through a 25G needle used for s.c. injections (right).
Figure 10:
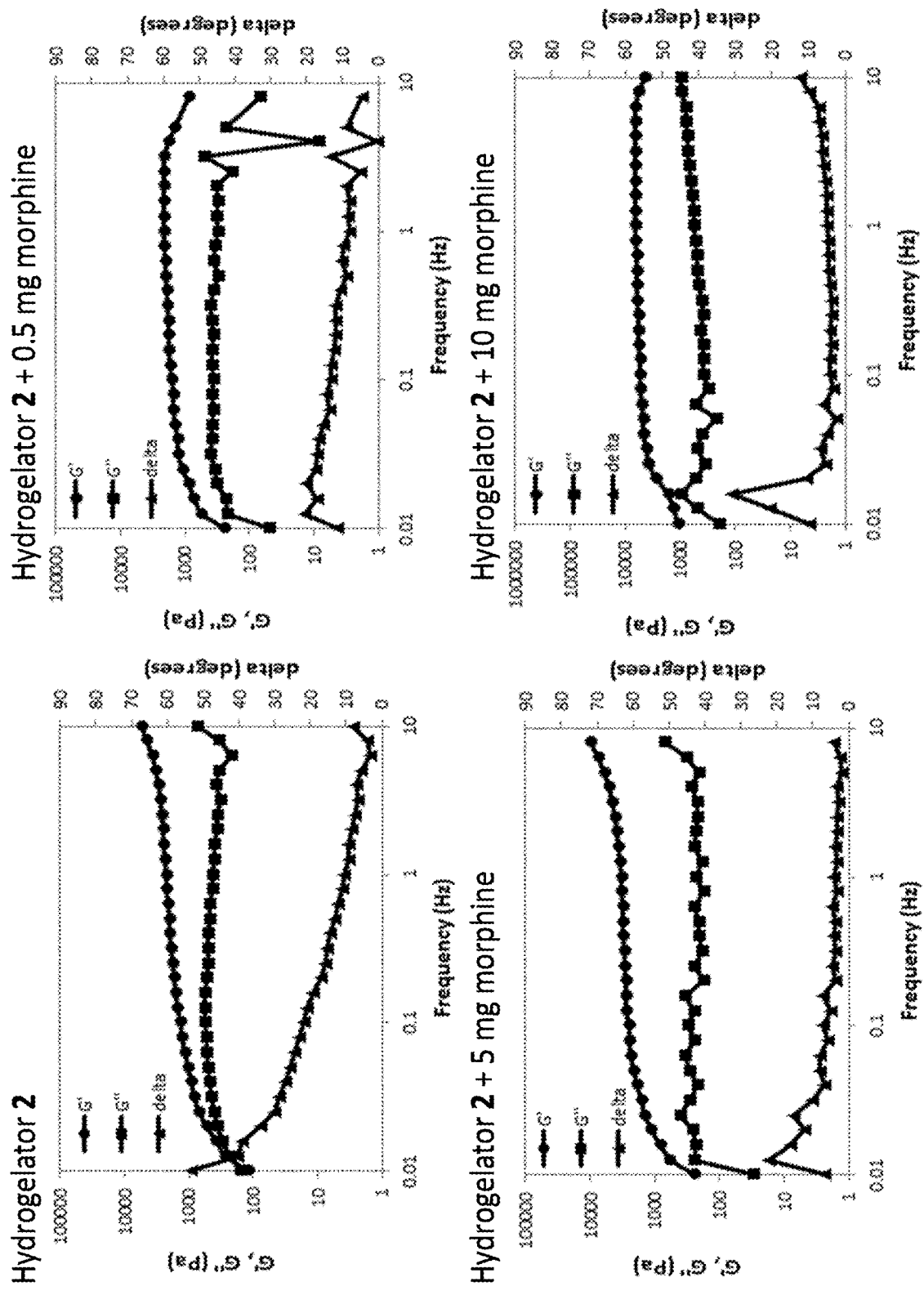
FIG. 10 represents the dynamic frequency sweep data for the amphipathic peptide hydrogelator 2 (2% w/v) and amphipathic peptide hydrogelator 2 (2% w/v) co-formulated with 0.5 (10.3 mM), 5 (103 mM) and 10 mg (206 mM) of morphine in physiological saline.

Prior to the planned in vivo experiments, the injectability of the hydrogels was tested and confirmed by the use of a 25G needle destined for s.c. injections (see FIG. 3). The mechanical properties of hydrogels resulting from the co-formulation of morphine with hydrogelator peptide 2 (Table 1) were also investigated (FIG. 10). Upon loading 0.5 mg of morphine (0.3% w/v), a G' value comparable to the one of a hydrogel without cargo was obtained (ca. 2200 Pa). In contrast, higher morphine concentrations (5 mg and 10 mg, corresponding to 3.3% and 6.6% w/v) increased the gels' rigidity (G' of 3400 Pa and 6500 Pa, resp.). The increased stiffness of the hydrogels could be explained by hydrophobic interactions between morphine and the hydrogelator. Next, the in vivo efficiency of hydrogelator peptide 2 (Table 1) as a drug delivery platform was investigated through controlled release experiments of morphine.

Morphine's relatively short duration of analgesic action, rendered it a suitable model to evaluate prolonged effects generated by co-formulation with hydrogelator peptide 2 (Table 1). The therapeutic antinociceptive effect was investigated in a model of thermal nociception using the tail-flick test in mice (FIG. 5). In this set of experiments, morphine was injected s.c. in solution or co-formulated with hydrogelator peptide 2 (Table 1), following the same protocol as described above for the in vitro release study (i.e. using physiological saline solution). First, the Applicant selected a dose of morphine of 5 mg/kg, which produces an antinociceptive effect corresponding to 80% of Maximum Possible Effect (% MPE). As shown in FIG. 5, morphine administered s.c. in bolus at a dose of 5 mg/kg produces a marked antinociceptive response with a peak of action at 30 min which declined rapidly thereafter, with no effect detected at 3 h after drug administration. This dose of morphine, corresponding to a dose of 0.15 mg per mouse, served as a reference to compare the influence of hydrogelator peptide 2 (Table 1) as a novel drug delivery system. Since higher doses are typically applied when sustained release devices are used compared to bolus injections, to reach prolonged therapeutic effects, the first tested dose per mouse consisted of a co-formulation including 0.5 mg of morphine and hydrogelator peptide 2 (Table 1) at a concentration of 2% w/v (FIG. 5). This formulation led to a minor improvement of the maximal possible effect from 3 h post-injection onwards. An extended, but limited effect detectable up to 24 h was noticed (ca. 20% of MPE). These experiments indicated that a threefold increase of morphine dose did not suffice to extend the antinociceptive response. Hence, the dose of morphine in co-formulation with hydrogelator peptide 2 (2% w/v) (Table 1) was increased. At both tested doses of 5 mg and 10 mg per mouse (FIG. 5) the desired extended release profiles were obtained, with an antinociceptive effect of ca. 40% MPE for the 10 mg dose, after 24 h.

Upon application of higher doses (5 and 10 mg/150 µL) the peak antinociceptive effect was absent or much delayed. This observation could potentially be related to the increased gel stiffness, resulting from higher drug loadings (vide supra). One remarkable advantage of the current formulation is the large drug loading capacities that are possible (up to ca. 77%) with this type of peptide hydrogelator, yet keeping the injectable gel properties. Higher doses were not considered given the limited solubility of morphine. Notably, apart from a slight increase in motor activity, no sedative effects or other typical opioid side effects were observed in mice, even upon application of the highest injected dose of morphine co-formulated with hydrogelator peptide 2 (Table 1).

III) Conclusion

The Applicant showed the noncytotoxic nature of the hydrogelator peptide 2. The beneficial role of the hydrogel formulations, in comparison with bolus injections in solution was clearly established via monitoring of morphine's antinociceptive effect in mice using the tail-flick test model after subcutaneous injection. The high drug loading capacity (up to ca. 77%) of the peptide-hydrogel system allowed to maintain a significant antinociceptive effect of around 40% of MPE after 24 h, without major alterations in the general behavior of mice during treatment. The absence of adverse effects was indicative of the high stability of the hydrogel after s.c. injection. Because of the growing burden of chronic pain on the society, efficient and economically viable formulations used for prolonged pain treatment remain of high interest. The presented hydrogels could serve as a drug delivery platform, and can clearly be applied beyond the development of extended release formulations of analgesics.

Example 6: Design and Synthesis of Biogel Compositions

I) Materials and Methods

Peptide Synthesis:

Peptides were synthesized according to the standard solid-phase peptide synthesis method (W. Chan et al., 2000). Peptide purification was performed using preparative reverse high-performance liquid chromatography.

Peptide Gelation:

The peptide gelation occurred by dissolving the TFA salt of the peptide in 100 µL of PBS solution or physiological saline solution (0.9% NaCl) (pH 7.4).

II) Results

The design of biogel compositions (Table 2) was based on the sequence H-Phe-Glu-Phe-Gln-Phe-Lys-NH2 (SEQ ID NO: 2, Table 1) or H-Phe-Gln-Phe-Gln-Phe-Lys-NH$_2$ (SEQ ID NO: 16, Table 1), which presented very promising results in terms of in vivo controlled release of model cargoes.

The self-assembly process of biogel composition was influenced by different parameters such as the side chain hydrophobicity, ionic charges and the secondary structure propensity of the sequence. Indeed, formation of the 13-sheets that underpin hydrogelation occurred by hydrogen-bonding, noncovalent ionic and hydrophobic interactions between the side chains of the amino acids.

TABLE 2

| Codes | Sequences | Binding tests (Ki) in nM | | | Seq ID NO |
|---|---|---|---|---|---|
| | | MOR | DOR | KOR | |
| CM-53 | Dmt-DLys-Phe-Phe-Glu-Phe*-Gln-Phe-Lys-NH2 | 7.4 | 24 | 337 | SEQ ID NO: 27 |
| CM-54 | Dmt-Pro-Phe-Phe-Glu-Phe*-Gln-Phe-Lys-NH2 | 135 | 112 | — | SEQ ID NO: 28 |
| CM-56 | Dmt-Pro-Phe-Phe-Gln-Phe*-Gln-Phe-Lys-NH2 | 65 | 176 | 337 | SEQ ID NO: 29 |
| CM-57 | Dmt-DArg-Phe-Phe-Gln-Phe*-Gln-Phe-Lys-NH$_2$ | 2.7 | 216 | 112 | SEQ ID NO: 30 |
| CM-58 | Dmt-Pro-Trp-Phe-Gln-Phe*-Gln-Phe-Lys-NH$_2$ | 7.5 | 15 | 120 | SEQ ID NO: 31 |
| CM-59 | Dmt-OArg-Aba-BAla-Phe-Gln-Phe*-Gln-Phe-Lys-NH2 | 6.96 | — | — | SEQ ID NO: 32 |
| EO-19 | Dmt-OArg-Phe-Phe-Glu-Phe*-Gln-Phe*-Lys-NH2 | — | — | — | SEQ ID NO: 44 |
| EO-20 | Dmt-OArg-Phe-Phe-Lys-Phe*-Gln-Phe-Glu-Phe*-NH2 | — | — | — | SEQ ID NO: 45 |
| EO-35 | Dmt-OArg-Phe-Phe-DLys-DPhe*-DGln-DPhe-DGlu-DPhe*-NH2 | — | — | — | SEQ ID NO: 46 |
| EO-21 | Dmt-OArg-Phe-Phe-Glu-Trp*-Gln-Trp*-Lys-NH2 | — | — | — | SEQ ID NO: 47 |
| CM-136 | Dmt-OLy:s-Phe-Phe-Gln-Phe*-Gln-Phe*-Lys-NH2 | — | — | — | SEQ ID NO: 48 |
| CM-137 | Dmt-OArg-Phe-Phe-Gln-J3;s-homo-Phe-Phe-Gln-Phe*-Lys-NH2 | — | — | — | SEQ ID NO: 49 |
| CM-138 | Dmt-OArg-Phe-Phe-Gly-Gly-Gln-J3'''-homo-Phe-Phe-Gln-Phe*-Lys-NH2 | — | — | — | SEQ ID NO: 50 |
| MM-01 | Ty:r-OArg-Phe-Phe-Gln-Phe*-Gln-Phe*-Lys-NH2 | — | — | — | SEQ ID NO: 51 |
| MM-02 | Ty:r-OArg-Phe-Phe-Gln-Phe*-Gln-Phe-Lys-Phe-Gln-Phe-Gln-Phe*-Lys-NH2 | — | — | — | SEQ ID NO: 52 |

TABLE 2-continued

| Codes | Sequences | Binding tests (Ki) in nM | | | Seq ID NO |
|---|---|---|---|---|---|
| | | MOR | DOR | KOR | |
| MM-04 | Dmt-OArg-Phe-Phe-Gln-Phe*-Gln-Phe-Lys-Phe-Gln-Phe-Gln-Phe-Lys*-NH2 | — | — | — | SEQ ID NO: 53 |
| MM-06 | Dmt-OArg-Phe-Phe-Trp-Gln-Trp*-Gln-Trp*-Lys-NH2 | — | — | — | SEQ ID NO: 54 |
| CM-75 | Dmt-OArg-Tq2-Tr-Gln-Trp*-Gln-Trp*-Lys-NH2 | — | — | — | SEQ ID NO: 55 |
| MOJ-02 | Ty:r-OArg-Phe-Phe-Gln-J3'''-homo-Phe-Phe-Gln-Phe*-Lys-NH2 | — | — | — | SEQ ID NO: 56 |

Wherein the underlined and bold amino acid residues are shared by the hydrogelator part and the active ingredient/analgesic.

In each of the peptides CM-53, CM-54, CM-56, CM-57, CM-58, CM-59, EO-19, EO-20, EO-35, EO-21, CM-136, MM-01, MM-02, MM-04, MM-06 or CM-75, a l3-(homo) amino acid could be built in at any position. Preferably, the l3-(homo) amino acid is built into the hydrogelator part of the biogel composition which is represented by the bold amino acid sequences in Table 2. In exemplary cases, a "Phe" or "DPhe" amino acid residue can be replaced by a "$13^1$-homo-Phe-Phe" or "$13^3$-homo-Phe-DPhe" combination, a "Trp" or "DTrp" amino acid residue can be replaced by a "$13^3$-homo-Trp-Trp" or "$13^3$-homo-Trp-DTrp" combination, or a "Tyr" or "DTyr" amino acid residue can be replaced by a "$13^1$-homo-Tyr-Tyr" or "$13^3$-homo-Tyr-DTyr" combination. Preferably, said "Phe" or "DPhe" amino acid residues which are replaced by a "$13^3$-homo-Phe-Phe" or "$13^3$-homo-Phe-DPhe" combination, said "Trp" or "DTrp" amino acid residue which are replaced by a "$13^3$-homo-Trp-Trp" or "$13^1$-homo-Trp-D Trp" combination, or said "Tyr" or "DTyr" amino acid residue which are replaced by a "$13^3$-homo-Tyr-Tyr" or "$13^3$-homo-Tyr-DTyr" combination are located in the hydrogelator part of the biogel composition which are represented by the bold amino acid sequences in Table 2. More preferably, said "Phe" or "DPhe" amino acid residues are preferably the "Phe" or "DPhe" amino acid residues as indicated by an asterisk sign ("*") in Table 2. Wherein Aba represents 4-Amino-1,2,4,5-tetrahydro-2-benzazepinone. Wherein Dmt represents 2',6'-dimethyl-L-tyrosine. Wherein the underlined part is the active ingredient/analgesic.

Example 7: Antinociceptive Effect of Biogel Compositions In Vivo

A) Subcutaneously Injected in Solution

I) Materials and Methods

Animals and Drug Administration:

Male CD1 mice (6-8 weeks old, body weight average 30 g) were obtained from Charles River (Sulzfeld, Germany). Mice were group-housed in a temperature controlled room with a 12 h light/dark cycle and with free access to food and water. All animal studies were conducted in accordance with ethical guidelines and animal welfare standards according to Austrian regulations for animal research, and were approved by the Committee of Animal Care of the Austrian Federal Ministry of Science and Research. Groups of mice were s.c. administered 'biogel compositions dissolved in sterile physiological saline (0.9% NaCl) as bolus in a dose of (1) 1 mg/kg (corresponding to 0.03 mg per mouse, volume of 10 µl/g body weight), (2) 5 mg/kg (corresponding to 0.15 mg per mouse, volume of 10 µl/g body weight) and (3) 10 mg/kg (corresponding to 0.30 mg per mouse, volume of 10 µl/g body weight). Each experimental group included five to ten animals.

Tail-Flick Test:

The radiant heat tail-flick test was used to assess antinociceptive effects of tested drugs after s.c. administration in mice using an UB 37360 Ugo Basile analgesiometer (Ugo Basile s.r.l., Varese, Italy) as described previously (A. Novoa et al., 2012). The reaction time required by the mouse to remove its tail due to the radiant heat was measured and defined as the tail-flick latency. A cut-off time of 10 s was also used in order to minimize tissue damage. The antinociceptive response was expressed as percent of Maximum Possible Effect (% MPE)=[(TL-BL)/(cut-off time-BL)]×100. Data were analyzed with ANOVA using Tukey's multiple comparison test, and graphically processed with the GraphPad Prism Software (GraphPad Software Inc., San Diego, CA).

II) Results: Nociceptive Assessment

Tests were performed for hydrogels (biogels) based on peptides CM-53, CM-57, CM-58 and CM-59 (Table 2), for which the ideal doses in solution were determined to be 2.5 mg/kg and 5 mg/kg, respectively (FIG. 11).

B) Subcutaneously Injected as a Gel

I) Materials and Methods

Animals and Drug Administration:

Male CD1 mice (6-8 weeks old, body weight average 30 g) were obtained from Charles River (Sulzfeld, Germany). Mice were group-housed in a temperature controlled room with a 12 h light/dark cycle and with free access to food and water. All animal studies were conducted in accordance with ethical guidelines and animal welfare standards according to Austrian regulations for animal research, and were approved by the Committee of Animal Care of the Austrian Federal Ministry of Science and Research. Groups of mice were s.c. administered either (1) biogels (2 o/ow/v) in varying volumes (50, 100, 150 µl) or (2) saline only used as controls. Each experimental group included five to ten animals.

Tail-Flick Test:

The radiant heat tail-flick test was used to assess antinociceptive effects of tested drugs after s.c. administration in mice using an UB 37360 Ugo Basile analgesiometer (Ugo Basile s.r.l., Varese, Italy) as described previously (A. Novoa et al., 2012). The reaction time required by the mouse to remove its tail due to the radiant heat was measured and defined as the tail-flick latency. A cut-off time of 10 s was also used in order to minimize tissue damage. The antinociceptive response was expressed as percent of Maximum Possible Effect (% MPE)=[(TL-BL)/(cut-off time-BL)]×100. Data were analyzed with ANOVA using Tukey's multiple comparison test, and graphically processed with the GraphPad Prism Software (GraphPad Software Inc., San Diego, CA).

II) Results: Nociceptive Assessment

Figure 12:
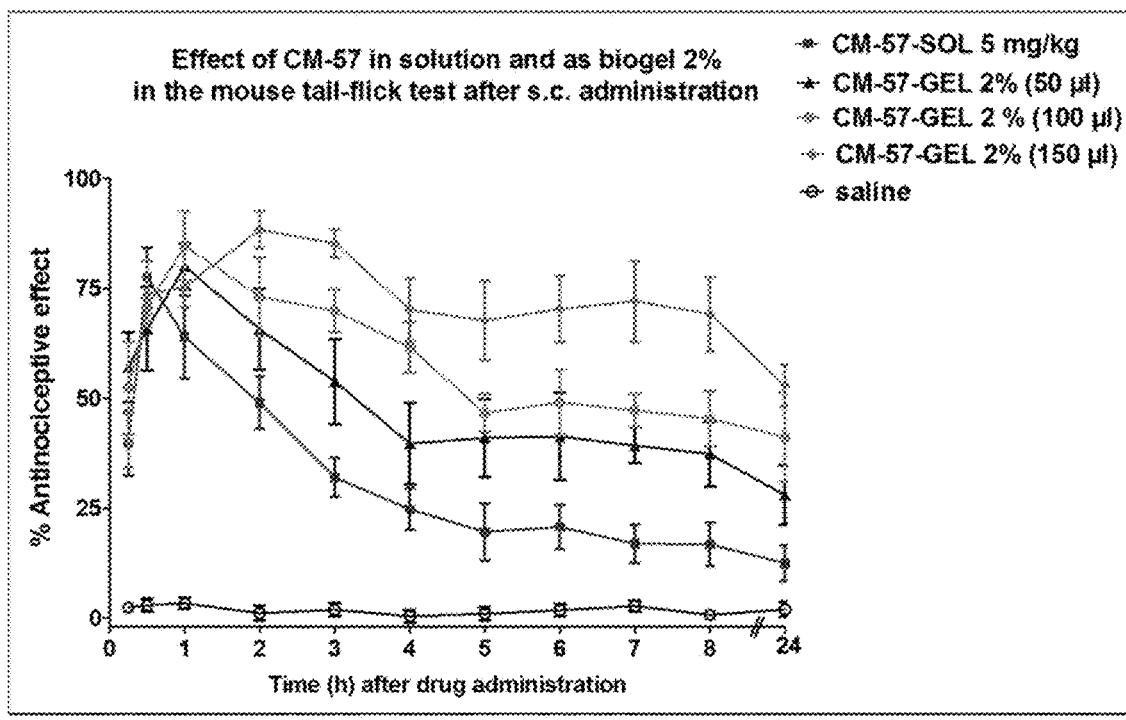
FIG. 12 represents antinociceptive effects of morphine in the mouse tail-flick test after s.c. administration, applied in solution or co-formulated with hydrogel formed by amphipathic hydrogelator peptide 2 (2% w/v). Left panel: Time course of the antinociceptive response as % of Maximum Possible Effect (¾MPE). Doses of morphine are given per mouse. Data are the mean±SEM of 5 to 10 mice per group.
Figure 21:
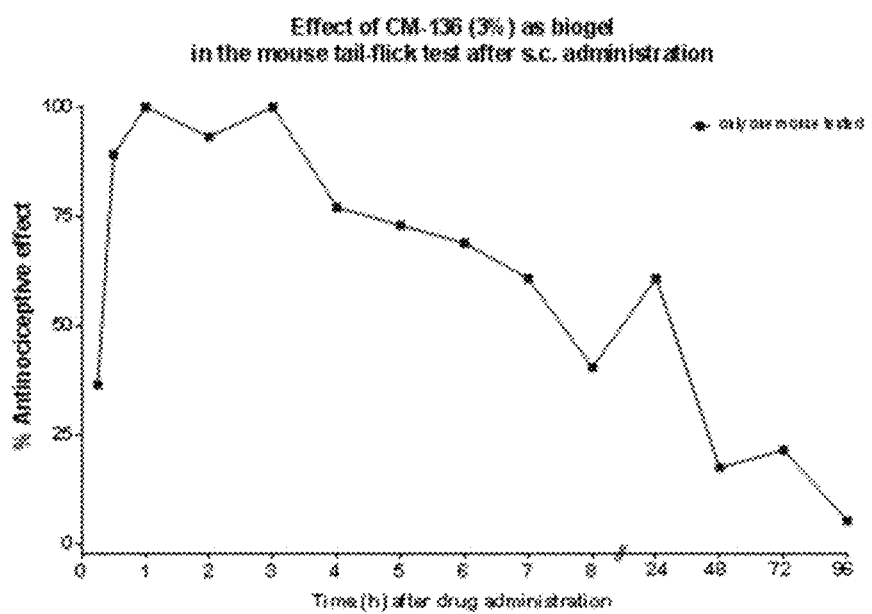
FIG. 21 represents the antinociceptive effects of biogel CM-136 (SEQ ID NO: 48) (3%) as biogel in the mouse tail-flick test after s.c. administration. Time course of the antinociceptive response to CM-136 (3%) as % of Maximum Possible Antinociceptive Effect (¾MPE).

Tests were performed for sequence CM-57 and CM-136 (Table 2), which showed the desired sustained release curve for an injection volume of 150 µl (FIG. 12 and FIG. 21).

The dose of biogel could also be changed by varying the concentration of the 'biogel composition' in the saline solution (e.g. 4% w/v).

Example 8: Stability and Degradability Experiments

The stability (defined as the half-life, $t_{1/2}$) as well as the degradability of the biogels, in solution and in human plasma at 37° C. were investigated.

I) Materials and Methods

Human plasma was obtained from the Belgian Red Cross (Vlaams-Brabant, Leuven). Frozen (−20° C.) human plasma samples were thawed and thermostated to 37+2° C. Dissolution of the lyophilized peptide and consecutive dilutions were performed in milliQ water. The resulting aqueous solutions of biogels CM-53 and CM-57 were spiked in human plasma (10:90 v/v) with final plasma concentrations of 14 µM. During the plasma stability study, samples were taken after 0, 2.5, 5, 7.5, 10, 12.5, 15, 20, 25, 30, 45, 60 min. On every time point 100 µL spiked plasma was transferred to an Eppendorf tube and a protein crash was performed using 300 µL methanol+0.1% TFA (4° C.). Suspensions were vortexed for 15 seconds and placed at 4° C. for 30 to 45 minutes. After centrifugation at 14 000 rpm for 15 minutes, 100 µL supernatant was diluted with 100 µL milliQ water in the injection vial. Injection samples were vortexed for 5 seconds and were analyzed by HPLC. For the calculation of the peptide half-life, only points with an area under the curve (AUC) higher than the AUC of the lowest standard were used. Concentrations were calculated by use of the calibration curve and transferred to a semi-log chart presenting the log concentrations as a function of time. The optimum curve was used to calculate the peptide-half life. Calculations were performed using Microsoft® Office Professional 2010 Excel.

II) Results

For biogels CM-53, CM-57, CM-58, CM-136 and CM-137 the half-life was calculated to be around 18 min, 17 min, 12 min, 11 min and 123 min, respectively.

Figure 13:
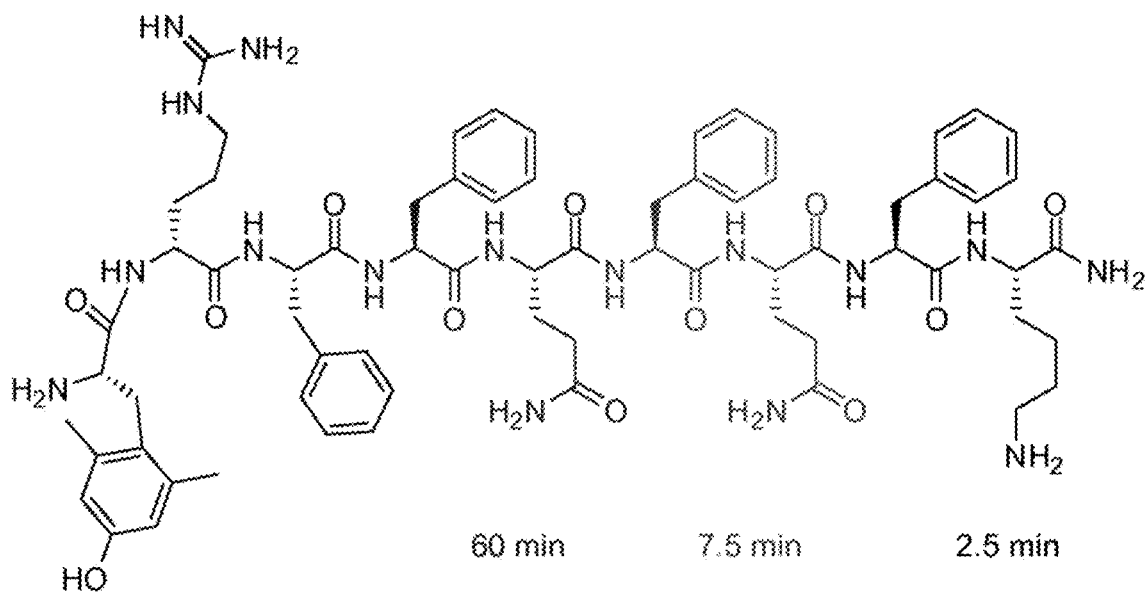
FIG. 13 represents the process of degradation of CM-57. Times indicate the start of degradation at the different cleavage sites.

For biogels CM-53 and CM-57, the degradation followed the same scheme. The degradation started from the C-terminus and proceeded to the N-terminus. The metabolites were analyzed and identified by LC/MS of the corresponding samples resulting from the previous experiments. To illustrate the process of degradation CM-57, CM-58, CM-136 and CM-137 are shown as an example. CM-53 followed exactly the same degradation as CM-57. For CM-57 and CM-53, the degradation occurred from the C-terminus and cleaved 2 amino acid residues at the time. After 2.5 min the appearance of the heptapeptide corresponding to the loss of Phe-Lys-NH$_2$ could be observed, after 7.5 min the degradation of the heptapeptide into the N-terminal pentapeptide started, with loss of the dipeptide Phe-Gln-OH, and finally after 60 min the degradation of the resulting pentapeptide into tripeptide was observed (FIG. 13). The shortest subsequence identified was the tripeptide Dmt-DArg-Phe-OH. Similar as for CM-53 and CM-57, the degradation of CM-58, CM-136 and CM-137 is occurring from the C-terminal end towards the N-terminus (FIG. 23, the arrows illustrate degradation steps). The degradation proceeds by cleavage of 2 amino acids at the time. For CM-137, the degradation stops after the cleavage of the first Gln ($3^{rd}$ amino acid from the Cter) (FIG. 23).

This study gives important information to understand the possible degradation of the biogel sequence before it reached its target.

Furthermore, it appears that the insertion of a $13^3$-homo-residue in the sequence (affording biogel-forming sequence CM-137) increases significantly the stability of the biogel with a resulting half-life of around 123 min.

Example 9: Peptide Hydrogels as a Controlled-Drug Delivery Platform for the Subcutaneous Administration of Opioids I) Materials and Methods Peptide Synthesis:

The syntheses were performed using the standard Fmoc-strategy solid phase peptide synthesis (SPPS). All peptides were purified by preparative reverse phase high-performance liquid chromatography using a linear gradient starting from 10% of acetonitrile (containing 0.1% trifluoroacetic acid) to 80% in 20 min. The pure peptides (>95% purity) were obtained after lyophilization as a white power.

Peptide Gelation:

The peptide gelation occurs by dissolving the TFA salt of the hydrogelator (1 or 2 mg) in 100 µL of aqueous media, PBS solution (pH 7.4) or physiological saline solution (0.9% NaCl). After successive vortexing and sonication, the gel is left to rest overnight at room temperature.

Amphipathic peptide-based hydrogelators (at physiological pH of 7.4) are provided in Table 3:

TABLE 3

| Alias (peptide) | Sequence | SEQ ID NO |
|---|---|---|
| 2 | H-Phe-Glu-Phe-Gln-Phe-Lys-NH2 | SEQ ID NO: 2 |
| 16 | H-Phe-Gln-Phe-Gln-Phe-Lys-NH2 | SEQ ID NO: 16 |
| 12 | H-Trp-Glu-Trp-Gln-Trp-Lys-NH2 | SEQ ID NO: 12 |
| 18 | H-Lys-Phe-Gln-Phe-Glu-Phe-NH2 | SEQ ID NO: 18 |
| 24 | H-DLys-DPhe-DGln-DPhe-DGlu-DPhe-NH2 | SEQ ID NO: 24 |
| 27 | H-Phe-Glu-13;;-homo-Phe-Phe-Gln-Phe-Lys-NH2 | SEQ ID NO: 33 |

TABLE 3-continued

| Alias (peptide) | Sequence | SEQ ID NO |
|---|---|---|
| 28 | H-Phe-Gln-13"-homo-Phe-Phe-Gln-Phe-Lys-NH2 | SEQ ID NO: 34 |
| 29 | H-Lys-Phe-Gln-13"-homo-Phe-Phe-Glu-Phe-NH2 | SEQ ID NO: 35 |
| 30 | H-Dlys-DPhe-DGln-13"-homo-Phe-DPhe-DGlu-DPhe-NH2 | SEQ ID NO: 36 |

Cryo-Transmission Electron Microscopy (TEM):
Performed as described in Example 2.

In Vitro Proteolytic Stability

Human plasma was obtained from the Belgian Red Cross (Vlaams-Brabant, Leuven). Prior to the stability test, selectivity, stability of the compound in the injection solvent, linearity, accuracy and precision of the method were investigated. Frozen (−20° C.) human plasma samples were thawed and thermostated to 37±2° C. Dissolution of the lyophilized peptide and consecutive dilutions were performed in water. The resulting aqueous solutions of each peptide individually was spiked in human plasma (10:90 v/v) with final plasma concentrations of 9 µM. The precipitation solvent (4° C.) and sampling time points for every peptide can be found in Table 4.

TABLE 4

Used precipitation solvent (4° C.) and sampling time points for every peptide

| Peptide | Precipitation solvent | Time points (min) |
|---|---|---|
| 2 | MeOH | 0-5-10-15-30-60 |
| 16 | MeOH | 0-1-2-3-4-5 |
| 12 | MeOH | 0-5-10-15-30-60 |
| 18 | MeOH + 0.1% (v/v) TFA | 0-1-2-3-4-5-10-15 |
| 24 | MeOH + 0.1% (v/v) TFA | 0-5-10-15-30-60-90-120-240-1500 |
| 27 | ACN | 0-5-10-15 |

On every time point 100 µL spiked plasma was transferred to a 500 µL Eppendorf tube and a protein crash was performed using the corresponding precipitation solvent (4° C.). Suspensions were vortexed for 15 s and placed at 4° C. for 30 to 45 min. After centrifugation at 18 625 g for 20 min, 100 µL supernatant was diluted with 100 µL water in the injection vial.

Injection samples were vortexed for 5 s and placed in the autosampler. For the calculation of the peptide half-life, only points with an area under the curve (AUC) higher than the AUC of the lowest standard were used. Concentrations were calculated by use of the calibration curve and transferred to a semi-log chart presenting the log concentrations as a function of time. The optimum curve was used to calculate the peptide half-life. Calculations were performed using Microsoft® Office Professional 2010 Excel.

In Vivo Hydrogel Stability

Synthesis and $^{111}$In-Labeling of the Peptide Hydrogelator

Peptide synthesis—Peptide hydrogelator 2 (SEQ ID NO: 2) and its DOTA-labeled analogue 6 were synthesized by standard Fmoc-strategy solid phase peptide synthesis (SPPS) on Rink Amide resin (ChemImpex, 100-200 mesh, 0.47 mmol g$^{-1}$). Amino acid (3 eq.) activation was carried out with O-(benzotriazol-1-yl)-N,N,N',N'-tetramethyluronium hexafluorophosphate (HBTU, 3 eq.) and N,N-diisopropylethylamine (DIPEA, 4 eq.) in dimethylformamide (DMF). Coupling of amino acids lasted for 40 min at room temperature (rt). Fmoc-deprotection was carried out using 4-methylpiperidine (20 v/v¾ solution in DMF), while washing steps were performed with DMF and dichloromethane (DCM). For the synthesis of N-terminally derived DOTA-peptides, DOTA-tris(tert-butyl)-ester was used (2 eq.), and coupled by an activation with 2 eq. HBTU and 3 eq. DIPEA, and a coupling time of 1 h. Cleavage and side chain deprotection was executed using a trifluoroacetic acid (TFA)/triisopropylsilane (TIS)/water (95:2.5:2.5, v/v/v) mixture at rt for 1.5 h. After vacuum evaporation, crude peptide was precipitated in diethyl ether and lyophilized. After dissolution in acetonitrile/water (ca. 50:50, v/v), purification was carried out by preparative reversed-phase high-performance liquid chromatography (RP-HPIC). Collected fractions were lyophilized to retrieve the purified peptide (>98% purity according to HPIC analysis).

$^{111}$/n-labeling of DOTA-peptide—$^{111}$InCb (5 µl,±4 MBq) (Mallinckrodt) was added to 200 µl 1 mg/ml DOTA-peptide 6, dissolved in 0.2 M ammonium acetate buffer (NH$_4$OAc) pH 5, and incubated for 30 min at 50° C. Radiochemical purity (>95%) was verified by ITIC using 0.1 M citrate buffer pH 5 as mobile phase. 200 µl of $^{111}$In-peptide 6 was diluted up to 1 ml with phosphate buffered saline (PBS, 10 mM) and incorporated within the hydrogel as described below.

Synthesis and $^{111}$In-Labeling of the Different Cargos

Fluorescent cargo—IRDye800CW N-hydroxysuccinimide (NHS) ester (Li-COR Biosciences) was solubilized at 4 mg/l in PBS. The solution was stirred for 2 h in order to hydrolyze the NHS ester, resulting in compound 2 as fluorescent cargo (MW=1068 g/mol). The dye solution was either used as such, or incorporated within the hydrogel as described below.

Small molecule cargo—DOTA-4-amino-2-cyclohexylmethyl-indolo[3,4-c]azepin-2-on 3 was prepared in three standard deprotection-coupling steps from its t-butyloxycarbonyl-precursor (Boe-precursor). Synthetic details can be found in ESI.

Peptide cargo—DOTA-peptide cargo 4 was synthesized analogous to DOTA-peptide 6 (see above).

Nanobody® (Nb) cargo—Twenty-fold molar excess of p-SCN-Bn-CHX-A"-DTPA chelator (Macrocyclics) was incubated with 1 mg/ml of Nb cAbVCAM1-5 dissolved in 0.05 M sodium carbonate buffer pH 8.7 for 2 hours at room temperature, for conjugation to the primary £-amine lysine side chain groups of the Nb. The conjugated Nb 5 was subsequently purified by size-exclusion chromatography on a Superdex 75 10/300 GI column (GE Healthcare) in 0.1 M NH$_4$OAc pH 7 (elution rate 0.5 ml/min).

$^{111}$In-labeling of different cargos—$^{111}$InCb (10-20 µl, ±9 MBq) was added to 1 mg of DOTA-compound 3, 1 mg of DOTA-peptide 4 or 4.5 nmol of DTPA-Nb 5 (supplemented up to 1 mg with unconjugated Nb) dissolved in 200 µl 0.2 M NH$_4$OAc pH 5, and incubated for 30 min at 50° C. Radiochemical purity (>97%) was verified by ITIC using 0.1 M citrate buffer pH 5 as mobile phase.

The $^{111}$In-labeled molecules were diluted up to 1 ml with PBS and either used as such, or incorporated within the hydrogel as described below.

Hydrogel Preparation

For the preparation of $^{111}$In-labeled hydrogel and hydrogels loaded with fluorescent dye or $^{111}$In-labeled cargos, the above described 1 ml PBS-containing solutions were added to 20 mg of TFA salt of peptide hydrogelator 2 (SEQ ID NO:

2). After sequential vortexing and sonication, hydrogels (2 w/v¾) were formed and let to rest overnight.

In Vivo Monitoring of Cargo Release with Fluorescence Imaging

Animal study protocols were approved by the Ethical Committee for Animal Experiments of the Vrije Universiteit Brussel (also for section 2.5.). After subcutaneous injection of 150 μl of hydrogel containing 0.5 nmol of IRDye 800CW in athymic nude mice (Charles River, n=3 per group), fluorescence reflectance images of the posterior side of the mice were acquired over 24 h using the Fluobeam800 (Fluoptics) under 2.5% isoflurane anesthesia (Iso-Vet, Eurovet NV/SA). Fluorescence images were overlaid with white light images for anatomical localization. Regions of interest (ROI) were drawn around the site of injection and total fluorescence signal was measured within these ROIs using ImageJ software.

In Vivo Monitoring of Stability and Cargo Release with SPECT/CT

C57Bl/6J mice were purchased by Charles River (n=3 per group) and all experimental procedures were performed under 2.5% isoflurane anesthesia (Iso-vet). 150 μL (0.518±0.037 MBq) of the $^{111}$In-labeled hydrogel (stability experiment) or 150 μL (1.702±0.777 MBq) of hydrogels loaded with $^{111}$In-labeled cargos (cargo release experiment) were injected subcutaneously on the hind limb. For comparison, 150 μL of $^{111}$In-labeled cargos not loaded into a hydrogel were also subcutaneously injected. Immediately after injection, at 1 h30, 3 h, 6 h, 12 h, 24 h, 48 h and 72 h, animals were subjected to a SPECT/CT scan. SPECT images were acquired on an e.cam$^{180}$ system (Siemens) equipped with two triple-pinhole collimators designed for $^{111}$In (1.5 mm pinhole opening, 250 mm focal length, 47 mm radius of rotation). Images were acquired over 360° in 64 projections of 30 s into a 128×128 matrix and reconstructed using an iterative algorithm correcting for radioactive decay and allowing automatic fusion with CT images (based on six 57Co fiducial markers). Micro-CT imaging was performed using a dual-source CT scanner (Skyscan 1178, Bruker) with 60 kV and 615 mA at a resolution of 83 μm and a scan time of 2 min. Images were reconstructed using a filtered backprojection algorithm.

Maximum intensity projections (MIPs) were generated in Osirix Medical Software. Images were quantified using the software AMIDE (sourceforge.net). For the stability experiments, the size of the gel was determined by automatic delineation, for the cargo release experiments, the total radioactivity within a ROI drawn on the hind limb was calculated. Results were expressed as percentage of injected dose remaining in function of time.

Repeated measures (mixed model) ANOVA was used for the comparison between gel and control groups at different time points (Graphpad Prism 5, significance level was set at 0.05 (*p<0.05, p<0.01, *p<0.001)).

Cytotoxicity
Cell Culture:

Hydrogels were prepared at 1, 2 or 3 mg/100 μL as duplicate in a 96-well ULA plate (Cat #CORN3474; Corning-Costar, 60 μL each well). The gels were photographed and pre-equilibrated before seeding with cells. For equilibration, gels were incubated at room temperature in 40 μL of L929 culture medium with double-strength Anti-Anti (Cat #15240062, GIBCO) for 2 h prior to seeding with cells. The equilibration medium was removed before cell seeding and retained to examine if the gels dissolved (even partially) or disintegrated into the culture medium. Next, 1929 mouse fibroblasts (ATCC) were seeded onto hydrogels at a concentration of 200,000 cells/ml in a volume of 50 μl. The cells were photographed immediately after seeding, observed by microscopy 2 h post-seeding and then observed and photographed at 24 h post-seeding. The cell culture medium consisted of MEM+GlutaMAX I (Cat #41090-036; GIBCO); 10% foetal bovine serum (Cat #12003C; SAFC, Sigma), 2× Anti-Anti (Cat #41090-036 GIBCO) and 1× Non-Essential Amino Acids (Cat #41090-036; GIBCO).

Microscopy:

Bright field microscopy was performed through use of a IX71 inverted microscope with NIS-Elements F3.0 imaging software (Olympus). The TE2000 Eclipse fluorescent microscope with NIS-Elements AR3.2 software (Nikon) was used for fluorescence imaging microscopy. Automated cell counting was performed on the NC-200 NucleoCounter using proprietary lysis and stabilising reagents and cassettes (ChemoMetec).

Live/Dead Viability Staining:

The viability and distribution of cells was assessed using a LIVE/DEAD Viability/Cytotoxicity Kit *for Mammalian cells* (Live-Dead Kit), (Cat #13224; Molecular Probes). Briefly, a working solution of live/dead solution was made as per manufacturer's instructions by adding 1.25 μl of Calcein AM (solution A) to 2.5 ml of pre-warmed PBS. The solution was thoroughly mixed by vortex and 2.5 μl of Ethidium homodimer (solution B), was added before vortexing a second time to mix. Excess medium was removed and the gels rinsed with 20 μl of warm PBS before a 40 μl of Live/Dead kit working solution was added to each well. The plate was incubated in a 37° C. cell culture incubator for 20 min before viewing using a fluorescent microscope. Green fluorescence was emitted from the cytoplasm of viable cells (excitation/emission ~495 nm/~515 nm) while dead cell nuclei fluoresced red (excitation/emission ~495/~635 nm) allowing a distinction to be made between viable and dead cells.

Nociceptive Assessment
Animals and Drug Administration:

Performed as described in Example 5. The hydrogelator and the hydrogelator (also called "peptide #" herein) combined with morphine could be either peptide hydrogelator 2, peptide hydrogelator 16, peptide hydrogelator 12, peptide hydrogelator 18, peptide hydrogelator 24 or peptide hydrogelator 27.

Tail-Flick Test:

Performed as described in Example 5.

II) Results

Based on the promising results obtained with the amphipathic hexapeptide hydrogelator peptide 2 as an adequate drug delivery system for the in vivo controlled delivery of morphine, a new set of peptide-based hydrogels has been synthesized. In order to improve the efficiency of hydrogels containing the parent hydrogelator peptide 2 as an extended release platform, several structural modifications of hydrogelator peptide 2 were considered. The amphipathic character of peptides, responsible of peptide self-assembly into 13-sheet structures, leads to fibril formation and gelation in aqueous media. Additionally, the self-assembly process can be affected by several parameters such as the nature of the side chains (hydrophobic, hydrophilic, charged or uncharged), as well as the chirality of the amino acid components. Hence, starting from the lead sequence (hydrogelator peptide 2), new sequences were designed (Table 3).

The different charges within the peptide hydrogelator have their importance in the self-assembly process depending on the peptide sequence and the main chain charges at the N-anci C-termini of the peptide sequences influence the gelation properties. While the free C-terminal carboxylic acid is not required for the gel formation, the positive charge present at the N-terminus seemed important, as aggregation may occur upon capping with an acetyl moiety. Here, the first type of envisioned modification was intended to verify the role of a negative charge at the level of the amino acid side chains in this type of short hydrogelators. An initial modification consisted of the selective substitution of a negatively charged side chain ($Glu^2$ residue in hydrogelator peptide 2) by a polar neutral amino acid (Gin), affording the peptide hydrogelator peptide 16 bearing only two positive charges. In parallel, a modification on the hydrophobic part was also investigated. The aliphatic (non-aromatic) hydrophobic amino acids influence the hydrogelation process, mostly affording weaker gels, as compared to the parent hydrogelator peptide 2, with a (complete) loss of gelation depending on the hydrophobic character of the residue. Furthermore, the $\pi$-$\pi$ stacking interactions appeared to be important to produce rigid hydrogels. In this context, the replacement of the aromatic hydrophobic phenylalanine residues in hydrogelator peptide 2 with tryptophan residues, to give sequence hydrogelator peptide 16, was carried out. These modifications are important to understand the influence of charged amino acid as well as hydrophobic residues on peptide self-assembly, the gels' rheological characteristics, and eventually on in vivo release experiments.

Aiming for a more sustained release of drugs, improved proteolytic stability of the peptide hydrogelators has been investigated. Indeed, depending on the release mechanism at play, the stability of peptide hydrogelators can become key in the design. The drug might be released from the peptide matrix after enzymatic degradation of the fibres or after peptide erosion from the fibres and solubilisation prior their proteolysis. The proteolytic stability of such peptide substrates can hence improve the release properties of the resulting hydrogels. Natural L-amino acid containing peptides are known to be easily recognized and degraded by proteolytic enzymes. To tackle this susceptibility to proteolysis, different 'tricks' were considered, such as the incorporation of D-amino acids and 13-(homo) amino acids. Within the field of peptide hydrogels, the modification of one chiral centre from L to D changes the orientation of the side chain and this can in turn strongly affect the macroscopic properties of the gel. In literature, it was shown that the gelation properties of heterochiral peptide hydrogelators can be altered, even via the chirality switch of a single residue. Homochirality of peptide hydrogelators appeared to be beneficial in terms of mechanical properties compared to mixtures of both L- and D-peptides. In order to circumvent this issue, retro-inverso peptidomimetics, peptide analogues were developed to increase the proteolytic stability of the peptide, while maintaining side chain topology. As an example, the retro-inverso peptidomimetic of sequence of hydrogelator peptide 2, sequence of hydrogelator peptide 24, combines reversal of the N-----+C side chain sequence of the parent hydrogelator peptide, and the inversion of the chirality of each amino acid (from L to D). The retro-inverso (RI) hydrogelator peptide 24 presents the same three-dimensional side chain topology as its L-counterpart hydrogelator peptide 2. Peptide analogue peptide 18 can be regarded as an intermediate between hydrogelator peptide 2 and hydrogelator peptide 24, since the amino acid sequence is reversed, yet L-chirality is preserved.

Finally, the effect of inserting a 13-(homo) amino acid in the peptide sequences was tested for its effect to increase the proteolytic stability of the peptide gelator. More particularly, the use of a hydrophobic dyad of dipeptidic $13^3$-homo-phenylalanine-a-phenylalanine ($8^3$-homo-Phe-a-Phe) was tested in hydrogelator peptide 2, now called hydrogelator peptide 27, was designed. The introduction of such a hydrophobic dyad can help to keep the right alternation between hydrophobic and hydrophilic residues, leading to an amphipathic heptapeptide able to promote 13-sheet formation. Mixed a/13-peptide hydrogelators were shown to be less prone to enzymatic degradation in solution as well as in a gel state, in presence of elastase.

Hydrogel Formation and Rheology

The hydrogelation was realized under physiologically relevant conditions, namely via the addition of phosphate-buffered saline (PBS) or sterile physiological saline solution (0.9% NaCl). The needed amount of hydrogelator was weighed in an Eppendorf® and solubilized by the addition of the above solutions. After vortex and sonication steps, the resulting solution was left at room temperature until gelation occurred. The gelation was qualitatively verified by the inverted vial test (if no gravitational flow was visible the gelation was considered successful). It can be noticed that all peptide hydrogelators depicted formed gels in PBS and saline solution at a concentration of 1 to 2% w/v. Of note, the modification giving way to hydrogelator peptide 16 seems to be highly beneficial in terms of mechanical properties, allowing gel formation with a lower minimum gelation concentration (MGC) of 1% w/v (weight/volume) compared to the parent sequence of hydrogelator peptide 2.

Transmission Electron Microscopy

CryoTEM and negative staining of the peptide hydrogels showed fibrous morphologies at the nanoscale. For all hydrogels composed of hydrogelator peptides 2, 16, 12, 18, 24 and 27, long fibres were observed of ~5 nm in diameter that intertwined and underpinned the supramolecular structure of the gels. Intertwining of fibres into twisted ropes was also observed in some cases along with alignment of fibres into higher order bundles in a manner similar to that observed previously. Interestingly, a change in one residue of the peptide sequence resulted in a subtle change in fibre morphology illustrating the flexibility of design of these systems.

Figure 14:
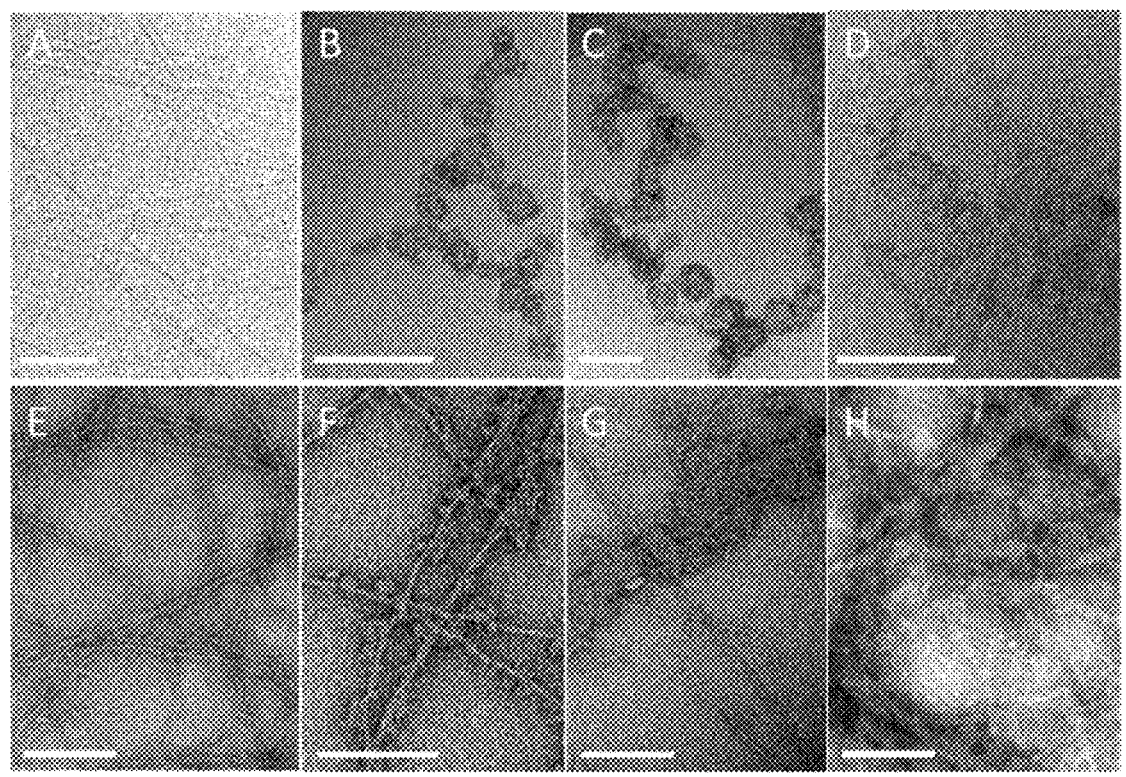
FIG. 14 represents Cryo-TEM (A) and negative stain (E) images of the hydrogel composed of amphipathic hydrogelator peptide 2 showing a self-assembled nanofibrous network. Images B-D (cryoTEM) and F-H (negative stain) are of amphipathic hydrogelator peptide 2 loaded with 10 mg of ethyl morphine and clearly show association of the drug along the fibres within the supramolecular structure).

To examine the effect of drug encapsulation on the morphology of the self-assembled peptide hydrogelators, cryo-TEM experiments on drug-loaded systems were performed. A hydrogel of hydrogelator peptide 2 proved able to encapsulate high quantities (up to 10 mg) of ethylmorphine, an opioid analgesic and antitussive compound. The images depicted in FIG. 14 show the association of "microcrystals" of the drug along the axes of the fibres, with the clusters only co-located with the peptide fibres. Where the fibres intersect and cross over, larger clusters can also be observed. While the fibre diameter remains the same as in unloaded hydrogels (~5 nm), the coated fibres range from ~15-70 nm across with an average of ~45 nm. As cryoTEM precludes microcystallization being an artefact of preparation, these images indicate how the drug potentially associates with the fibres, rather than just being encapsulated in solution in a hydrogel network. If ethylmorphine was to crystallize on its own, the fibres would not be visible due to a large mass of solid drug crystals of uncontrolled dimensions. The observed "microcrystallization" suggests that the fibres act as seeding sites and hence the association of drug along the fibres is visible. It can be noticed that the degree of coating of the fibres is variable and that not all fibres appear to associate with the drug. This may be due to accessibility and variation along the fibres and the ability of solvent and associated drug to penetrate the dense fibrous network. Under negative staining, beautiful pictures were obtained, bearing out the association of the drug with the fibres in a spectacular way. Pleasingly, these images confirm those observed by cryoTEM with the fibres diameters ~5 nm and the size of coated fibres ranging from ~15-70 nm across, with an average of ~45 nm.

Proteolytic Stability Studies

Figure 15:
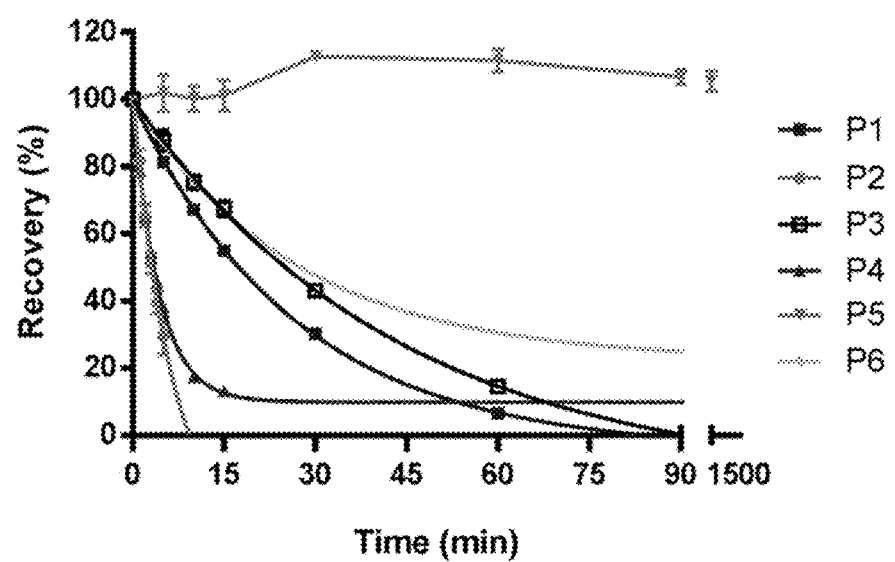
FIG. 15 represents the stability profiles of amphipathic peptide hydrogelators (in solution) in human plasma over time (n=3). P1 represents amphipathic hydrogelator peptide 2 (SEQ ID NO: 2), P2 represents amphipathic hydrogelator peptide 16 (SEQ ID NO: 16), P3 represents amphipathic hydrogelator peptide 12 (SEQ ID NO:12), P4 represents amphipathic hydrogelator peptide 18 (SEQ ID NO: 18), P5 represents amphipathic hydrogelator peptide 24 (SEQ ID NO: 24) and P6 represents amphipathic hydrogelator peptide 27 (SEQ ID NO: 33).

The in vitro biostability experiments of all peptide gelators, were performed in human plasma at 37° C. in solution, meaning that concentrations significantly lower than the minimum concentration of gelation (MCG) were used. The sensitivity to proteolytic degradation was monitored by measuring the percentage of intact peptide via HPLC-UV after their incubation in human plasma at 37° C. (FIG. 15). From these profiles, the half-life of each sequence was calculated. Among all homochiral peptides bearing L-amino acids (hydrogelator peptide 2, 16, 12 and 18), the degradation profiles are quite different, with calculated half-lifes ranging from 3 to 21 min. While the parent hydrogelator peptide 2 has a half-life around 15 min, replacement of one glutamic acid by one glutamine affords hydrogelator peptide 16, which is characterized by a reduced stability with a half-life around 3 min. The same result is observed for peptide hydrogelator 18 (half-life of approximately 5 min). However, the phenylalanine to tryptophan switch within hydrogelator peptide 2, giving way to sequence of peptide hydrogelator 12, leads to a similar degradation profile with a longer half-life (ca. 21 min). As expected, peptide hydrogelator peptide 24, containing D-amino acids only, shows an increased stability with no apparent proteolytic degradation. The peptide remains intact after 25 h of incubation. As a consequence, no half-life could be determined (after 25 h) for this sequence. However, the insertion of one 13-(homo)-residue, affording to the mixed a/13-sequence of hydrogelator peptide 27, induces a limited increase of the stability with a resulting half-life of around 25 min. Because hydrogelator peptide 2, peptide 12 and peptide 27 are more resistant to proteolytic degradation, as compared to hydrogelator peptide 16 and hydrogelator peptide 18, the Applicants hypothesized that their corresponding hydrogels could afford an extended-drug release.

In Vivo Biostability Studies

Figure 16:
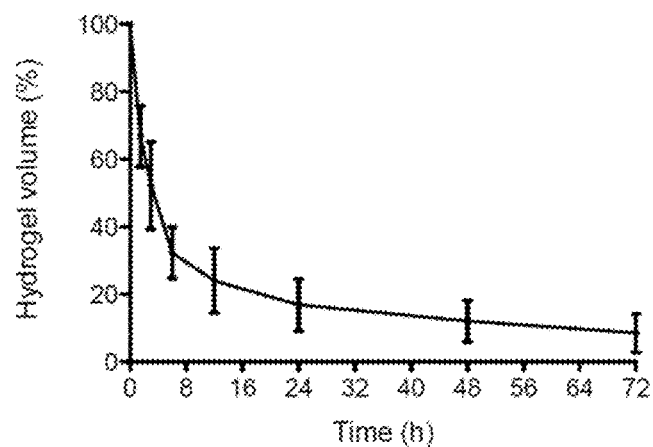
FIG. 16 represents the in vivo stability of the hydrogel formed by amphipathic hydrogelator peptide 2 (2 w/v¾ in PBS), representing hydrogel volume in function of time.

The in vivo biostability of a hydrogel of hydrogelator peptide 2 was visualized using radioactively labelled hydrogelator peptide 2 and nuclear imaging modalities. FIG. 16 shows that most degradation occurred within 12 hours after subcutaneous injection of the hydrogel.

Fluorescence Imaging

Figure 24:
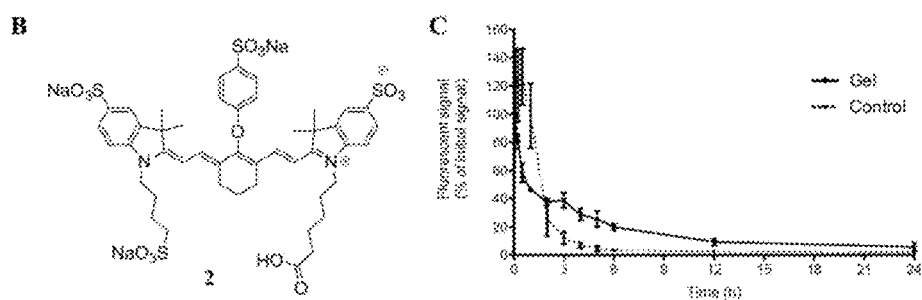
FIG. 24 represents the in vivo fluorescent images (after s.c. injection of fluorescent IRDye800CW carboxylate 2 (B), co-formulated with the peptide hydrogelator 2 (2 w/v¾ in PBS) (SEQ ID NO: 2) and in solution. Images are shown for an exposure time of 25 ms. A quantitative analysis of the images, showing the fluorescent signal in function of time, is shown in C.

In a first experiment, the in vivo release of the fluorescent dye IRDye 800CW carboxylate 39 from the hydrogel formed by hydrogelator peptide 2 was monitored and compared to the release of the same amount of dye injected subcutaneously in solution (150 μL per injection). The decrease in fluorescent signal was measured in function of time, which can be correlated to the release of the fluorescent cargo from the injection site (FIG. 24).

After injection of the dye as solution, the fluorescent signal reduces drastically within approximately two hours, indicating the quick elimination of the dye from the injection site. In contrast, co-formulation of the dye within the peptide hydrogel results in a fluorescent signal that remains visible for more than 24 h indicating that the peptide gel is able to release the dye in a delayed way over a time period of up to 24 h.

Although in vivo fluorescence imaging is a broadly applicable, fast and sensitive method that is widely used within this field, quantitative analysis of planar optical images remains inadequate due to lack of depth resolution and tissue attenuation. This can lead to aberrant data, such as for the control data shown in FIG. 24C. The measured fluorescent signal of the control first increases above 100% before it drops below the data of the dye-gel co-formulation. This can be attributed to diffusion of dye towards the skin surface, resulting in a higher signal. To address the issue of quantitative analysis, a nuclear imaging technique, namely SPECT, was selected as alternative for further experiments, although data acquisition is more time consuming and radiolabeling is more cumbersome.

Nuclear Imaging

Cargo Scope

Figure 25:
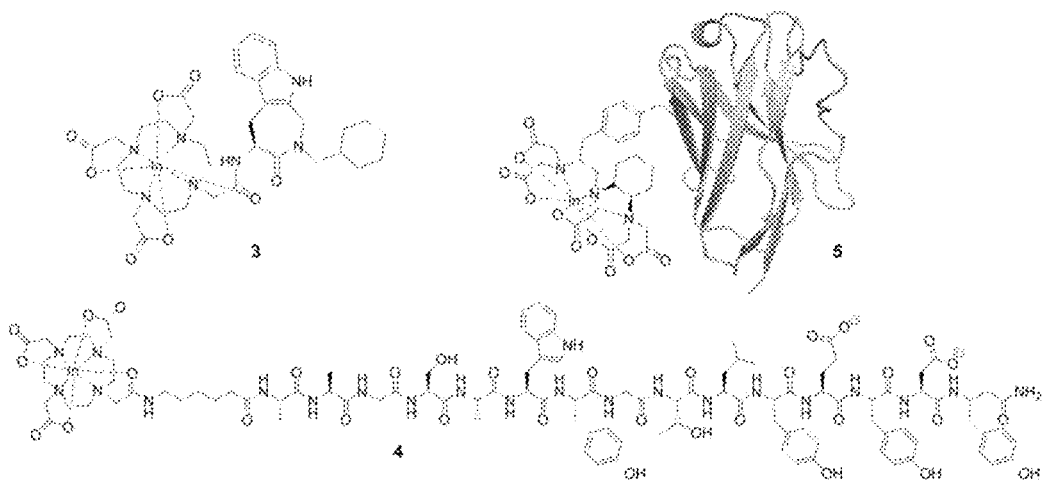

Thanks to among others their good oral availability, stability and lower cost of development, small molecules dominate the drug market to date. However, this drug class may suffer from a low target selectivity due to the small molecular size, resulting in an increased risk for side effects or toxicity. A significantly better selectivity can be obtained with protein therapeutics, possessing more interaction points with the desired target. Nonetheless, proteins have a low bioavailability and stability and come with a higher production cost. Peptide therapeutics represent an upcoming drug class, which combines the advantages of the two previously described classes, i.e. obtaining high target specificity while maintaining a good oral availability and stability at a lowered cost. The release of representative dummy examples of these three major therapeutically relevant classes from hydrogels was investigated by SPECT/CT imaging. Hereto, a small molecule 3 (4-amino-2-cyclohexylmethyl-indolo[3,4-c]azepin-2-on; MW 311 Da), a 15-residue peptide 4 (MW 1738 Da) and a small protein 5 (cAbVCAM1-5 nanobody, MW ca. 15 kDa) were chosen. All were covalently linked to a chelator (DOTA or DTPA) permitting labeling with the radioactive isotope $^{111}$In enabling monitoring by SPECT (FIG. 25).

These radiolabeled cargos were co-formulated within the hydrogel formed by hydrogelator peptide 2 (SEQ ID NO:2) at a concentration of 1 mg/ml, which can be considered as a therapeutic relevant dose. The cargo-loaded gels were s.c. injected on the hind limb (150 μL) and the release was followed by SPECT/CT imaging. As a control, the cargos were also s.c. injected in solution without the peptide hydrogelator in the same concentration. When injected in solution, the cargos are quickly eliminated from the injection site. The small molecule and peptide cargos are totally cleared within three hours, while the Nb is cleared within six hours (FIG. 26). When co-formulated within the hydrogel formed by hydrogelator peptide 2 (SEQ ID NO:2), the release is clearly prolonged. The cargos are now released within a time span of 12 h (FIG. 26). The 15-residue peptide 4 and Nb 5 show a similar release profile, demonstrating clearly a sustained release, whereas the small molecule is released in a rather fast manner (faster decrease of radioactive signal within the same amount of time). This is probably due to its small size, which allows a rapid diffusion throughout the hydrogel network, or an incapability of interacting with the peptide fibers potentially due to the very hydrophilic nature of the radiolabeled small molecule cargo, thus causing a less delayed release from the gel's network.

In Vivo Hydrogel Stability

Figure 27:
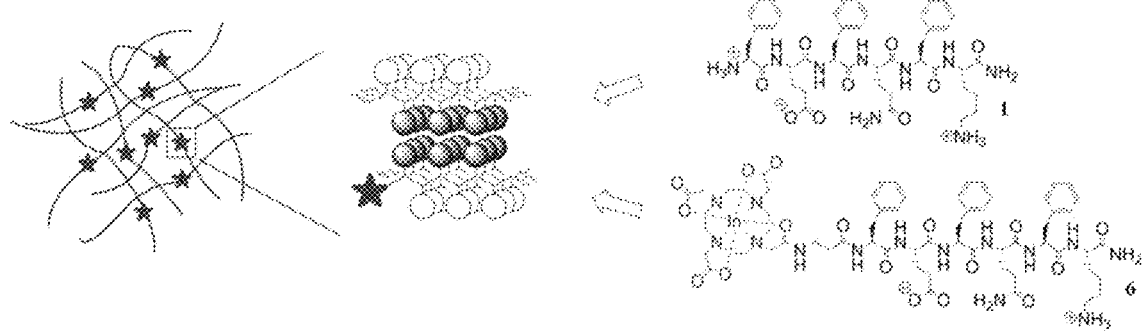
FIG. 27 represents a schematic representation of the labeled hydrogel network. Multiple labels are present in all fibers, but all fibers contain both hydrogelator peptide 2 (SEQ ID NO: 2) and DOTA-peptide 6.

A hydrogel can liberate the encapsulated cargo to its surroundings by various release mechanisms, of which diffusion and erosion are the most well-known. In order to elucidate the release mechanism of the Applicant's system, the in vivo stability of the hydrogel formed by hydrogelator peptide 2 (SEQ ID NO:2) was investigated. To this end, the hydrogel network was radioactively labeled by the incorporation of labeled peptide hydrogelator molecules (1 wt % labeled DOTA-peptide 6 relative to unlabeled hydrogelator peptide 2 (SEQ ID NO: 2) was used) in the hydrogel network (FIG. 27). In this way, the hydrogel can be localized after s.c. injection and gel degradation or erosion—manifested as a volume reduction—can be tracked by measuring the remaining radioactive signal at the injection site in function of time.

For the here reported system, the destiny of the peptide hydrogel after s.c. injection was examined quantitatively via nuclear imaging in a non-invasive way (FIG. 16). The largest volume reduction occurs within the first 12 h (with 24% remaining), after which hydrogel erosion takes place more gradually up to 72 h post-injection (9% remaining). It is however expected that the volume reduction will vary depending on the type of peptide gelator, the injection site and the animal model. Nonetheless, within this study, an interesting correlation between in vivo stability and cargo release can be found. Cargos were released within 12 h, which was also the time span in which the largest hydrogel volume reduction occurred. Therefore, it can be assumed that hydrogel degradation/erosion essentially causes cargo release, whereas diffusion only plays a limited role, especially for larger molecules (cfr. more sustained release for peptide and Nb cargos compared to small molecule cargo). The Applicants expect that larger molecules experience a more hindered diffusion out of the pores of the hydrogel network, so that the most important release mechanism is their liberation from these pores by network degradation. Furthermore, hydrophobic and π-π stacking interactions between the cargo and the peptide fibers are expected to be important for encapsulation of small molecule drugs, also accompanied by release via hydrogel erosion.

The degraded hydrogels, as well as the released cargos, were eliminated from the body by renal clearance and no accumulation in specific organs took place (images in FIGS. 26 and 16). This is of high importance, since it points to a low expected toxicity for an eventual clinical application.

In view of the above, the Applicant's hydrogel system can be broadly applicable in the fields of chronic pain, cancer, obesity, neurodegenerative diseases such as Alzheimer and Parkinson, delivery of antibiotics, hormone therapy, etc.

Cytotoxicity

Figure 17:
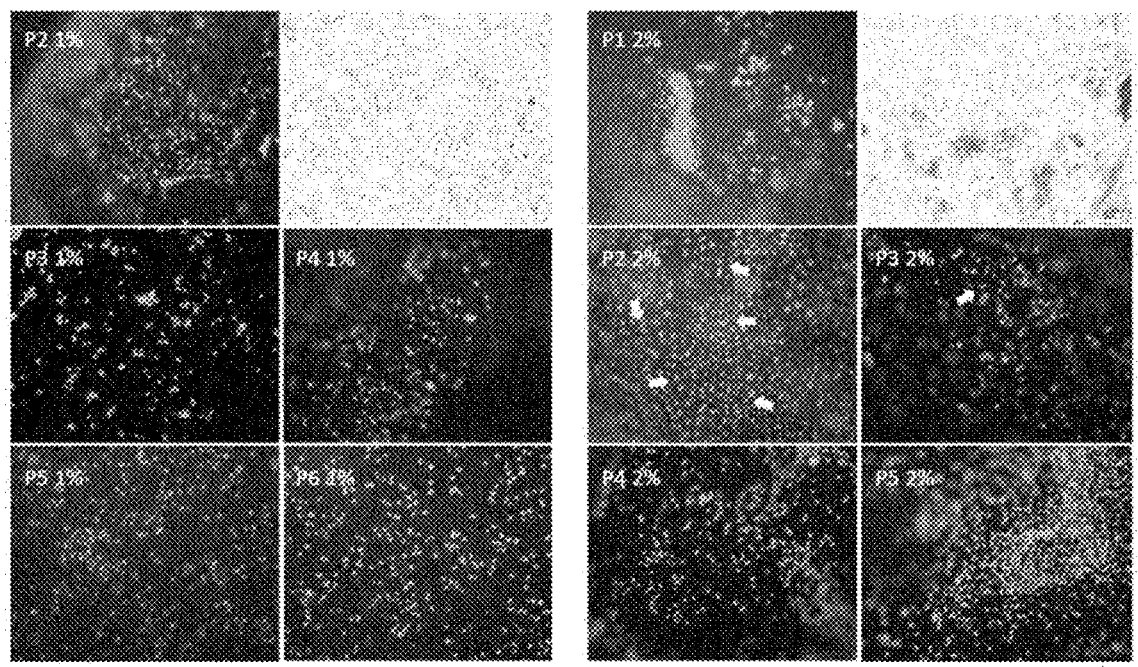
FIG. 17 represents confocal microscopy of L929 fibroblast cells with amphipathic peptide hydrogelators 2, 12, 16, 18, 24 and 27 at 1% w/v (left set of images) and at 2% w/v (right set of images) after 24 h. Brightfield images of amphipathic hydrogelator peptide 16 at 1% and 2% w/v show clear examples of cell attachment and spreading (arrows). Green Fluorescence indicates live cells. Magnification=10×.

As the described hydrogelators are intended for biomedical applications, in vitro cell culture experiments were performed prior to in vivo experiments. No cytotoxicity (cell viability 100%) was observed for the majority of the peptide hydrogels tested at 1% w/v with cell viability being greater than 95% and in all cases 24 h after seeding. (See FIG. 17). Of note is the subtle differences in morphology of the cells incubated with the various peptide hydrogels. While all cells were viable 24 h after seeding, their morphologies ranged from slightly rounded for hydrogelator peptide 2, 18, 24 and 27 to clear instances of attachment and spreading for hydrogelator peptide 16 and 12 (E and F in FIG. 17).

Antinociceptive Effects

Because hydrogels formed from hydrogelator peptide 2, 16, 12, 18 and 27 demonstrate thixotropic behavior, and showed no cytotoxicity in vitro, they have been considered for further in vivo studies. In order to investigate the influence of the stabilized peptide hydrogelators on the extent of drug release, all of the described hydrogelators were tested as a controlled drug delivery platform in a thermal nociception assay, the tail-flick test, in mice after s.c. administration. In these investigations, peptide hydrogelators and two different encapsulated opioid analgesics were co-formulated. Since morphine is widely used in the clinic for the treatment of severe and chronic pain, and in light of its short duration of action, it represents a suitable analgesic drug to assess kinetics of its release, as well as the in vivo efficacy of the designed controlled drug delivery platform. A second cargo, 14-MM, a μ-opioid agonist structurally-related to morphine, was included in the current study. The selection of 14-MM was based on its well-established in vitro and in vivo pharmacological profile. It was designated as a promising centrally acting μ-opioid analgesic that has, besides the very high antinociceptive potency, when administered systemically to rodents, the advantage of causing considerably less pronounced adverse effects. Moreover, 14-MM is only short acting in inducing an antinociceptive response in animals.

Figure 18:
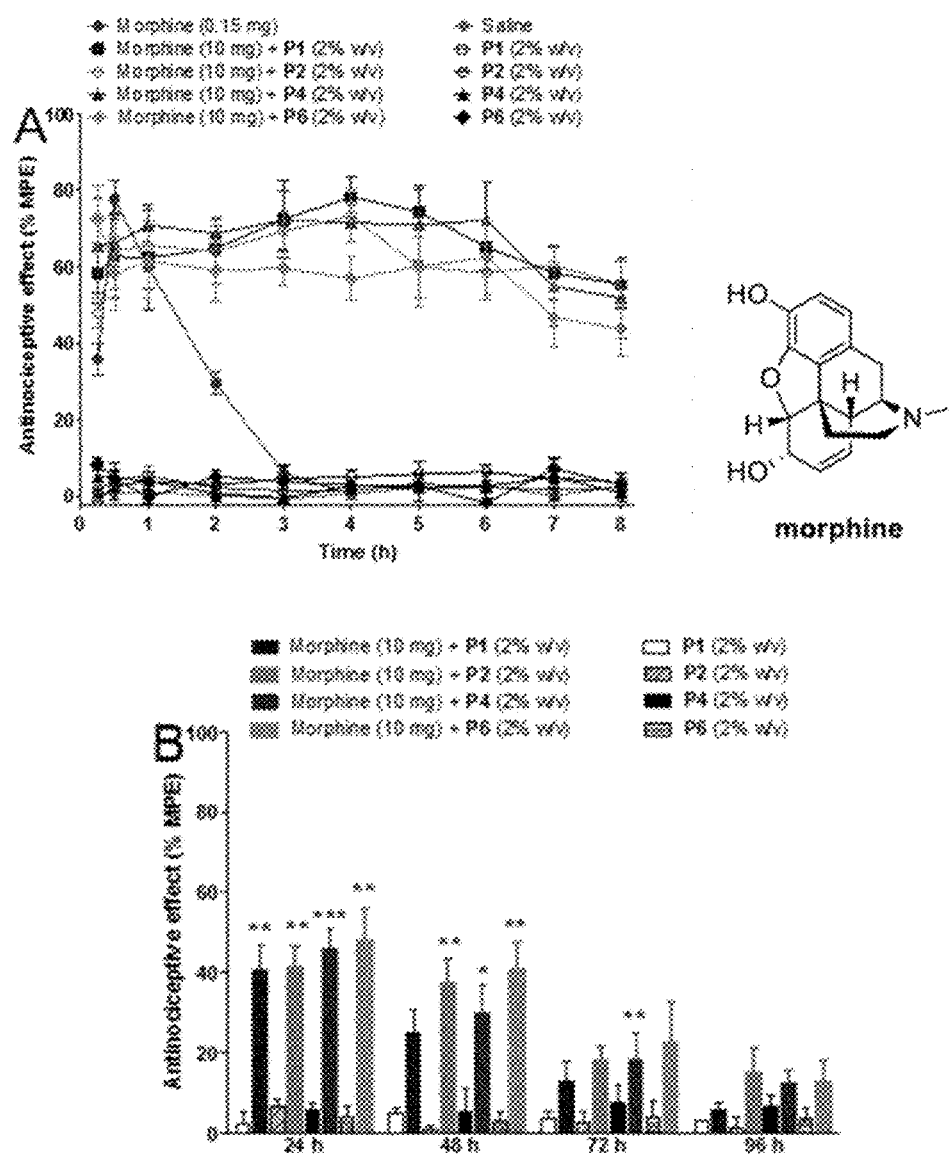
FIG. 18 represents the comparison of antinociceptive effects of morphine in the mouse tail-flick test after s.c. administration, applied in solution or co-formulated with the new hydrogelator peptide 16, peptide 12 and peptide 27 (2% w/v) and previously described peptide 2 (2% w/v). Time course of the antinociceptive response as % maximum possible effect (¾MPE) from 15 min to 8 h (A) and from 24 h to 96 h (B). Doses of morphine are given per mouse. Data are the mean±SEM of 5 to 7 mice per group. *$p<0.05$, $p<0.01$ and *$p<0.001$ 01 vs. respective control group treated only with hydrogel (2% w/v) (ANOVA with Tukey's post-hoc test). P1 represents peptide 2 (SEQ ID NO:2), P2 represents peptide 16 (SEQ ID NO:16), P4 represents peptide 18 (SEQ ID NO:18) and P6 represents peptide 27 (SEQ ID NO:33).
Figure 19:
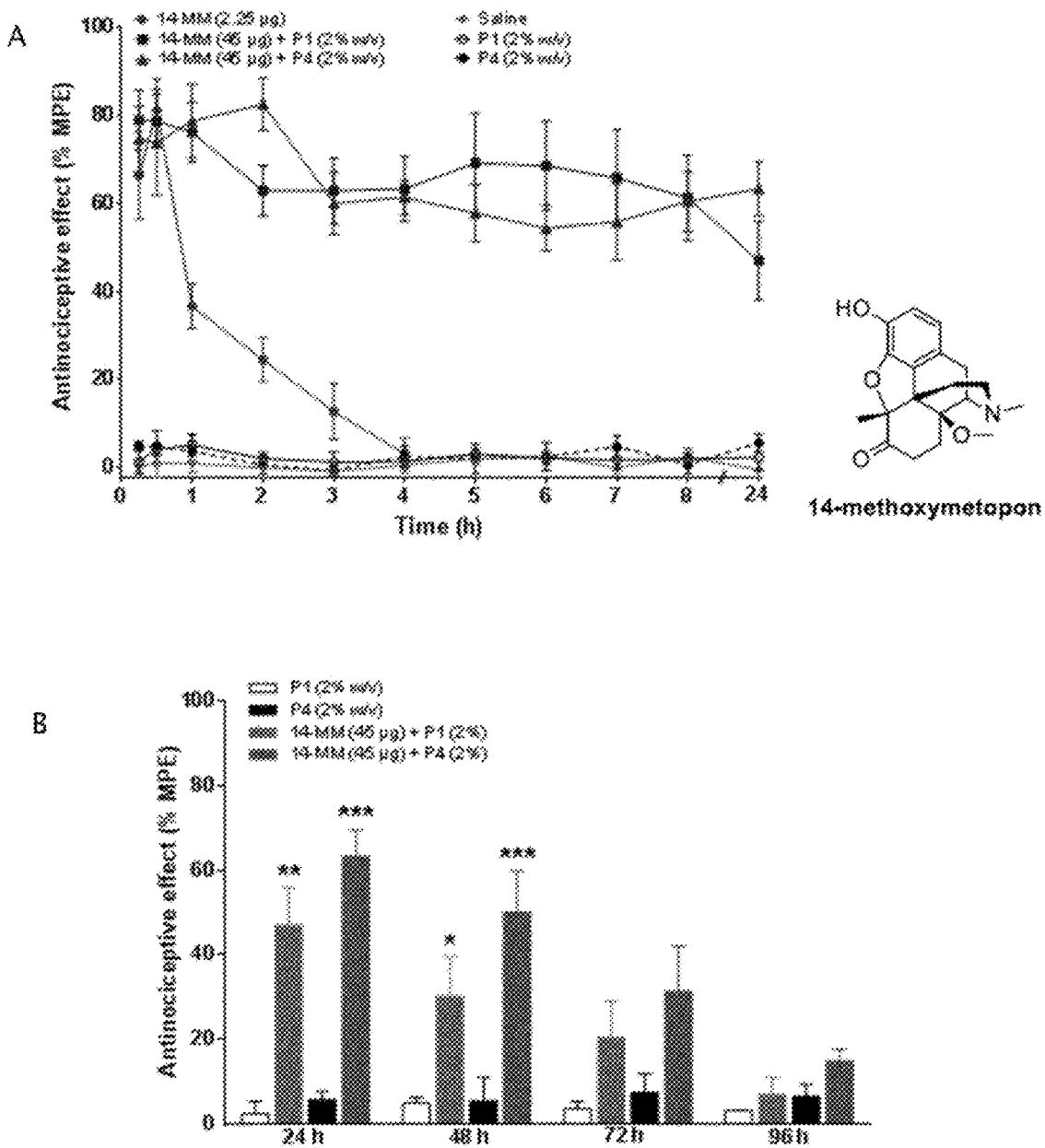
FIG. 19 represents the comparison of antinociceptive effects of 14-MM in the mouse tail-flick test after s.c. administration, applied in solution or co-formulated with hydrogels peptide 2 and peptide 18 (2% w/v). Time course of the antinociceptive response as % maximum possible effect (¾MPE) from 15 min to 8 h (A) and from 24 h to 96 h (B). Doses of 14-MM are given per mouse. Data are the mean±SEM of 5 to 7 mice per group. *$p<0.05$, $p<0.01$ and *$p<0.001$ 01 vs. respective control group treated only with hydrogel (2% w/v) (ANOVA with Tukey's post-hoc test). P1 represents peptide 2 (SEQ ID NO:2) and P4 represents peptide 18 (SEQ ID NO:18).

To examine the influence of the designed peptide-based controlled drug delivery systems on the duration of antinociceptive action and to define the optimal dose of the opioid drug required to reach a therapeutic effect corresponding to 80% of the Maximum Possible effect (80% MPE), the targeted opioid analgesics, morphine and 14-MM, were first s.c. administered as bolus (FIG. 18 and FIG. 19, respectively). In both cases, following s.c. administration of the optimal doses a marked, but very short antinociceptive response was observed with a peak effect at 30 min, followed by a rapid decline, with no effect after 3 or 4 h. Due to the high potency of 14-MM, the dose required to produce a 80% MPE is 66 times lower than the one of morphine. As a consequence, the drug loadings within the hydrogel differ significantly depending on the administered drug. In case of morphine, drug loading was also limited by the solubility of the drug, maximum 10 mg being soluble in 150 DL of saline solution.

In order to evaluate the influence of the different hydrogelator compositions on the extended release profile, several formulations were subcutaneously injected in mice and the tail-flick test was performed. In this test, time points for all observations were spanned for a total of 96 h (FIGS. 18 and 19). Each formulation contained the same concentration of peptide hydrogel (2% w/v), the same amount of loaded drug (10 mg for morphine and 45 μg for 14-MM), dissolved within an identical volume (150 μL). The formulation containing 10 mg of morphine and 2% w/v of hydrogel peptide 2 (FIG. 18) s.c. administered to mice, elicited a significant and prolonged antinociceptive effect at 24 h compared to controls receiving hydrogelator peptide 2 alone and physiological saline solution alone (FIG. 18B). Although not statistically significant, around 25% of the MPE was still detectable at 48 h, and no considerable effects compared to control were noticed at 72 and 96 h after administration of morphine in the co-formulation with hydrogelator peptide 2 (2% w/v). In the next set of experiments, morphine was co-formulated with the other hydrogel sequences, presenting comparable extended release profiles (FIG. 18). Significant and extended antinociceptive effects were detected at 24 and 48 h for all three formulations of morphine with hydrogelators peptide 16, peptide 18 and peptide 27, when s.c. injected to mice (FIG. 18B). Furthermore, s.c. administration of the co-formulation of morphine with hydrogelator peptide 18 produced a prolonged and significant effect at 72 h. Notably, during the first hour there was no significant difference ($p>0.05$) in the antinociceptive effect induced by the co-formulations of morphine with either peptide hydrogelators (peptide 2, peptide 16, peptide 18, and peptide 27) in comparison to morphine (0.15 mg) given s.c. as bolus (FIG. 18A). At later time points up to 24 h, all four formulations of morphine produced significant long-lasting effects (***p<0.001) when compared to control mice receiving the respective hydrogel alone. Finally, no significant difference (p>0.05) could be found amongst the investigated co-formulations. Thus, the designed controlled-drug delivery systems in this study appear to be highly effective.

To validate the proposed peptide hydrogelators and to demonstrate a more generic controlled-drug delivery potential of these systems, another set of experiments was performed using a second opioid analgesic as cargo, 14-methoxymethopon (14-MM). While s.c. administration of 14-MM as bolus, at a dose of 2.25 µg, reaches the peak of action after 30 min (with 80% of MPE), a rapid decline in the antinociceptive effect was noticed after 1 h, and no effect remaining remained at 4 h post-injection (FIG. 19A). When 14-MM was co-formulated with either peptide hydrogelator peptide 2 or peptide 18 using a dose of 45 µg, a noticeable extended release profile could be observed over 96 h. Indeed, a significant effect (***p<0.001) up to 4 h is observed for formulations containing hydrogelator peptide 2 and peptide 18 in comparison to administration of 14-MM (2.25 µg) as bolus. When compared to controls treated only with hydrogelator peptide 2 or peptide 18, prolonged effects with significant differences were detected up to 48 h after s.c. administration (FIG. 19B). Though, there was no statistically significance, around 20% and 30% of the MPE was still detectable at 72 h for 14-MM co-formulated with hydrogelator peptide 2 or peptide 18, respectively, and no considerable antinociceptive effects compared to controls were found at 96 h. In contrast to the co-formulations of morphine (FIG. 18), increased ¾MPE values were observed when using 14-MM as a cargo (FIG. 19).

Figure 20:
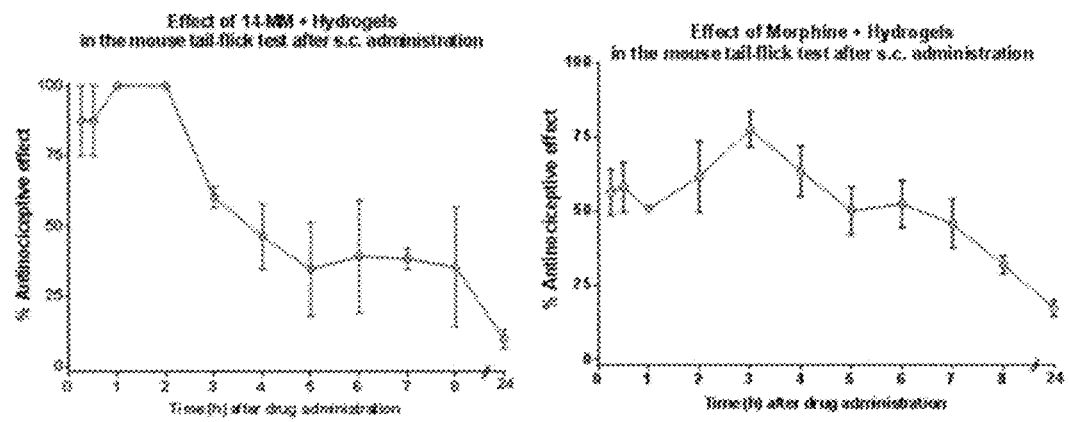
FIG. 20 represents the antinociceptive effects of morphine and 14-MM in the mouse tail-flick test after s.c. administration, co-formulated with hydrogelator peptide 33 (SEQ ID NO: 39) (1-2% w/v), in function of time. Left panel: Time course of the antinociceptive response to 14-MM co-formulated with hydrogelator peptide 33 as % of Maximum Possible Antinociceptive Effect (¾MPE). Right panel: Time course of the antinociceptive response to Morphine co-formulated with hydrogelator peptide 33 as % of Maximum Possible Antinociceptive Effect (¾MPE).

For hydrogelator peptide 33 (2% w/v) (Table 1), groups of mice were s.c. administered either (1) morphine (10 mg per mouse, in a volume of 150 µl) formulated with hydrogelator peptide 33 (1-2% w/v) in physiological saline or 2) 14-MM (45 µg per mouse, in a volume of 150 µl) formulated with hydrogelator peptide 33 (2% w/v) in physiological saline (FIG. 20).

The co-formulation of morphine (10 mg) or 14-MM (45 µg) with hydrogelator peptide 33 (SEQ ID NO: 39) (2% w/v) had also been tested in the tail-flick test assay. Both formulations afford to an extended antinociceptive effect up to 24 h with ca. 10 and 20% MPE, respectively. In case of the co-formulation with 14-MM, a saturation (100% MPE) was observed between 1 and 2 h post administration, probably related to a quick but possibly limited release of the analgesic. Since 14-MM is a much stronger analgesic than morphine even a limited burst release will give high activities. This burst release was not observed for morphine where the antinociceptive effect peak (ca 75%) was delayed of 1 h. Of note, the presence of three halogenated phenylalanine residues within the hydrogelator peptide sequence leads to stronger gels compared to the non-halogenated peptide.

Present inventors have also shown that the insertion of one or more halogenated phenylalanines results in more rigid gels, as compared to the non-halogenated sequences.

Example 10: Peptide Hydrogels as Controlled-Drug Delivery Platform for the Subcutaneous Administration of Opioid Peptides The antinociceptive effect of co-formulations of a peptide hydrogelator as described herein with peptide-based analgesics was investigated in a model of thermal nociception using the tail-flick test in mice. A peptide-based analgesic (CM-80-OP, EO-CM-OP or KGOP01) was injected s.c. in solution (5 mg/kg for CM-80-OP and EO-CM-OP; 1.5 mg/kg for KGOP01), or co-formulated with CM-63 (2% w/v) or hydrogelator peptide 2 (2% w/v) (Table 1, represented in FIG. 22 as MBG-6), following the same protocol as described in Example 5. Peptide-based analgesics used in this study are shown in Table 5. The Tail-flick test was performed as described in Example 5.

FIG. 22 shows that the co-formulations of a peptide hydrogelator with a peptide-based analgesic, more particularly an opioid peptide, had prolonged antinociceptive effects compared to the peptide-based analgesics in solution.

TABLE 5

Sequences of peptide-based analgesics / analgesic pharmacophores

| Alias | Sequence | SEQ ID NO |
|---|---|---|
| EO-CM-OP | Dmt-DLys-Phe-Phe-NH$_2$ | SEQ ID NO: 57 |
| CM-80-OP | Dmt-DArg-Phe-Phe-NH$_2$ | SEQ ID NO: 58 |
| KGOP01 | Dmt-DArg-Aba-βAla-NH$_2$ | SEQ ID NO: 59 |

Figure 28:
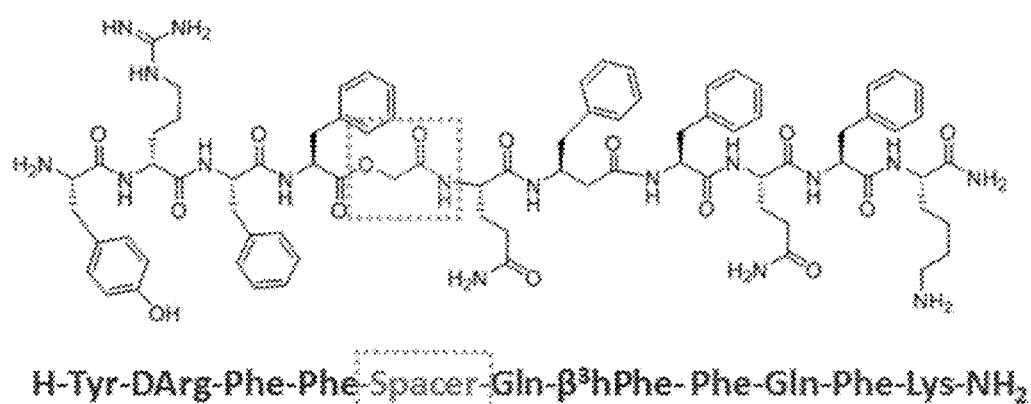
FIG. 28 represents the modification of biogel MOJ-02 (SEQ ID NO: 56) by including an ester as linker (spacer) between the hydrogelator part and the biological active ingredient.

Example 10: Peptide Hydrogels Comprising a Linker Between the Hydrogelator Part and the Biological Active Ingredient The inventors showed that a peptide with an amino acid sequence according to SEQ ID NO: 56, modified by the inclusion of an ester as linker between the hydrogelator part and the biological active ingredient (FIG. 28) was able to form a biogel spontaneously.

REFERENCES

M. Bibian, J. Mangelschots, J. Gardiner, L. Waddington, M. M. D. Acevedo, B. G. De Geest, B. Van Mele, A. Madder, R. Hoogenboom and S. Ballet, *J. Mater Chem. B.*, 2015, 3, 759-765. F. Chambon and H. H. Winter, *J. Rhea/.*, 1987, 31, 683-697.

H. Winter, *In Permanent and Transient Networks*, Springer, 1987, pp. 104-110.

D. R. Picout and S. B. Ross-Murphy, *Scientific World J.*, 2003, 3, 105-121.

R. K. Portenoy, A. Sciberras, L. Eliot, G. Loewen, J. Butler and J. Devane, *J. Pain Symptom Manage.*, 2002, 23, 292-300.

C. Clouter, J. Taliano, W. O'Mahony, M. Csanadi, G. Cohen, I Sutton, D. Sinclair, M. Awde, S. Henein and L. Robinson, *Pain Res. Manag.*, 2013, 18, 75.

X. Huang and C. S. Brazel, *J. control. Release*, 2001, 73, 121-136.

T. Holm, H. Raagel, S. E. Andaloussi, M. Hein, M. Mae, M. Pooga and O. Langel, *Biochimica et Biophysica Acta (BBA)—Biomembranes*, 2011, 1808, 1544-1551.

W. Chain and P. White, *Fmoc Solid Phase Peptide Synthesis a Practical Approach*, Oxford University Press: Oxford, 2000.

A. Novoa, S. Van Dorpe, E. Wynendaele, M. Spetea, N. Bracke, S. Stalmans, C. Betti, N. N. Chung, C. Lemieux, J. Zuegg, M. A. Cooper, D. Tourwe, B. De Spiegeleer, P. W. Schiller and S. Ballet, *J. Med. Chem.*, 2012, 55, 9549-9561.

The invention claimed is:

1. An injectable biogel composition for controlled release of a biologically active ingredient, comprising:
   an amphipathic peptide hydrogelator comprising at least 4 and at most 16 amino acid residues; wherein the amphipathic peptide hydrogelator comprises alternating hydrophobic and hydrophilic amino acids; and
   one or more biologically active ingredient(s),
   wherein the amphipathic peptide hydrogelator and the one or more biologically active ingredient(s) are covalently coupled, optionally by a linker, and
   wherein the covalent bond between the covalently coupled amphipathic peptide hydrogelator and the one or more biologically active ingredient(s) is biodegradable, and
   wherein the injectable biogel comprises of beta-sheet assemblies of the amphipathic peptide hydrogelator.

2. The biogel composition of claim 1, wherein the biologically active ingredient is a drug used for pain relief.

3. The biogel composition of claim 1, wherein the linker is biodegradable.

4. The biogel composition of claim 1, wherein the amphipathic peptide hydrogelator and biologically active ingredient form a peptide or a biodegradable peptide.

5. The biogel composition of claim 1, wherein the amphipathic peptide hydrogelator is a peptide comprising between 4 and 16 amino acids, comprising the following sequence: $(X-Y)_n$, $(X-Y)_n-X$, $(Y-X)_n$ or $(Y-X)_n-Y$, wherein
   n is an integer from 2-8,
   X is a hydrophobic amino acid and Y is a hydrophilic amino acid, and
   the N-terminus and C-terminus can be independently substituted with respectively $R^a$ and $R^b$, wherein $R^a$ is a group selected from $R^1$, or bears one $R^1$ group and one group selected from $C(=Z)R^1$, $C(=Z)ZR^1$, $C(=Z)NHR^1$ and $C(=Z)N(R^1)_2$; wherein each Z independently is O or S; wherein each $R^1$ is independently selected from H, linear or branched $C_{1-10}$alkyl, a substituted linear or branched $C_{1-10}$alkyl, a $C_{3-10}$cycloalkyl, a substituted $C_{3-10}$cycloalkyl, an aryl-$C_{1-6}$alkyl, a substituted aryl-$C_{1-6}$alkyl, an aryl, and a substituted aryl, and $R^b$ is a group selected from $OR^2$ or $N(R^2)_2$; wherein each $R^2$ independently is selected from H, linear or branched $C_{1-10}$alkyl, a substituted linear or branched $C_{1-10}$alkyl, a $C_{3-10}$cycloalkyl, a substituted $C_{3-10}$cycloalkyl, an aryl-$C_{1-6}$alkyl, a substituted aryl-$C_{1-6}$alkyl, an aryl, and a substituted aryl; or a salt form thereof.

6. The biogel composition of claim 5,
   wherein the amphipathic peptide hydrogelator is a peptide,
   wherein the N-terminus of the hydrogel-forming peptide bears one or two $R^a$ groups each independently selected from $R^1$, or bears one $R^1$ group and one group selected from $C(=Z)R^1$, $C(=Z)ZR^1$, $C(=Z)NHR^1$ and $C(=Z)N(R^1)_2$;
   wherein each Z independently is O or S;
   wherein each $R^1$ is independently selected from H, linear or branched $C_{1-10}$alkyl, a substituted linear or branched $C_{1-10}$alkyl, a $C_{3-10}$cycloalkyl, a substituted $C_{3-10}$cycloalkyl, an aryl-$C_{1-6}$alkyl, a substituted aryl-$C_{1-6}$alkyl, an aryl, and a substituted aryl; and
   wherein the C-terminus of the hydrogel-forming peptide bears a $R^b$ group selected from $OR^2$ or $N(R^2)_2$;
   wherein each $R^2$ independently is selected from H, linear or branched $C_{1-10}$alkyl, a substituted linear or branched $C_{1-10}$alkyl, a $C_{3-10}$cycloalkyl, a substituted $C_{3-10}$cycloalkyl, an aryl-$C_{1-6}$alkyl, a substituted aryl-$C_{1-6}$alkyl, an aryl, and a substituted aryl; or a salt form thereof.

7. The biogel composition of claim 1, wherein the amphipathic peptide hydrogelator is a hexapeptide.

8. The biogel composition of claim 1,
   wherein the hydrophobic amino acid(s) in the amphipatic peptide hydrogelator are selected from the group consisting of: Phe, Trp, Tyr, Ala, Val, Leu, Ile, Met, Pro and Gly; and
   wherein the hydrophilic amino acid(s) are selected from the group consisting of: Gln, Glu, Asn, Ser, Thr, Cys, Arg, His, Lys Asp and Gly.

9. The biogel composition of claim 1, wherein the amphipathic peptide hydrogelator has an amino acid sequence according to any one of SEQ ID NOs: 1 to 26 and 37 to 43, or a salt-forms thereof, the trifluoroacetic salts thereof, the sodium chloride salts thereof, or the acetic acid salts thereof.

10. The biogel composition of claim 1, wherein the biogel is a peptide with an amino acid sequence according to SEQ ID NOs: 27, 28, 29, 30, 31, 32, or 44 to 56.

11. The biogel composition of claim 1, wherein the peptide comprises a dyad formed by a β-(homo) amino-acid and an α-amino acid.

12. The biogel composition of claim 11, wherein the biogel is a peptide with an amino acid sequence according to SEQ ID NOs: 33, 34, 35, or 36.

13. A method for the controlled release of one or more biologically active ingredient(s), the method comprising:
   releasing the one or more biologically active ingredients from the biogel composition of claim 1 into its surrounding environment.

14. A method for the treatment of acute, chronic and/or neuropathic pain, the method comprising:
   administer to a subject the biogel composition so as to treat the subject with the biogel composition of claim 2.

15. The biogel composition of claim 2, wherein the drug used for pain relief is selected from the group consisting of opioids and opioid peptides, non-peptidic opioid analogues, non-opioid analgesics, antidepressants, and anticonvulsants.

16. The biogel composition of claim 3, wherein the linker is selected from the group consisting of amide, peptide bond, ester, carbonate, carbamate, glycoside, acetal, disulfide, hydrazone, tert-butyloxycarbonyl, paramethoxybenzyl, dialkyl, diaryldialkoxysilane, orthoester, β-thiopropionate, ketal, phosphoramidate, vinyl ether, imine, aconityl, trityl, polyketal, and azo.

17. The biogel composition of claim 5, wherein the amphipathic peptide hydrogelator comprises a C-terminal amide.

18. The biogel composition of claim 1, wherein the hydrophobic amino acid(s) in the amphipathic peptide hydrogelator are aromatic amino acid(s).

19. The biogel composition of claim 1, wherein the amphipathic peptide hydrogelator comprises the following sequence: $(X—Y)_n$, $(X—Y)_n—X$, $(Y—X)_n$ or $(Y—X)_n—Y$, wherein n is an integer from 2-8, X is a hydrophobic amino acid and Y is a hydrophilic amino acid.

20. The biogel composition of claim 1, wherein each amphipathic peptide hydrogelator within the biogel composition is covalently coupled, optionally by a linker, to the one or more biologically active ingredient(s).

21. The biogel composition of claim 2, wherein the drug used for pain relief is a peptide or a protein.

22. The biogel composition of claim 15, wherein the biological active ingredient is an opioid peptide selected from the group consisting of: Dmt-DLys-Phe-Phe-NH$_2$ (SEQ ID NO: 57), Dmt-DArg-Phe-Phe-NH$_2$ (SEQ ID NO: 58) and Dmt-DArg-Aba-βAla-NH$_2$ (SEQ ID NO: 59).

23. The biogel composition of claim 21, wherein the peptide or the protein, is selected from the group consisting of synthetic or natural peptides, biological macromolecules, polypeptides, proteins, peptide analogues, peptidomimetics, antibodies and antibody fragments.

* * * * *